US010590454B2

(12) United States Patent
Kshirsagar et al.

(10) Patent No.: US 10,590,454 B2
(45) Date of Patent: Mar. 17, 2020

(54) METHODS OF PREVENTING AND REMOVING TRISULFIDE BONDS

(71) Applicant: Biogen MA Inc., Cambridge, MA (US)

(72) Inventors: Rashmi Rohit Kshirsagar, Ashland, MA (US); Alan Gilbert, Arlington, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 15/785,268

(22) Filed: Oct. 16, 2017

(65) Prior Publication Data

US 2018/0251805 A1 Sep. 6, 2018

Related U.S. Application Data

(60) Continuation of application No. 15/425,056, filed on Feb. 6, 2017, now Pat. No. 9,790,533, which is a division of application No. 14/117,554, filed as application No. PCT/US2012/037610 on May 11, 2012, now Pat. No. 9,562,252.

(60) Provisional application No. 61/617,529, filed on Mar. 29, 2012, provisional application No. 61/485,973, filed on May 13, 2011.

(51) Int. Cl.
| C12P 21/00 | (2006.01) |
| A61K 39/395 | (2006.01) |
| C07K 1/113 | (2006.01) |
| C12N 5/00 | (2006.01) |
| C07K 16/00 | (2006.01) |
| A61K 39/00 | (2006.01) |

(52) U.S. Cl.
CPC ........ *C12P 21/00* (2013.01); *A61K 39/39591* (2013.01); *C07K 1/1133* (2013.01); *C07K 16/00* (2013.01); *C12N 5/0018* (2013.01); *A61K 2039/505* (2013.01); *C07K 2317/40* (2013.01); *C07K 2317/41* (2013.01); *C07K 2317/94* (2013.01); *C12N 2500/34* (2013.01)

(58) Field of Classification Search
CPC .. C07K 16/00; C07K 1/1133; C07K 2317/24; C07K 2317/56; A61K 2039/505; C12N 2510/02
See application file for complete search history.

(56) References Cited

U.S. PATENT DOCUMENTS

| 4,411,993 | A  | 10/1983 | Gillis |
| 6,458,565 | B1 | 10/2002 | Cunningham et al. |
| 7,232,894 | B1 | 6/2007  | Hemmendorff et al. |
| 7,425,328 | B2 | 9/2008  | Wang |
| 7,470,779 | B2 | 12/2008 | Boyle et al. |
| 7,993,644 | B2 | 8/2011  | Wang |
| 8,841,424 | B2 | 9/2014  | Wirtz et al. |
| 8,933,202 | B2 | 1/2015  | Hettmann et al. |
| 9,005,926 | B2 | 4/2015  | Evans et al. |
| 9,562,252 | B2 | 2/2017  | Kshirsagar et al. |
| 9,790,533 | B2 | 10/2017 | Kshirsagar et al. |
| 10,308,706 | B2 | 6/2019 | Evans et al. |
| 2004/0048315 | A1 | 3/2004 | Rathore et al. |
| 2006/0194280 | A1 | 8/2006 | Dillon et al. |
| 2008/0299668 | A1 | 12/2008 | Xue et al. |
| 2012/0264916 | A1 | 10/2012 | Evans et al. |
| 2014/0295495 | A1 | 10/2014 | Kshirasagar et al. |
| 2015/0274808 | A1 | 10/2015 | Evans et al. |
| 2017/0247655 | A1 | 8/2017 | Kshirsagar et al. |

FOREIGN PATENT DOCUMENTS

| JP | S57179749 A | 11/1982 |
| JP | H0517431 A | 1/1993 |
| JP | H0789856 A | 4/1995 |
| JP | 2011/051946 A | 3/2011 |
| WO | WO 94/24157 A1 | 10/1994 |
| WO | WO 96/02570 A1 | 2/1996 |
| WO | WO 98/56418 A1 | 12/1998 |
| WO | WO 00/02900 A1 | 1/2000 |
| WO | WO 01/18175 A1 | 3/2001 |
| WO | WO 02/066603 A2 | 8/2002 |
| WO | WO 2004/031213 A1 | 4/2004 |
| WO | WO 2004/094475 A2 | 11/2004 |
| WO | WO 2006/069940 A1 | 7/2006 |
| WO | WO 2007/008547 A2 | 1/2007 |
| WO | WO 2008/086006 A2 | 7/2008 |
| WO | WO 2008/141207 A1 | 11/2008 |
| WO | WO 2009/062690 A1 | 5/2009 |
| WO | WO 2009/140177 A2 | 11/2009 |
| WO | WO 2010/005570 A2 | 1/2010 |

(Continued)

OTHER PUBLICATIONS

EP 12723781.6-1109, Jan. 11, 2019, Notice of Opposition to a European Patent.
EP 12723781.6-1109, Jan. 23, 2019, Notice of Opposition to a European Patent.
EP 18167804.6-1109, Sep. 13, 2018, Extended European Search Report.
PCT/US2012/037610, Sep. 17, 2012, International Search Report and Written Opinion.
PCT/US2012/037610, Nov. 28, 2013, International Preliminary Report on Patentability.
PCT/US2010/051189, Feb. 3, 2011, International Search Report and Written Opinion.

(Continued)

*Primary Examiner* — Kagnew H Gebreyesus
(74) *Attorney, Agent, or Firm* — Wolf, Greenfield & Sacks, P.C.

(57) ABSTRACT

The present invention pertains to methods of preventing and eliminating trisulfide bonds in proteins such as antibodies. In one embodiment, trisulfide bonds in proteins are converted to disulfide bonds as part of chromatographic purification procedures. In another embodiment, the formation of trisulfide bonds in proteins is inhibited by implementation of methods described herein during the cell culture production of such proteins. In another embodiment, monoclonal antibodies are produced by the methods described herein.

13 Claims, 10 Drawing Sheets

Figure 1:
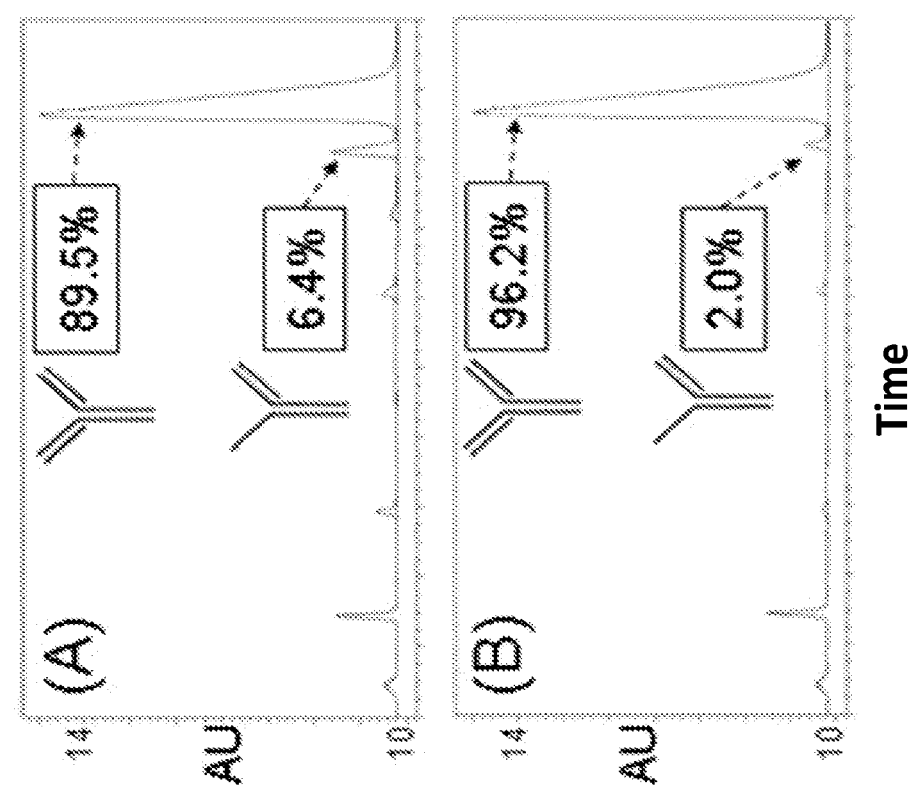

Specification includes a Sequence Listing.

(56) References Cited

FOREIGN PATENT DOCUMENTS

| WO | WO 2011/027551 A1 | 3/2011 | | |
|---|---|---|---|---|
| WO | WO 2011/041721 A1 | 4/2011 | | |
| WO | WO-2011041721 A1 * | 4/2011 | ........... | C07K 1/1133 |
| WO | WO 2012/040216 A1 | 3/2012 | | |
| WO | WO 2012/158551 A1 | 11/2012 | | |

OTHER PUBLICATIONS

PCT/US2010/051189, Apr. 3, 2012, International Preliminary Report on Patentability.
International Search Report and Written Opinion for Application No. PCT/US2010/051189 dated Feb. 3, 2011.
International Preliminary Report on Patentability for Application No. PCT/US2010/051189 dated Apr. 3, 2012.
International Search Report and Written Opinion for Application No. PCT/US2012/037610 dated Sep. 17, 2012.
International Preliminary Report on Patentability for Application No. PCT/US2012/037610 dated Nov. 28, 2013.
Notice of Opposition to a European patent for Application No. EP12723781.6 dated Jan. 11, 2019.
Notice of Opposition to a European patent for Application No. EP12723781.6 dated Jan. 23, 2019.
Extended European Search Report for Application No. EP 18167804.6 dated Sep. 13, 2018.
Office Action for U.S. Appl. No. 13/499,858 dated Oct. 2, 2013.
Office Action for U.S. Appl. No. 13/499,858 dated Mar. 20, 2014.
Office Action for U.S. Appl. No. 14/117,554 dated May 13, 2016.
[No Author Listed] Wikipedia: Methylglyoxal. Oct. 27, 2018. Retrieved from https://en.wikipedia.org/wiki/index.hph?title=Methylglyoxal&oldid=865914649.
[No Author Listed], 3rd Party Observations under Art 115 EPC—EPA No. 10763112.9, 10 pages, Apr. 28, 2016.
Andersson et al., Isolation and Characterization of a Trisulfide Variant of Recombinant Human Growth Hormone formed During Expression in *Escherichiacoli*. International Journal of Peptide and Protein Research. Apr. 1996;47(4):311-321.
Aono et al., Efficient On-column Conversion of IgG1 Trisulfide Linkages to Native Disulfides in Tandem with Protein A Affinity Chromatography. Journal of Chromatography. Aug. 2010;A1217(32):5225-5232.
Banks et al., Removal of Cysteinylation from an Unpaired Sulfhydryl in the Variable Region of a Recombinant Monoclonal IGG1 Antibody Improves Homogeneity, Stability, and Biological Activity. Journal of Pharmaceutical Sciences. Feb. 2008;97(2):775-790.
Baran et al., Solid-phase Enzyme Modification via Affinity Chromatography. Journal of Chromatography. Sep. 2003;B794(2):311-322.
Breton et al., Detection of Traces of a Trisulphide Derivative in the Preparation of Recombinant Truncated Interleukin-6 Mutein. Journal of Chromatography. Aug. 1995;A709(1):135-146.
Canova-Davis et al., Confirmation by Mass Spectrometry of a Trisulfide Variant in Methionyl Human Growth Hormone Biosynthesized in *Escherichia coli*. Analytical Chemistry. Nov. 1996;68(22):4044-4051.
Chiku, T., et al., H2S Biogenesis by Human Cystathionine gamma-lyase Leads to the Novel Sulfur Metabolites Lanthionine and Homolanthionine and is Responsive to the Grade of Hyperhomocysteinemia. The Journal of Biological Chemistry. Apr. 2009;284(17):11601-11612.
Gallogly et al., Mechanisms of Reversible Protein Glutathionylation in Redox Signaling and Oxidative Stress. Current Opinion in Pharmacology. Aug. 2007;7(4):381-391.
Glocker et al., Characterization of Disulfide Linkages and Disulfide Bond Scrambling in Recombinant Human Macrophage Colony Stimulating Factor by Fast-atom Bombardment Mass Spectrometry of Enzymatic Digests. Journal of the American Societyfor Mass Spectrometry. Aug. 1995;6(8):638-643.
Glockshuber et al., The Disulfide Bonds in Antibody Variable Domains: Effects on Stability, Folding in Vitro, and Functional Expression in *Escherichia coli*. Biochemistry. Feb. 1992;31(5):1270-1279.
Goodwin et al., Determination of Sulfide in Brain Tissue by Gas Dialysis/Ion Chromatography: Postmortem Studies and Two Case Reports. Journal of Analytical Toxicology. Mar. 1989;13(2):105-109.
Grigorian et al., Extraordinarily Stable Disulfide-linked Homodimer of Human Growth Hormone. Protein Science. Apr. 2005;14(4):902-913.
Gu et al., Characterization of Trisulfide Modification in Antibodies. Analytical Biochemistry. May 2010;400(1):89-98.
Houde et al., Rapid Characterization of IgG1 Conformation and Conformational Dynamics by Hydrogen/deuterium Exchange Mass Spectrometry. Analytical Chemistry. Apr. 2009;81(7):2644-2651.
Houen et al., Preparation of Bioconjugates by Solid-phase Conjugation to Ion Exchange Matrix-adsorbed Carrier Proteins. Bioconjugate Chemistry. Jan. 2003;14(1):75-79.
Jenkins et al., Post-translational Modifications of Recombinant Proteins: Significance for Biopharmaceuticals. Molecular Biotechnology. Jun. 2008;39(2):113-118.
Jespersen et al., Characterisation of a Trisulphide Derivative of Biosynthetic Human Growth Hormone Produced in *Escherichia coli*. Eur J Biochem. Jan. 15, 1994;219(1-2):365-73.
Kamoun, Endogenous Production of Hydrogen Sulfide in Mammals. Amino Acids. Jun. 2004;26(3):243-254.
Kim et al., Effects of Supplementation of Various Medium Components on Chinese Hamster Ovary Cell Cultures Producing Recombinant Antibody. Cytotechnology. 2005;47(1-3):37-49.
Kshirsagar et al., Controlling Trisulfide Modification in Recombinant Monoclonal Antibody Produced in Fed-batch Cell Culture. Biotechnology and Bioengineering. Oct. 2012;109(10):2523-2532.
Labrijn et al., Therapeutic IgG4 Antibodies Engage in Fab-arm Exchange with Endogenous Human IgG4 in Vivo. Nature Biotechnology. Aug. 2009;27(8):767-771.
Liu et al., Disulfide bond structures of IgG molecules: Structural variations, chemical modifications and possible impacts to stability and biological function. mAbs. Jan.-Feb. 2012;4(1):17-23. doi: 10.4161/mabs.4.1.18347.
Liu et al., Heterogeneity of Monoclonal Antibodies. Journal of Pharmaceutical Sciences. Jul. 2008;97(7);2426-2447.
Liu et al., Human IgG2 Antibody Disulfide Rearrangement in Vivo. The Journal of Biological Chemistry. Oct. 2008;283(43)29266-29272.
Okado-Matsumoto et al., Modification of Cysteine 111 in Human Cu,Zn-superoxide Dismutase. Free Radical Biology & Medicine. Dec. 2006;41(12):1837-1846.
Pristatsky et al., Evidence for Trisulfide Bonds in a Recombinant Variant of a Human IgG2 Monoclonal Antibody. Analytical Chemistry. Aug. 2009;81(15):6148-6155.
Singh et al., Relative Contributions of Cystathionine beta-synthase and gamma-Cystathionase to H2S Biogenesis via Alternative Trans-Sulfuration Reactions. The Journal of Biological Chemistry. Aug. 2009;284(33):22457-22466.
Srebalus et al., Applications of Mass Spectrometry for the Structural Characterization of Recombinant Protein Pharmaceuticals. Mass spectrometry Reviews. May 2007;26(3):370-388.
Stipanuk et al., Characterization of the Enzymic Capacity for Cysteine Desulphhydration in Liver and Kidney of the Rat. The Biochemical Journal. Aug. 1982;206(2):267-277.
Thomsen et al., Pharmacological Characterization of a Biosynthetic Trisulfide-Containing Hydrophobic Derivative of Human Growth Hormone: Comparison with Standard 22 K Growth Hormone. Pharmacology & Toxicology. Jun. 1994;74(6):351-358.
Zhang et al., Mass Spectrometry for Structural Characterization of Therapeutic Antibodies. Mass Spectrometry Reviews. Jan. 2009;28(1):147-176.
Zhao et al., H(2)S-induced Vasorelaxation and Underlying Cellular and Molecular Mechanisms. American Journal of Physiology Heart and Circulatory Physiology. Aug. 2002;283(2):H474-H480.

(56) References Cited

OTHER PUBLICATIONS

Zhao et al., The Vasorelaxant Effect of H(2)S as a Novel Endogenous Gaseous K(ATP) Channel Opener. The EMBO Journal. Nov. 2001;20(21):6008-6016.

* cited by examiner

METHODS OF PREVENTING AND REMOVING TRISULFIDE BONDS

RELATED APPLICATIONS

This application is a continuation of application Ser. No. 15/425,056, filed Feb. 6, 2017 and entitled "METHODS OF PREVENTING AND REMOVING TRISULFIDE BONDS" which is a divisional of application Ser. No. 14/117,554, filed Apr. 3, 2014 and entitled "METHODS OF PREVENTING AND REMOVING TRISULFIDE BONDS" which is a national stage filing under 35 U.S.C. § 371 of PCT International Application PCT/US2012/037610, filed May 11, 2012 and entitled "METHODS OF PREVENTING AND REMOVING TRISULFIDE BONDS," which claims the benefit under 35 U.S.C. § 119(e) of U.S. provisional application No. 61/617,529, filed Mar. 29, 2012 and U.S. provisional application No. 61/485,973, filed May 13, 2011, the contents of each of which are incorporated by reference herein in their entirety.

BACKGROUND OF THE INVENTION

Field of the Invention

The present invention relates to methods of preventing and eliminating the formation of trisulfide bonds in proteins during protein production.

Background Art

Recombinant proteins, and in particular, monoclonal antibodies (mAbs), have become an important class of therapeutic compounds employed for the treatment of a broad range of diseases. Recent successes in the field of biotechnology have improved the capacity to produce large amounts of such proteins. However, extensive characterization of the products demonstrates that the proteins are subject to considerable heterogeneity. For example, molecular heterogeneity can result from chemically-induced modifications such as oxidation, deamidation, and glycation as well post-translational modifications such as proteolytic maturation, protein folding, glycosylation, phosphorylation, and disulfide bond formation. Molecular heterogeneity is undesirable because therapeutic products must be extensively characterized by an array of sophisticated analytical techniques and meet acceptable standards that ensure product quality and consistency.

Antibodies (or immunoglobulins) are particularly subject to such structural heterogeneity due to the fact that they are large, multi-chain molecules. For example, IgG antibodies are composed of four polypeptide chains: two light chain polypeptides (L) and two heavy chain polypeptides (H). The four chains are typically joined in a "Y" configuration by disulfide bonds that form between cysteine residues present in the heavy and light chains. These disulfide linkages govern the overall structure of the native $H_2L_2$ tetramer. Overall, IgG1 antibodies contain four interchain disulfide bonds, including two hinge region disulfides that link the H chains, and one disulfide bond between each heavy H and L chain. In addition, twelve intrachain disulfide linkages may involve each remaining cysteine residue present in the molecule. Incomplete disulfide bond formation, or bond breakage via oxidation or beta-elimination followed by disulfide scrambling, are all potential sources of antibody heterogeneity. In addition, a further type of modification, namely trisulfide ($—CH_2—S—S—S—CH_2—$) bond formation, was recently reported within the interchain, hinge region bonds of a human IgG2 antibody. See, Pristatsky et al., Anal. Chem. 81: 6148 (2009).

Trisulfide linkages have previously been detected in superoxide dismutase (Okado-Matsumoto et al., Free Radical Bio. Med. 41: 1837 (2006)), a truncated form of interleukin-6 (Breton et al., J. Chromatog. 709: 135 (1995)), and bacterially expressed human growth hormone (hGH) (Canova-Davis et al., Anal. Chem. 68: 4044 (1996)). In the case of hGH, it was speculated that trisulfide formation was promoted by $H_2S$ released during the fermentation process. See, International Published Patent Application No. WO 96/02570. Consistent with this hypothesis, the trisulfide content of hGH was increased by exposure to $H_2S$ in solution. See, U.S. Pat. No. 7,232,894. In addition, exposing bioreactor material or bacterial lysate to an inert gas inhibited trisulfide formation, apparently by stripping $H_2S$ from the system. See, International Published Patent Application No. WO 2006/069940.

Conditions that influence the level of trisulfide in hGH generated during purification from bacteria have previously been reported. For example, the presence of alkali metal salts has been reported to inhibit increases in trisulfide bonds during downstream protein processing. See, U.S. Pat. No. 7,232,894. Furthermore, treatment of hGH with reduction-oxidation (REDOX) compounds, including L-cysteine, in solution was found to convert trisulfide bonds to disulfide bonds. See, International Published Patent Application No. WO 94/24157. For example, treatment of purified IgG2 with a 20-fold molar ratio of L-cysteine in solution was found to convert hinge region trisulfide bonds to disulfides during sample preparation for analytical studies. See, Pristatsky et al., Anal. Chem. 81: 6148 (2009).

Unfortunately, removal of trisulfide bonds by exposure to cysteine in solution has several drawbacks, in particular for large scale processing. For example, large quantities of cysteine are required. This method also necessitates a separate step to remove cysteine from the sample after trisulfide bonds are removed. In addition, removal of trisulfide bonds by exposure to cysteine in solution can promote aggregation through the formation of undesirable disulfide linkages. Therefore, in order to address the limitations of previous methods for reducing trisulfide bonds, the methods described herein provide efficient and improved means for preventing and eliminating the formation of trisulfide bonds in proteins (such as, for example, in antibodies) during production and purification procedures used in the manufacture of such proteins.

BRIEF SUMMARY OF THE INVENTION

The present invention pertains to methods of preventing and eliminating trisulfide bonds in proteins such as antibodies. In one embodiment, trisulfide bonds in proteins are converted to disulfide bonds as part of chromatographic purification procedures. In another embodiment, the formation of trisulfide bonds in proteins is inhibited by implementation of methods described herein during the cell culture production of such proteins.

BRIEF DESCRIPTION OF THE DRAWINGS/FIGURES

FIG. 1: Indirect assessment of IgG1 mAb trisulfide content by heat induced fragmentation. Samples were heated and analyzed by non-reducing capillary electrophoresis (CE-SDS assay). In each electropherogram, the main peak corresponds to intact H₂L₂ tetramer (indicated by the upper schematic and arrow), and the adjacent peak, which represents the single most abundant impurity, has a migration pattern consistent with a species lacking one light chain (HHL species; indicated by the lower schematic and arrow). The percent of total peak area is indicated for the intact $H_2L_2$ tetramer and the HHL species, respectively. (A) IgG1 mAb-A containing 13.1% H-L trisulfide (percent trisulfide determined by peptide mapping analysis). (B) IgG1 mAb-A-LT—an alternative preparation of mAb-A in which trisulfide was undetectable by peptide mapping.

Figure 2:
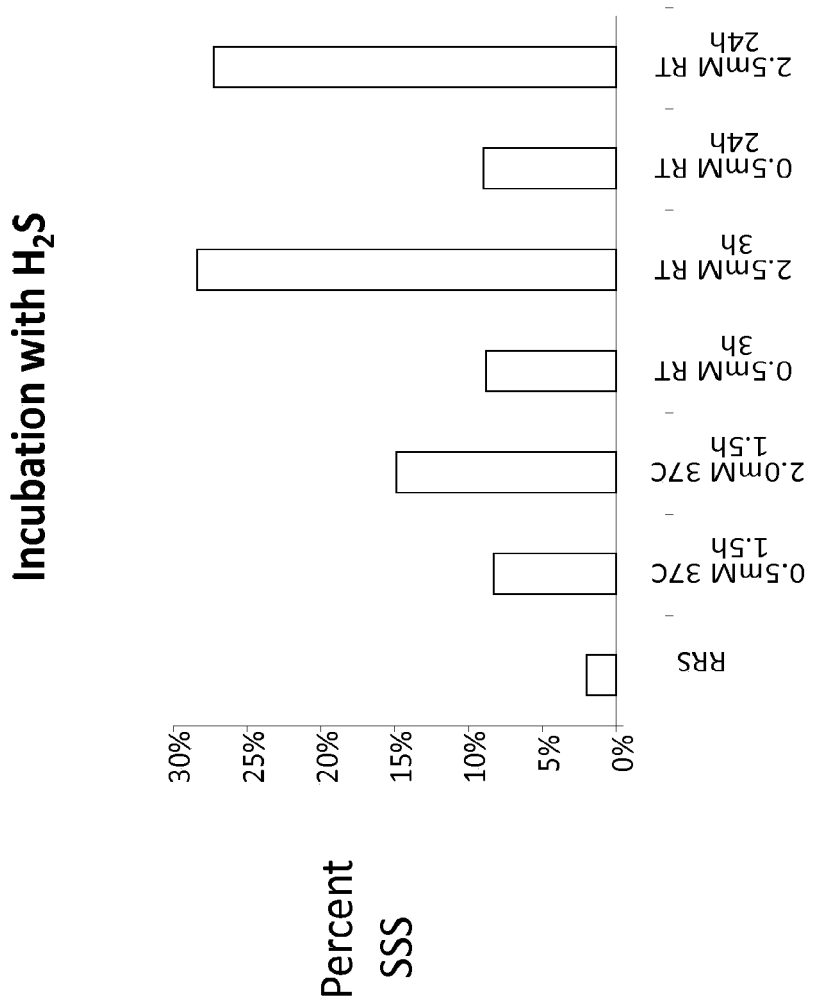

FIG. 2: Bar graph displaying the effect of hydrogen sulfide (mM) on trisulfide levels. Samples were taken from cultures exposed to variable concentrations of hydrogen sulfide (mM) over various times. Samples were purified using Protein A and subjected to peptide mapping analysis to determine the percentage of trisulfide bonds. The bar height represents the average percentage of antibodies having at least one trisulfide bond between the heavy and light chains.

Figure 3:
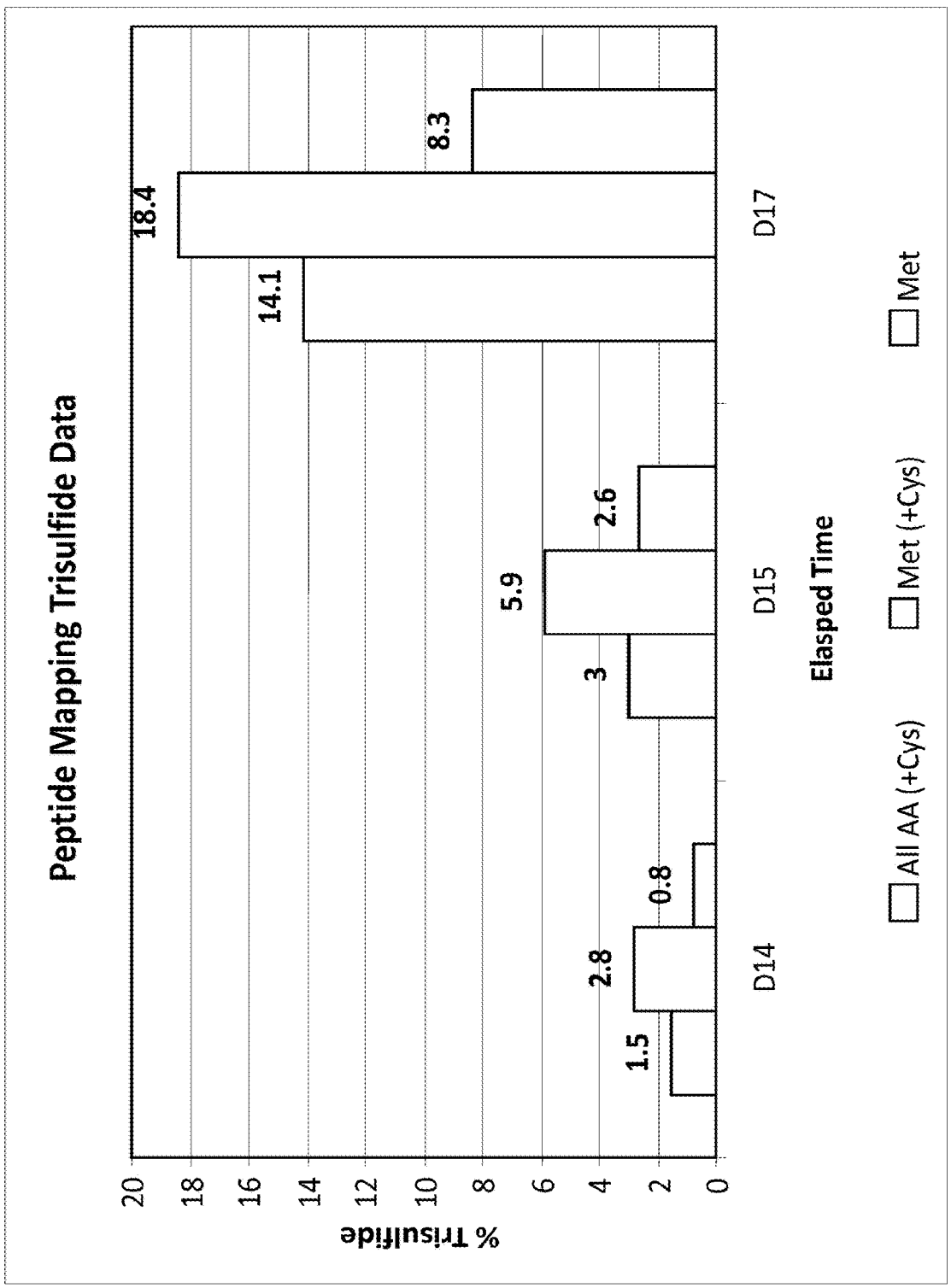

FIG. 3: Bar graph displaying the effect of cysteine concentration on trisulfide levels. Samples were taken from cell cultures fed with or without supplemental cysteine (i.e., complete feed+total amino acid supplement+supplemental Cys; complete feed+supplemental Cys & Met; complete feed+supplemental Met only). Samples were purified using Protein A and subjected to peptide mapping analysis to determine the percentage of trisulfide bonds present. The bar height represents the average percentage of antibodies containing at least one trisulfide bond between the heavy and light chains.

Figure 4:
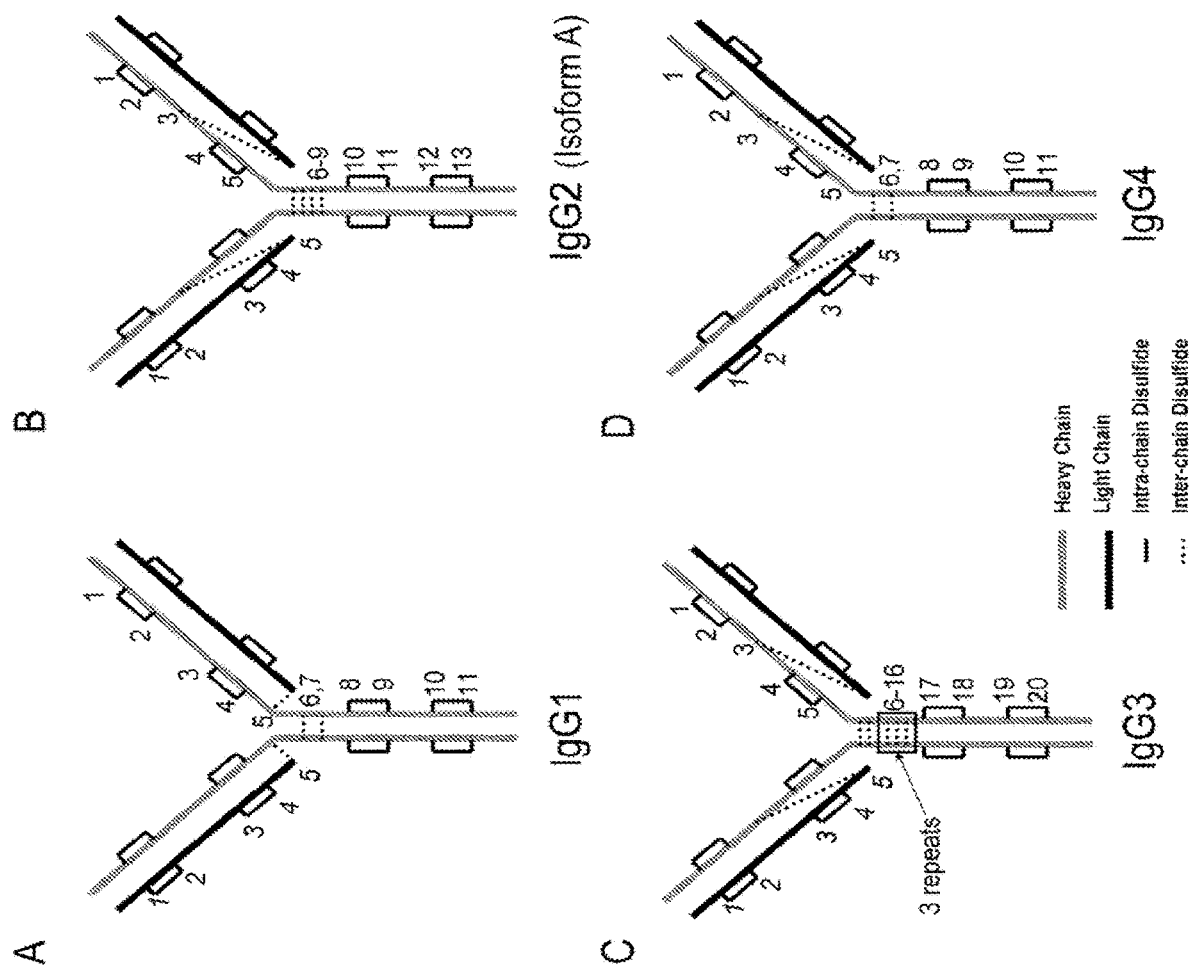

FIG. 4: Schematic drawings of the disulfide connectivity in human IgG antibodies. (A) IgG1, (B) IgG1, (C) IgG3, and (D) IgG4. Cys residues are numbered based on their position in the sequence, where "1" is the Cys residue closest to the N-terminus.

Figure 5:
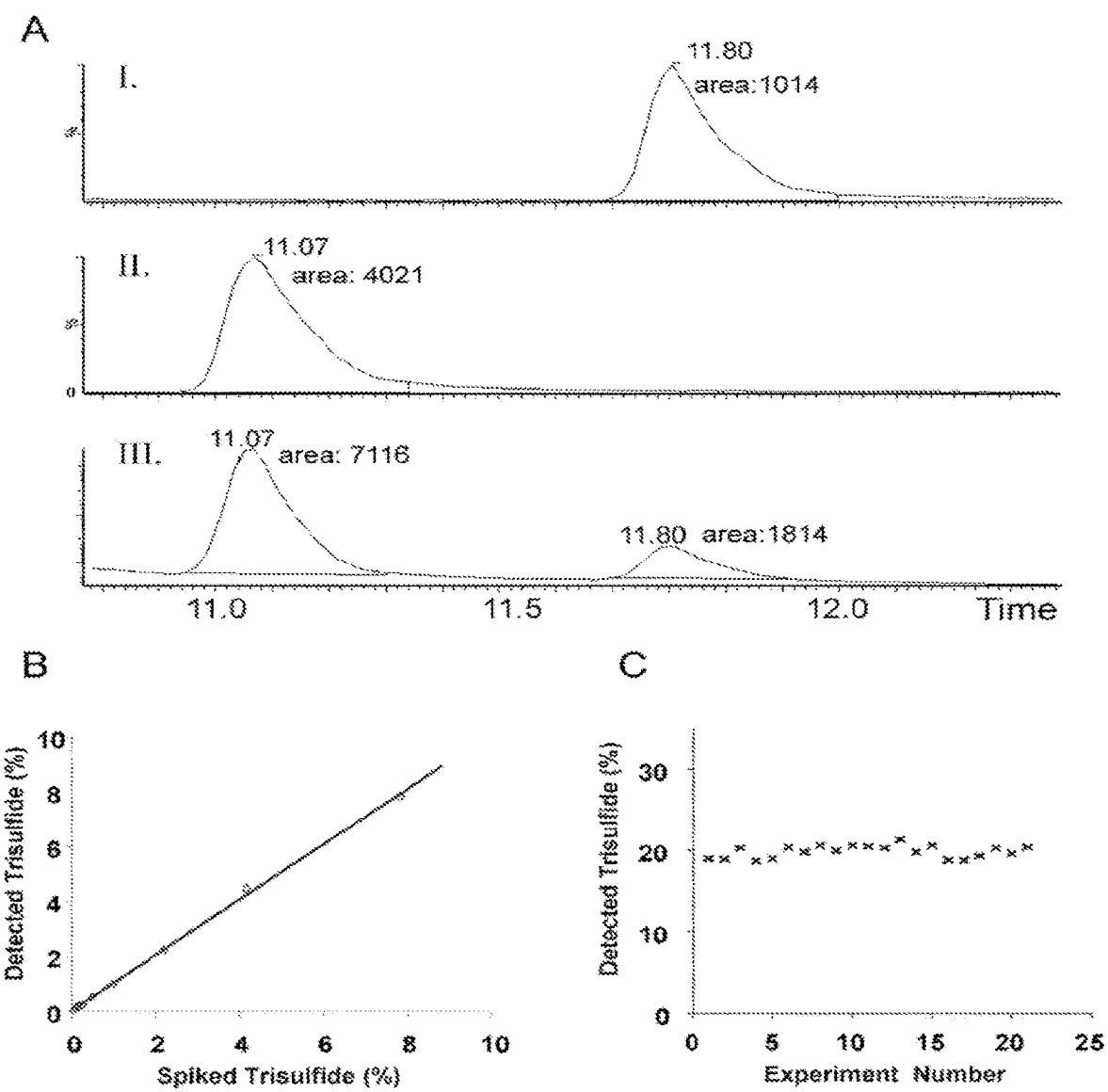

FIG. 5: Extracted ion chromatograms (EIC) and UV trace showing the disulfide- and trisulfide-linked Lys-C peptide clusters connecting the fifth Cys residues of the light and heavy chains of mAb1. (A-I) the EIC of the trisulfide-linked PepLL12/PepHL13; (A-II) the EIC of the disulfide-linked PepLL12/PepHL13; (A-III) UV profile at 214 nm. The numbers shown in each panel are the integrated peak areas. (B) Plot of the detected amounts of the trisulfide at the LC5-HC5 linkage in mAb2 samples that had been spiked with varying amounts of a mAb2-D containing 7.8% trisulfide in the LC5-HC5 linkage. (C) Plot showing reproducibility of the focused Lys-C peptide mapping method.

Figure 6:
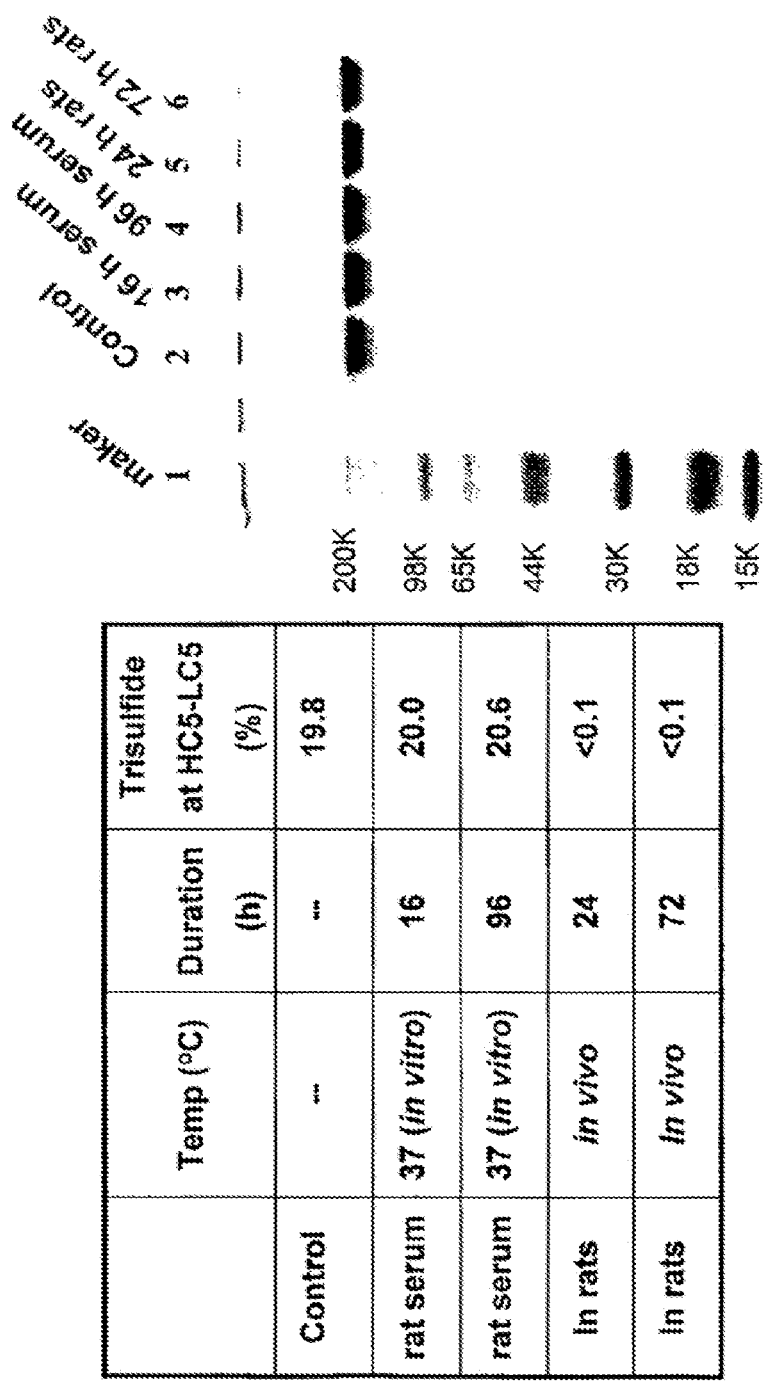

FIG. 6: Trisulfides are Stable in vitro in Rat Serum, but Rapidly Convert to Disulfides in vivo.

Figure 7:
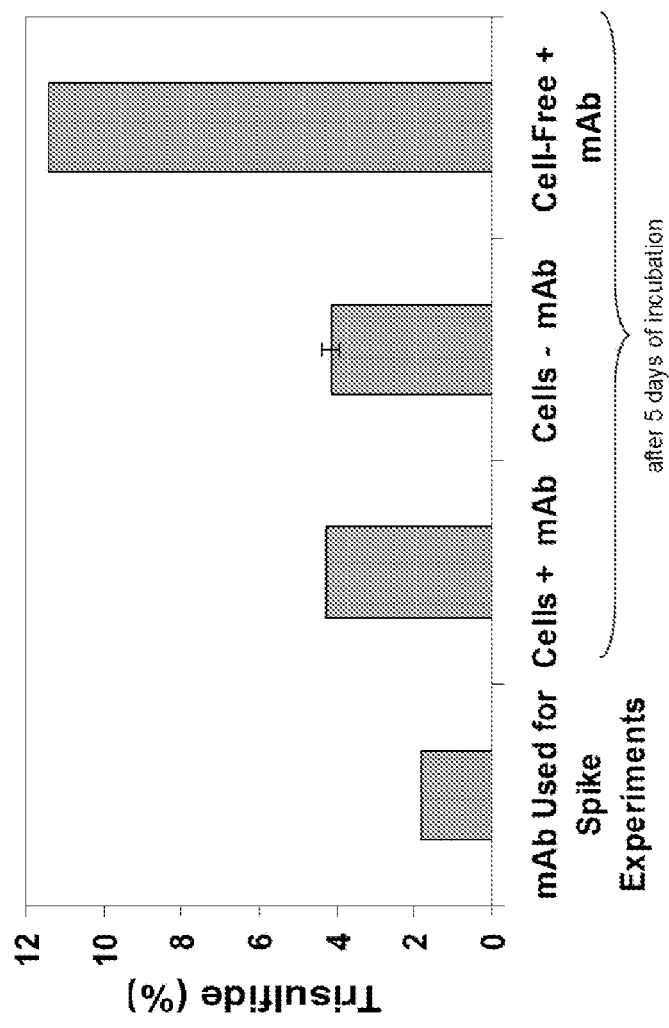

FIG. 7: Comparison of trisulfide formation in spiked antibody preparations. Purified antibody which contains 1.8% trisulfide content was spiked into cultures in the presence or absence of cells. Trisulfide formation was highest in cultures which did not contain cells (approximately 11%). Addition of cells to the culture decreased trisulfide formation.

Figure 8:
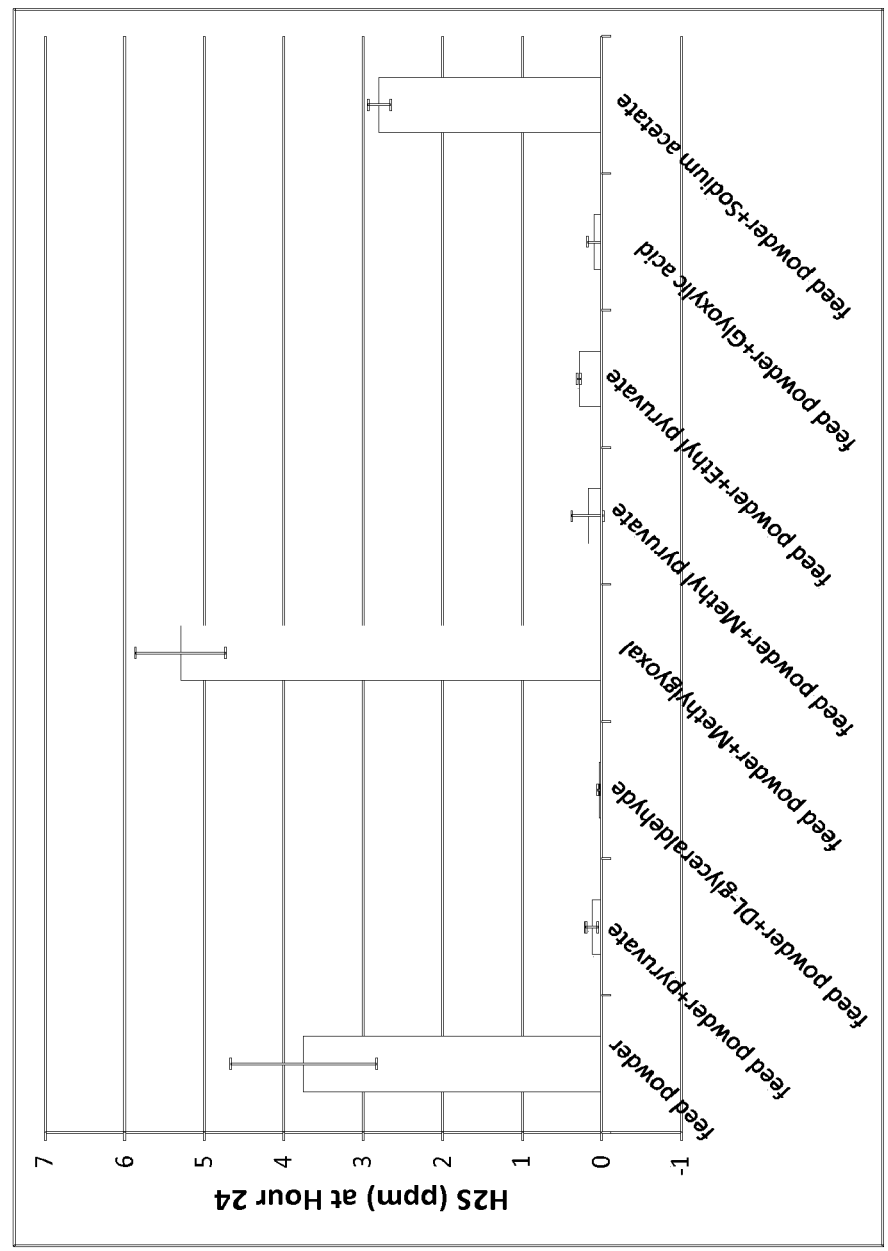

FIG. 8: Effects of different media additives on release of hydrogen sulfide. Pyruvate, methyl pyruvate, ethyl pyruvate, DL-glyceraldehyde, and glyoxylic acid decrease hydrogen sulfide.

Figure 9:
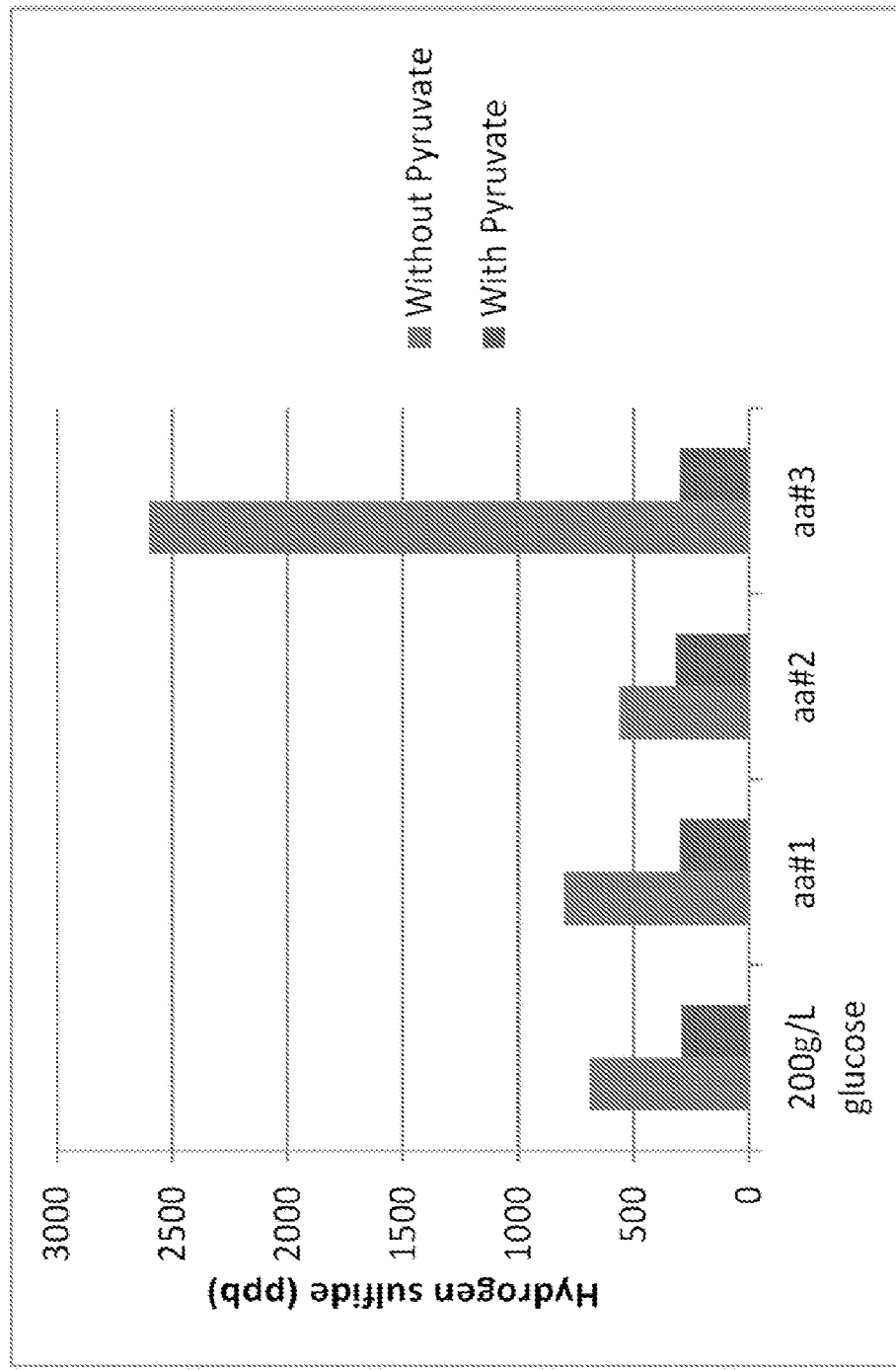

FIG. 9: Effect of pyruvate on hydrogen sulfide in solution with cysteine and glucose or cysteine and amino acids. aa #1, aa #2, and aa #3 represent subgroupings of amino acids present in the feed liquid.

Figure 10:
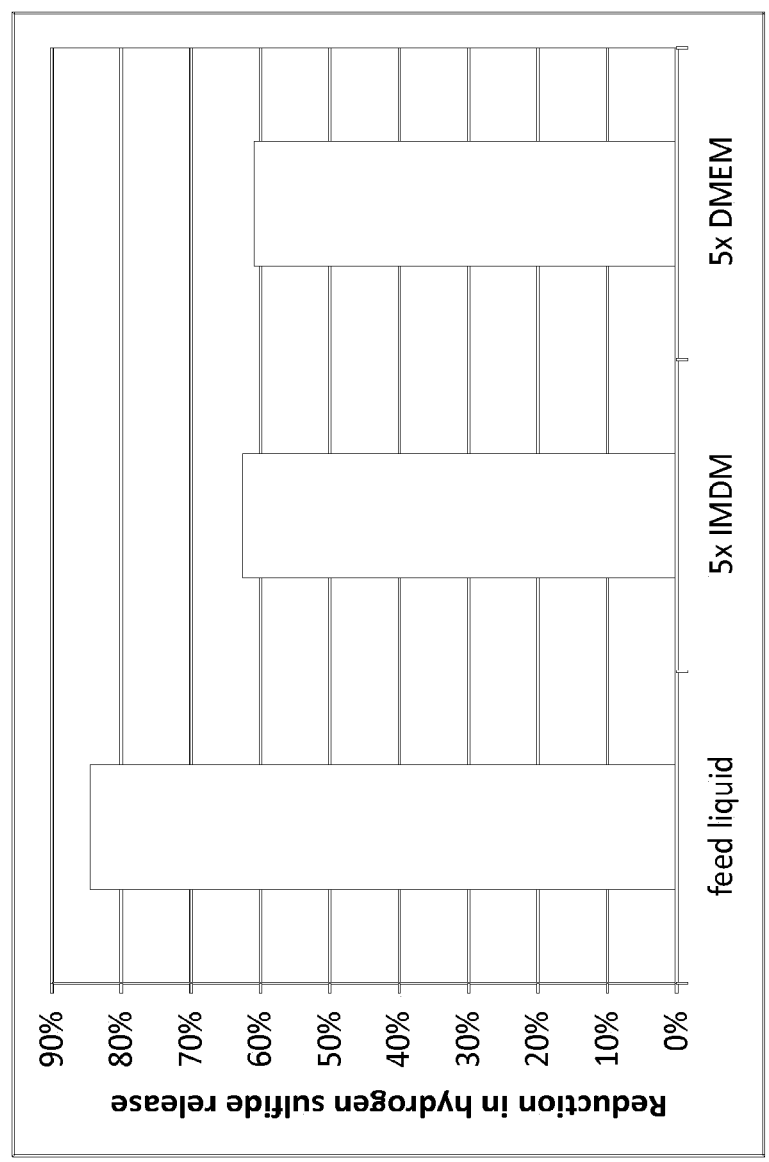

FIG. 10: Effect of pyruvate on hydrogen sulfide in various media. All cysteine concentrations were normalized to that in feed liquid. Iscove's Modified Dulbecco's Medium (IMDM) and Dulbecco's Modified Eagle Medium (DMEM) are common cell-culture media.

DETAILED DESCRIPTION OF THE INVENTION

I. Definitions

It is to be noted that the term "a" or "an" entity refers to one or more of that entity; for example, "an antibody" or "a protein" is understood to represent one or more antibody or protein molecules, respectively. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Likewise, the term "protein" refers to any chain or chains of two or more polypeptide. Hence, an antibody may be referred to as "a protein" even though it is comprised of multiple polypeptides (for example, an IgG antibody is comprised of two heavy chain and two light chain polypeptides). Thus, peptides, dipeptides, tripeptides, oligopeptides, "amino acid chain," or any other term used to refer to a chain or chains of two or more amino acids, are included within the definition of "protein" or "polypeptide," and the terms "protein" or "polypeptide" may be used instead of, or interchangeably with any of these terms. Hence, because the terms "protein" and "polypeptide" encompass plural polypeptides, these terms encompass polypeptide multimers such as antibodies.

The term "polypeptide" is also intended to refer to the products of post-expression modifications of the polypeptide, including without limitation glycosylation (e.g. modification with N-acetyl glucosamine, galactose, or sialic acid moities), pegylation (i.e. covalent attachment of polyethylene glycol) acetylation, phosphorylation, amidation, glycation (e.g. dextran modification), derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It can be generated in any manner, including by chemical synthesis.

Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to antibodies or antibody polypeptides of the present invention include any polypeptides which retain at least some of the antigen-binding properties of the corresponding native antibody or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring Non-naturally occurring variants may be produced using art-known mutagenesis techniques. Variant polypeptides may comprise conservative or non-conservative amino acid substitutions, deletions or additions. Derivatives of antibodies and antibody polypeptides of the present invention, are polypeptides which have been altered so as to exhibit additional features not found on the native polypeptide. Examples include fusion proteins. Variant polypeptides may also be referred to herein as "polypeptide analogs." As used herein a "derivative" of an antibody or antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

Proteins secreted by mammalian cells can have a signal peptide or secretory leader sequence which is cleaved from the mature protein once export of the growing protein chain across the rough endoplasmic reticulum has been initiated. Polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse ß-glucuronidase.

The present methods include the use of antibodies, or antigen-binding fragments, variants, or derivatives thereof. Unless specifically referring to full-sized antibodies such as naturally-occurring antibodies, the term "antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., *Antibodies: A Laboratory Manual*, (Cold Spring Harbor Laboratory Press, 2nd ed. 1988).

The term "immunoglobulin" comprises various broad classes of polypeptides that can be distinguished biochemically. Heavy chains are classified as gamma, mu, alpha, delta, or epsilon, ($\gamma$, $\mu$, $\alpha$, $\delta$, $\epsilon$) with some subclasses among them (e.g., $\gamma1$-$\gamma4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope described herein although the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, *J. Mol. Biol.*, 196:901-917 (1987), which are incorporated herein by reference in their entireties).

Antibodies or antigen-binding fragments, variants, or derivatives thereof include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies. ScFv molecules are known in the art and are described, e.g., in U.S. Pat. No. 5,892,019. Immunoglobulin or antibody molecules can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibody fragments, including single-chain antibodies, may comprise the variable region(s) alone or in combination with the entirety or a portion of the following: hinge region, CH1, CH2, and CH3 domains. Also included are antigen-binding fragments comprising any combination of variable region(s) with a hinge region, CH1, CH2, and CH3 domains. Antibodies or immunospecific fragments thereof can be from any animal origin including birds and mammals. The antibodies can be human, murine, donkey, rabbit, goat, guinea pig, camel, llama, horse, or chicken antibodies. In another embodiment, the variable region may be condrictoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al. A human antibody is still "human" even if amino acid substitutions are made in the antibody.

As used herein, the term "heavy chain portion" includes amino acid sequences derived from an immuno globulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. The light chain portion can comprise at least one of a VL or CL domain.

Antibodies, or antigen-binding fragments, variants, or derivatives thereof disclosed herein may be described or specified in terms of the epitope(s) or portion(s) of an antigen, e.g., a target polypeptide that they recognize or specifically bind. The portion of a target polypeptide which specifically interacts with the antigen binding domain of an antibody is an "epitope," or an "antigenic determinant." A target polypeptide can comprise a single epitope, at least two epitopes, or any number of epitopes, depending on the size, conformation, and type of antigen. Furthermore, it should be noted that an "epitope" on a target polypeptide may be or include non-polypeptide elements, e.g., an "epitope may include a carbohydrate side chain.

Antibodies or antigen-binding fragments, variants or derivatives thereof may be "multispecific," e.g., bispecific, trispecific or of greater multispecificity, meaning that it recognizes and binds to two or more different epitopes present on one or more different antigens (e.g., proteins) at the same time. Thus, whether an antibody is "monospecific" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in an antibody. Each binding domain specifically binds one epitope. When an antibody comprises more than one binding domain, each binding domain may specifically bind the same epitope, for an antibody with two binding domains, termed "bivalent monospecific," or to different epitopes, for an antibody with two binding domains, termed "bivalent bispecific." An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Appl. Publ. Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

The term "trisulfide bond" is described further below.

As used herein, the term "chimeric antibody" will be held to mean any antibody wherein the immunoreactive region or site is obtained or derived from a first species and the constant region (which may be intact, partial or modified in accordance with the instant invention) is obtained from a second species. In some embodiments, the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "properly folded polypeptide" includes polypeptides (e.g., antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" are used interchangeably. These terms refer to the joining together of two more elements or components, by whatever means including chemical conjugation or recombinant means. For example, a fusion protein can comprise a serum albumin polypeptide, such as human serum albumin, and a second polypeptide. A fusion protein can also comprise an antibody Fc region fused to a second polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, an inhibitor of cysteine degradation is a molecule that minimizes or prevents the breakdown of cysteine. Examples of inhibitors of cysteine degradation include, but are not limited to, antioxidants, organic acids, organic aldehydes, and unsaturated lipids, specifically compounds such as glutathione, pyruvate or pyruvate-containing molecules (e.g., methyl pyruvate or ethyl pyruvate), glyceraldehyde, glyoxylic acid, or citrate. In certain embodiments, antioxidants have one or more free thiol groups. Exemplary antioxidants include, but are not limited to glutathione, penicillamine, N-acetyl-cysteine, ascorbic acid, lipoic acid, carotenes, alpha-tocopherol, and ubiquinol. The most common organic acids are the carboxylic acids, although sulfonic acids can also be used. Examples of organic acids include, but are not limited to, lactic acid, formic acid, citric acid, oxalic acid, and uric acid. Examples of organic aldehydes include, but are not limited to methanal (formaldehyde), ethanal (acetaldehyde), propanal (propionaldehyde), and butanal (butyraldehyde). Unsaturated lipids are lipids or fatty acids that contain one or more carbon-carbon double bonds in the lipid chain. Useful unsaturated lipids that can be used to inhibit cysteine degradation include, but are not limited to, linoleic acid, linolenic acid, stearic acid, arachidonic acid, palmitic acid, docosahexaenoic acid, oleic acid, myristoleic acid, palmitoleic acid, elaidic acid, erucic acid, and vaccenic acid.

The concentration in which an inhibitor of cysteine degradation is capable of reducing trisulfide formation can vary depending on the inhibitor chosen. Generally, the inhibitor will included in the culture medium at a concentration of about 50 µM to about 500 mM. In certain embodiments the inhibitor is added at a concentration of about 100 µM to about 100 mM or at a concentration of about 1 mM to 100 mM or at a concentration of about 5 mM to about 50 mM or at a concentration of about 5 mM to about 30 mM or at a concentration of about 10 mM to about 20 mM or at a concentration of about 15 mM to about 20 mM. In some embodiments, the ratio of the concentration of the inhibitor to the concentration of cysteine present (e.g., in a cell culture medium) can be from about 100:1 to about 1:10, about 20:1 to 1:10, or about 10:1 to 1:10. In some embodiments, the ratio of the concentration of the inhibitor to the concentration of cysteine can be from about 5:1 to about 1:10. In some embodiments, the ratio of the concentration of the inhibitor to the concentration of cysteine can be from about 5:1 to about 1:5, 5:1 to 1:4, 5:1 to 1:3, or 5:1 to 1:2.

As used herein, the terms "treat" or "treatment" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of a binding molecule" and "an animal in need of treatment" includes subjects, such as mammalian subjects, that would benefit from administration of a binding molecule used, e.g., for detection of an antigen recognized by a binding molecule (e.g., for a diagnostic procedure) and/or from treatment, i.e., palliation or prevention of a disease such as cancer, with a binding molecule which specifically binds a given target protein. As described in more detail herein, the binding molecule can be used in unconjugated form or can be conjugated, e.g., to a drug, prodrug, or an isotope.

II. Trisulfide Bonds

"Trisulfide bonds" are generated by the insertion of an additional sulfur atom into a disulfide bond, thereby resulting in the covalent bonding of three consecutive sulfur atoms. Trisulfide bonds and methods of preventing and removing trisulfide bonds have been discussed in International Publication No. WO 2011/041721 and U.S. Provisional Application Nos. 61/485,973 (filed May 13, 2011) and 61/617,529 (filed Mar. 29, 2012), each of which is herein incorporated by reference in its entirety. Trisulfide bonds can form between cysteine residues in proteins and can form intramolecularly (i.e., between two cysteines in the same protein) or intermolecularly (i.e. between two cysteines in separate proteins). In the case of antibodies, such as IgG1 antibodies, two intermolecular disulfide bonds link the heavy chains together and an intermolecular disulfide bonds also links each of the heavy and light chains. Similarly, IgG2 molecules contain three intermolecular disulfide bonds that link the heavy chains, and IgG3 molecules contain 6-16 intermolecular disulfide bonds that link the heavy chains. Trisulfide modifications can occur at either of these disulfide linkages, but occur more frequently at the heavy-light (HL) link than at the heavy-heavy (HH) link.

In some embodiments, trisulfide bonds decrease storage stability. In other embodiments, trisulfide bonds increase protein aggregation. In still other embodiments, trisulfide bonds increase protein oxidation, such as increasing methionine oxidation, potentially resulting in disassociation of antibody polypeptide chains (e.g. H-L and/or H-H chains).

The presence of trisulfide bonds can be detected using any of a number of methods, including methods described herein and methods known and available now or in the future to those of skill in the art. For example, trisulfide bonds can be detected using peptide mapping and can be detected based on an increase in mass of the intact protein due to an extra sulfur atom (32 Da). Trisulfide bonds can be detected using mass spectrum, or by high pressure liquid chromatography and mass spectrometry (peptide mapping utilizing a LC-MS system). An informative and quantitative analysis can be achieved through peptide mapping wherein select peptides derived from the intact molecule, including those containing sulfide bonds, are analyzed by LC-MS. In addition, trisulfide bonds can also be detected indirectly, e.g. by assessing molecular folding or thermal stability.

As described in more detail herein, the presence of trisulfide bonds in antibodies can be detected or identified as a result of increased sensitivity to heat treatment, for example as demonstrated by an increased level of fragmentation following sample preparation for non-reducing electrophoresis.

In some embodiments, the heat treatment can be at a temperature of at least about 40° C., at least about 50° C., at least about 60° C., at least about 70° C., at least about 80° C., at least about 90° C., at least about 95° C., or at least about 100° C. In some embodiments, the heat treatment can be at a temperature of about 40° C., about 50° C., about 60° C., about 70° C., about 80° C., about 90° C., or about 100° C. In some embodiments, the heat treatment can be at a temperature of less than about 120° C. In some embodiments, the heat treatment can be a temperature of about 60° C. to about 100° C.

According to the methods described herein, the heat treatment can be performed in the presence of an alkylating agent, such as n-ethyl maleimide (NEM) or iodoacetamide. The concentration of the alkylating agent such as NEM or iodoacetamide can be about 0.5 mM, about 1 mM, about 2 mM, about 3 mM, about 4 mM, about 5 mM, about 6 mM, about 7 mM, about 8 mM, about 9 mM, about 10 mM, or about 15 mM. The concentration of the alkylating agent such as NEM or iodoacetamide can also be from about 0.5 mM to about 15 mM, from about 1.0 mM, to about 15 mM, from about 0.5 mM to about 10 mM, or from about 1.0 mM to about 10 mM.

According to the methods described herein, the heat treatment can last for a variable period of time. For example, the protein can be heated for about 30 seconds, about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, or about 30 minutes. In some embodiments, the protein is heated from about 30 seconds to about 10 minutes.

In one particular embodiment described herein, the protein is heated for about 5 minutes at a temperature of about 100° C. in the presence of about 5 mM NEM.

According to the methods described herein, the non-reducing electrophoresis can be, for example, capillary electrophoresis, microfluidic chip electrophoresis (e.g. LC-90 assay), or polyacrylamide gel electrophoresis.

The quantity of trisulfide bonds can be reported in several different ways. For example, the "percentage of trisulfide bonds" present in a sample could represent the number of trisulfide bonds among the total number of all sulfide bonds present (i.e., disulfide and trisulfide bonds). However, unless otherwise stated, trisulfide bonds are reported herein as the percentage of proteins in a sample that contain at least one trisulfide bond. Thus, if only one protein in a sample of 100 proteins contains a single trisulfide bond, as defined herein, 1% of the protein in the sample contains trisulfide bonds. Similarly, if only two proteins in a sample of 100 proteins each contain one or more trisulfide bonds, as defined herein, 2% of the proteins in the sample contain trisulfide bonds. Moreover, if only one protein in a sample of 100 proteins contains 5 trisulfide bonds, as defined herein, 1% of the protein in the sample contains trisulfide bonds (i.e., one trisulfide bond-containing protein in a sample of 100 proteins).

According to the methods described herein at least 1, at least 5, at least 6, at least 7, at least 8, at least 9, at least 10, at least 15, at least 20, at least 30, at least 40, at least 50, at least 60, or at least 70 percent of the proteins in a sample can contain trisulfide bonds. In another embodiment, from about 5 to about 50, from about 5 to about 30, from about 5 to about 20, or from about 5 to about 15 percent of proteins in a sample can contain trisulfide bonds. In another embodiment, from about 10 to about 50, from about 10 to about 30, from about 10 to about 20, or from about 10 to about 15 percent of the proteins in a protein sample can contain trisulfide bonds.

In addition, it can be useful to determine the percentage of proteins containing trisulfide bonds in a sample after exposing the sample of proteins to free cysteine to determine the efficacy of the conversion of trisulfide bonds to disulfide bonds. Thus, for example, in some embodiments, after exposure to free cysteine, less than about 10, less than about 5, less than about 3, less than about 2, or less than about 1 percent of proteins in the sample contain trisulfide bonds.

The number of trisulfide bonds in a sample can be decreased according to the methods described herein. This decrease can be the result of conversion of trisulfide bonds to disulfide bonds and/or in the elimination of both trisulfide and disulfide bonds. Thus, in some embodiments the percentage of proteins containing trisulfide bonds in a sample is decreased by at least about 25%, at least about 50%, at least about 60%, at least about 70%, at least about 80%, at least about 85%, at least about 90%, at least about 95%, or about 100%. In addition, in some embodiments of the methods described herein, the percentage of proteins containing trisulfide bonds converted to disulfide bonds is at least about 25%, at least about 50%, at least about 60%, at least about 70%, at least about 80%, at least about 85%, at least about 90%, at least about 95%, or about 100%.

In some embodiments, subsequent to exposing proteins to a solution comprising a reducing agent, less than about 10%, about 5%, or about 1% of the proteins contain trisulfide bonds.

In some embodiments, the methods herein provide compositions of antibodies or fragments thereof wherein about Y % to about Z % of the antibodies or fragments thereof in the composition comprise one or more trisulfide bonds, wherein Y % and Z % are any range of values selected from the group of values represented in following table, as indicated by "Y/Z" wherein the lower "Y" value is selected from the corresponding row and the upper "Z" value is selected from the corresponding column:

| % | 0.05 | 0.1 | 0.5 | 1 | 2 | 3 | 4 | 5 | 6 | 7 | 8 | 9 | 10 | 12 | 15 |
|---|------|-----|-----|---|---|---|---|---|---|---|---|---|----|----|----|
| 0.01 | Y/Z | Y/Z | Y/Z | Y/Z | Y/Z | Y/Z | Y/Z | Y/Z | Y/Z | Y/Z | Y/Z | Y/Z | Y/Z | Y/Z | Y/Z |
| 0.05 |     | Y/Z | Y/Z | Y/Z | Y/Z | Y/Z | Y/Z | Y/Z | Y/Z | Y/Z | Y/Z | Y/Z | Y/Z | Y/Z | Y/Z |
| 0.1  |     |     | Y/Z | Y/Z | Y/Z | Y/Z | Y/Z | Y/Z | Y/Z | Y/Z | Y/Z | Y/Z | Y/Z | Y/Z | Y/Z |
| 0.5  |     |     |     | Y/Z | Y/Z | Y/Z | Y/Z | Y/Z | Y/Z | Y/Z | Y/Z | Y/Z | Y/Z | Y/Z | Y/Z |
| 1    |     |     |     |     | Y/Z | Y/Z | Y/Z | Y/Z | Y/Z | Y/Z | Y/Z | Y/Z | Y/Z | Y/Z | Y/Z |
| 2    |     |     |     |     |     | Y/Z | Y/Z | Y/Z | Y/Z | Y/Z | Y/Z | Y/Z | Y/Z | Y/Z | Y/Z |
| 3    |     |     |     |     |     |     | Y/Z | Y/Z | Y/Z | Y/Z | Y/Z | Y/Z | Y/Z | Y/Z | Y/Z |
| 4    |     |     |     |     |     |     |     | Y/Z | Y/Z | Y/Z | Y/Z | Y/Z | Y/Z | Y/Z | Y/Z |
| 5    |     |     |     |     |     |     |     |     | Y/Z | Y/Z | Y/Z | Y/Z | Y/Z | Y/Z | Y/Z |
| 6    |     |     |     |     |     |     |     |     |     | Y/Z | Y/Z | Y/Z | Y/Z | Y/Z | Y/Z |
| 7    |     |     |     |     |     |     |     |     |     |     | Y/Z | Y/Z | Y/Z | Y/Z | Y/Z |
| 8    |     |     |     |     |     |     |     |     |     |     |     | Y/Z | Y/Z | Y/Z | Y/Z |
| 9    |     |     |     |     |     |     |     |     |     |     |     |     | Y/Z | Y/Z | Y/Z |
| 10   |     |     |     |     |     |     |     |     |     |     |     |     |     | Y/Z | Y/Z |
| 12   |     |     |     |     |     |     |     |     |     |     |     |     |     |     | Y/Z |

In some embodiments, the methods herein provide compositions of antibodies or fragments thereof, wherein about Y % to about Z % of the antibodies or fragments thereof in said composition comprise only disulfide bonds, wherein Y % and Z % are any range of values selected from group of values represented in the following table, as indicated by "Y/Z" wherein the lower "Y" value is selected from the corresponding row and the upper "Z" value is selected from the corresponding column:

| %    | 65  | 70  | 75  | 80  | 85  | 90  | 95  | 97  | 98  | 99  | 99.5 | 99.9 |
|------|-----|-----|-----|-----|-----|-----|-----|-----|-----|-----|------|------|
| 60   | Y/Z | Y/Z | Y/Z | Y/Z | Y/Z | Y/Z | Y/Z | Y/Z | Y/Z | Y/Z | Y/Z  | Y/Z  |
| 65   |     | Y/Z | Y/Z | Y/Z | Y/Z | Y/Z | Y/Z | Y/Z | Y/Z | Y/Z | Y/Z  | Y/Z  |
| 70   |     |     | Y/Z | Y/Z | Y/Z | Y/Z | Y/Z | Y/Z | Y/Z | Y/Z | Y/Z  | Y/Z  |
| 75   |     |     |     | Y/Z | Y/Z | Y/Z | Y/Z | Y/Z | Y/Z | Y/Z | Y/Z  | Y/Z  |
| 80   |     |     |     |     | Y/Z | Y/Z | Y/Z | Y/Z | Y/Z | Y/Z | Y/Z  | Y/Z  |
| 85   |     |     |     |     |     | Y/Z | Y/Z | Y/Z | Y/Z | Y/Z | Y/Z  | Y/Z  |
| 90   |     |     |     |     |     |     | Y/Z | Y/Z | Y/Z | Y/Z | Y/Z  | Y/Z  |
| 95   |     |     |     |     |     |     |     | Y/Z | Y/Z | Y/Z | Y/Z  | Y/Z  |
| 97   |     |     |     |     |     |     |     |     | Y/Z | Y/Z | Y/Z  | Y/Z  |
| 98   |     |     |     |     |     |     |     |     |     | Y/Z | Y/Z  | Y/Z  |
| 99   |     |     |     |     |     |     |     |     |     |     | Y/Z  | Y/Z  |
| 99.5 |     |     |     |     |     |     |     |     |     |     |      | Y/Z  |

III. Reducing Agent Treatment

According to the methods described herein, trisulfide bonds can be reduced by (a) applying a protein sample containing trisulfide bonds to a chromatographic medium; and (b) contacting a solution comprising a reducing agent with the protein in association with the chromatographic medium.

The protein sample can be any sample containing a protein with trisulfide bonds that is amenable to application to a chromatographic medium. For example, the protein sample can be a biological sample. Thus, the sample can be isolated from a patient, a subject, or a model organism. The sample can also be isolated from a cell culture and can be, for example, a sample obtained from a cell lysate or a sample obtained from cell supernatant. In addition, the sample can be a commercially available protein preparation (such as, for example, commercially available antibody preparations).

The protein in the sample can be a recombinant protein, a synthetic protein, or a naturally occurring protein.

The chromatographic medium can be any chromatographic medium known in the art now or in the future. The chromatographic medium can be one to which the protein in the protein sample is bound, i.e. a chromatographic medium that does not operate in a flow-through mode. Binding of the protein can provide certain advantages, for example, by limiting motion of the protein and thereby preventing the formation of undesirable disulfide bonds. For example, the chromatographic medium can be an ion exchange chromatography medium, a mixed mode chromatography medium, an affinity chromatography medium, a pseudo-affinity chromatography medium. The affinity chromatography medium can be, for example a lectin chromatography medium, a metal binding chromatography medium such as a nickel chromatography medium, a GST chromatography medium, a Protein G chromatography medium, a Protein A chromatography medium, or an immunoaffinity chromatography medium. The chromatographic medium can be in the form of a column, a chromatography resin, a similar binding matrix in another format such as a 96-well format. In addition, the protein sample can be bound to a suitably modified membrane. In a particular embodiment, the chromatography medium is a protein A affinity chromatography medium. In another particular embodiment, the chromatography medium is an antibody Fc region-binding chromatography medium.

The solution comprising the reducing agent can be any solution that is compatible with the chromatography medium and desired protein function/biological activity (e.g., a solution that does not disrupt the integrity of the column or irreversibly denature or inactivate the target protein). Similarly, the reducing agent can be any reducing agent that is compatible with the chromatography medium and desired protein function/biological activity. For example, the reducing agent can be cysteine (including, for example, L-cysteine and N-acetyl cysteine), cysteine hydrochloride, cysteamine, sulfur dioxide, hydrogen sulfide, glutathione (GSH) (including, for example, L-glutathione (L-GSH), thioglycolic acid, bisulfite, ascorbic acid, sorbic acid, TCEP (tris(2-carboxyethyl)phosphine) and/or fumaric acid.

In some embodiments, the solution comprising the reducing agent further comprises additional components that decrease trisulfide bond levels. In some embodiments, the solution comprising the reducing agent further comprises an alkali metal such as sodium, lithium, potassium, rubidium, or cesium. In some embodiments, the alkali metal is sodium phosphate. For example, the solution can be a phosphate buffered saline (PBS) solution. In some embodiments, the pH of the solution comprising cysteine is a neutral pH (i.e., about 7). In some embodiments, the pH of the solution comprising cysteine is in a range from about 3 to about 9, from about 4 to about 8, from about 5 to about 7, from about 6 to about 7, from about 5 to about 9, from about 5 to about 8, and from about 6 to about 8.

According to the methods described herein, the reducing agent can be free cysteine. The concentration of free cysteine in the solution can be, for example, about 0.1 mM or more and less than about 10 mM. In some embodiments, the concentration of cysteine can be, for example, from about 0.5 mM to about 9 mM, from about 0.5 mM to about 8 mM, from about 0.5 mM to about 7 mM, from about 0.5 mM to about 6 mM, from about 0.5 mM to about 5 mM, from 0.5 mM to about 4 mM, from about 0.5 mM to about 1.0 mM, from about 0.5 mM to about 2.0 mM, from about 0.5 mM to about 3 mM, from about 0.5 mM to about 4 mM, from about 0.5 mM to about 5 mM. In some embodiments, the concentration of cysteine is from about 1.0 mM to about 9 mM, from about 1.0 mM to about 8 mM, from about 1.0 mM to about 7 mM, from about 1.0 mM to about 6 mM, from about 1.0 mM to about 5 mM, from about 1.0 mM to about 4 mM, or from about 1.0 mM to about 3 mM. In some particular embodiments, the concentration is about 1.0 mM cysteine or about 3.0 mM cysteine. In some embodiments, the cysteine is L-cysteine. In some embodiments, the cysteine is N-acetyl cysteine.

According to the methods described herein, the reducing agent can be glutathione. The concentration of glutathione in the solution can be, for example, about 0.1 mM or more and less than about 10 mM. In some embodiments, the concentration of glutathione can be, for example, from about 0.5 mM to about 9 mM, from about 0.5 mM to about 8 mM, from about 0.5 mM to about 7 mM, from about 0.5 mM to about 6 mM, from about 0.5 mM to about 5 mM, from 0.5 mM to about 4 mM, from about 0.5 mM to about 1.0 mM, from about 0.5 mM to about 2.0 mM, from about 0.5 mM to about 3 mM, from about 0.5 mM to about 4 mM, from about 0.5 mM to about 5 mM. In some embodiments, the concentration of glutathione is from about 1.0 mM to about 9 mM, from about 1.0 mM to about 8 mM, from about 1.0 mM to about 7 mM, from about 1.0 mM to about 6 mM, from about 1.0 mM to about 5 mM, from about 1.0 mM to about 4 mM, or from about 1.0 mM to about 3 mM. In some particular embodiments, the concentration is about 1.0 mM glutathione. In some embodiments, the glutathione is L-glutathione.

The solution comprising the reducing agent can be applied in a single step or in multiple steps. The solution comprising the reducing agent can be applied at a constant concentration or as a continuous or step-wise gradient of increasing or decreasing concentrations. In some embodiments, the contact time of the reducing agent with the protein sample can be controlled by selecting an appropriate column flow rate. For example, higher flow rates and shorter contact times can be used with higher concentrations of the reducing agent.

In some embodiments, the contact time is at least about 5 minutes, about 10 minutes, about 20 minutes, about 30 minutes, about 40 minutes, about 50 minutes, about 60 minutes, about 90 minutes, about 2 hours, about 3 hours, about 4 hours, or about 5 hours. In some embodiments, the contact time is less than about 24 hours, less than about 20 hours, less than about 12 hours, or less than about 6 hours. In some embodiments, the contact time is about 1 hour.

In some embodiments, the linear flow velocity is at least about 10 cm/hr, at least about 20 cm/hr, at least about 30 cm/hr, at least about 40 cm/hr, at least about 50 cm/hr, at least about 60 cm/hr, at least about 70 cm/hr, at least about 80 cm/hr, at least about 90 cm/hr, at least about 100 cm/hr, at least about 150 cm/hr, at least about 200 cm/hr, at least about 250 cm/hr, at least about 300 cm/hr, at least about 350 cm/hr, at least about 400 cm/hr, at least about 450 cm/hr, at least about 500 cm/hr, at least about 550 cm/hr. In some embodiments, the linear flow velocity is less than about 1000 cm/hr or less than about 750 cm/hr. In some embodiments, the linear flow velocity is a velocity that is compatible with large scale column purification of antibodies. In some embodiments, the linear flow velocity is about 100 cm/hr.

The application of a solution comprising the reducing agent to the protein sample in association with a chromatographic medium can be preceded by, combined with, or followed by additional wash steps. For example, a PBS wash can be applied before the solution comprising the reducing agent is applied to the chromatographic medium. The wash can be used, for example, to clear impurities. A wash with a high salt buffer solution can also be used to promote the clearance of impurities, for example, after the solution comprising the reducing agent is applied to the chromatographic medium. A high salt wash can also be combined with the reducing agent wash, thereby reducing the total number of washes required. Additionally and/or alternatively, a reducing-agent-free wash can be applied after the reducing agent wash to remove the reducing agent from the protein while the protein is still on the column. Additionally and/or alternatively, a low salt concentration wash can be applied to promote efficient elution during a subsequent elution step.

After the application of a solution comprising a reducing agent to the chromatographic medium, and optionally additional wash steps, the protein can be eluted from the chromatographic medium. Elution can be performed using any technique known in the art, for example, when using a Protein A chromatographic medium elution can be performed by applying a low pH solution (e.g., a pH of about 3.5). The pH of the eluted sample can then be adjusted to a more neutral pH (e.g., a pH of about 5 to 9, pH of about 6 to 8, or pH of about 7) using a basic solution.

IV. Treatment with Inhibitor of Cysteine Degradation

According to the methods described herein, trisulfide bonds can be reduced using inhibitors of cysteine degradation. For example, culturing cells expressing proteins in the presence of an inhibitor of cysteine degradation can reduce trisulfide bonds.

In some embodiments, the solution comprising the inhibitor of cysteine degradation further is a cell-culture medium. In some embodiments, the cell-culture medium is a common cell-culture medium, for example, Iscove's Modified Dulbecco's Medium (IMDM) or Dulbecco's Modified Eagle Medium (DMEM). In some embodiments, the cell-culture medium further comprises glucose. In some embodiments, the cell-culture medium comprises cysteine. In some embodiments, a medium can contain glucose and cysteine. In some embodiments, a medium can contain a solution of amino acids and cysteine.

In some embodiments, the ratio of the concentration of the inhibitor to the concentration of cysteine present in a cell culture medium can be, for example, from about 100:1 to about 1:10, about 20:1 to 1:10, or about 10:1 to 1:10. In some embodiments, the ratio of the concentration of the inhibitor to the concentration of cysteine can be from about 5:1 to about 1:10. In some embodiments, the ratio is about 1:1. In some embodiments, the ratio of the concentration of the inhibitor to the concentration of cysteine can be from about 5:1 to about 1:5, 5:1 to 1:4, 5:1 to 1:3, or 5:1 to 1:2.

According to the methods described herein, the inhibitor of cysteine degradation can be pyruvate or pyruvate-containing molecules. The concentration of pyruvate or pyruvate-containing molecules can be, for example, about 50 µM to about 500 mM. In some embodiments, the concentration of pyruvate or pyruvate-containing molecules can be, for example, from about 1 mM to about 250 mM, from about 1 mM to about 100 mM, from about 1 mM to about 50 mM, from about 1 mM to about 30 mM, from about 1 mM to about 25 mM, or from about 1 mM to about 20 mM. In some embodiments, the concentration of pyruvate or pyruvate-containing molecules can be, for example, from about 5 mM to about 250 mM, from about 5 mM to about 100 mM, from about 5 mM to about 50 mM, from about 5 mM to about 30 mM, from about 5 mM to about 25 mM, or from about 5 mM to about 20 mM. In some embodiments, the concentration of pyruvate or pyruvate-containing molecules can be, for example, from about 10 mM to about 250 mM, from about 10 mM to about 100 mM, from about 10 mM to about 50 mM, from about 10 mM to about 30 mM, from about 10 mM to about 25 mM, or from about 10 mM to about 20 mM. In some embodiments, the concentration of pyruvate or pyruvate-containing molecules can be, for example, from about 15 mM to about 250 mM, from about 15 mM to about 100 mM, from about 15 mM to about 50 mM, from about 15 mM to about 30 mM, from about 15 mM to about 25 mM, or from about 15 mM to about 20 mM. In some embodiments, the pyruvate-containing molecule can be, for example, methyl pyruvate or ethyl pyruvate. In some embodiments, the inhibitor of cysteine degradation is pyruvate.

According to the methods described herein, the inhibitor of cysteine degradation can be glyceraldehyde. The concentration of glyceraldehyde can be, for example, about 50 µM to about 500 mM. In some embodiments, the concentration of glyceraldehyde can be, for example, from about 1 mM to about 250 mM, from about 1 mM to about 100 mM, from about 1 mM to about 50 mM, from about 1 mM to about 30 mM, from about 1 mM to about 25 mM, or from about 1 mM to about 20 mM. In some embodiments, the concentration of glyceraldehyde can be, for example, from about 5 mM to about 250 mM, from about 5 mM to about 100 mM, from about 5 mM to about 50 mM, from about 5 mM to about 30 mM, from about 5 mM to about 25 mM, or from about 5 mM to about 20 mM. In some embodiments, the concentration of glyceraldehyde can be, for example, from about 10 mM to about 250 mM, from about 10 mM to about 100 mM, from about 10 mM to about 50 mM, from about 10 mM to about 30 mM, from about 10 mM to about 25 mM, or from about 10 mM to about 20 mM. In some embodiments, the concentration of glyceraldehyde can be, for example, from about 15 mM to about 250 mM, from about 15 mM to about 100 mM, from about 15 mM to about 50 mM, from about 15 mM to about 30 mM, from about 15 mM to about 25 mM, or from about 15 mM to about 20 mM.

According to the methods described herein, the inhibitor of cysteine degradation can be glyoxylic acid. The concentration of glyoxylic acid can be, for example, about 50 µM to about 500 mM. In some embodiments, the concentration of glyoxylic acid can be, for example, from about 1 mM to about 250 mM, from about 1 mM to about 100 mM, from about 1 mM to about 50 mM, from about 1 mM to about 30 mM, from about 1 mM to about 25 mM, or from about 1 mM to about 20 mM. In some embodiments, the concentration of glyoxylic acid can be, for example, from about 5 mM to about 250 mM, from about 5 mM to about 100 mM, from about 5 mM to about 50 mM, from about 5 mM to about 30 mM, from about 5 mM to about 25 mM, or from about 5 mM to about 20 mM. In some embodiments, the concentration of glyoxylic acid can be, for example, from about 10 mM to about 250 mM, from about 10 mM to about 100 mM, from about 10 mM to about 50 mM, from about 10 mM to about 30 mM, from about 10 mM to about 25 mM, or from about 10 mM to about 20 mM. In some embodiments, the concentration of glyoxylic acid can be, for example, from about 15 mM to about 250 mM, from about 15 mM to about 100 mM, from about 15 mM to about 50 mM, from about 15 mM to about 30 mM, from about 15 mM to about 25 mM, or from about 15 mM to about 20 mM.

In some embodiments, protein trisulfide bond formation is prevented, inhibited or curtailed via monitoring and/or manipulating the concentration of cysteine and/or cystine present in a cell culture media at or below a threshold level. For example, in order to decrease or maintain low cysteine and/or cystine levels, methionine can replace cysteine and/or cystine in a nutrient feed. In some embodiments, the total amount of feed can be lowered in order to reduce cysteine and/or cystine levels. The threshold level can be, for example, about 150 µM, about 125 µM, about 100 µM, about 90 µM, about 80 µM, about 70 µM, about 60 µM, about 50 µM, about 40 µM, about 30 µM, or about 20 µM. The threshold level can be, for example, about 10 mM, about 9 mM, about 8 mM, about 7 mM, about 6 mM, about 5 mM, about 4 mM, about 3 mM, about 2 mM, about 1 mM, about 0.9 mM, about 0.8 mM, about 0.7 mM, about 0.6 mM, about 0.5 mM, about 0.4 mM, about 0.3 mM, about 0.2 mM, or about 0.1 mM.

In some embodiments, protein trisulfide bond formation is prevented, inhibited or curtailed via monitoring and/or manipulating the concentration of hydrogen sulfide ($H_2S$) at or below a threshold level. The threshold level can be, for example, about 10 parts per million (ppm), about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, or about 0.1 ppm. In some embodiments, the threshold levels is about 500 parts per billion (ppb), about 250 ppb, about 200 ppb about 100 ppb, or about 50 ppb. In some embodiments, the use of an inhibitor of cysteine degradation maintains the $H_2S$ concentration at a level of below about 10 ppm, about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, or about 0.1 ppm. In some embodiments, the use of an inhibitor of cysteine degradation maintains the $H_2S$ concentration at a level of below about 500 ppb, about 250 ppb, about 200 ppb about 100 ppb, or about 50 ppb In some embodiments, addition of inhibitor of cysteine degradation reduces release of hydrogen sulfide by at least 55%, 60%, 65%, 70%, 75%, or 80% compared to absence of inhibitor.

V. Cell Culture

According to the methods described herein, the trisulfide bond-containing protein can be a protein that is produced in a cell culture. The protein produced by the cell culture can be a recombinant protein or a protein naturally expressed by the cells grown in the culture. The protein can be an intracellular protein, a transmembrane protein, or a secreted protein.

In some particular embodiments, the protein is an antibody. For example, the antibody can be an antibody that binds to LINGO-1. The antibody can also be an antibody that binds to human LINGO-1. In some embodiments the anti-LINGO-1 antibody is selected from the group consisting of Li13, Li33, Li62, Li81, and Li113 and chimeric or humanized versions thereof. In some embodiments, the anti-LINGO-1 antibody is a variant of Li13, Li33, Li62, Li81, or Li113. For example, in the some embodiments, the anti-LINGO-1 antibody is Li81 M96L or Li81 M96F, each of which contain an amino acid substitution in methionine 96 of the light chain of the Li81 antibody. "Mab1" and "mAb-A" as referred to in the examples below are the anti-LINGO-1 antibody Li81.

Li13 and Li33 are monoclonal antibody Fab fragments that were identified and isolated from phage display libraries as described in Hoet et al., *Nat. Biotech.* 23:344-348 (2005); Rauchenberger, et al., *J. Biol. Chem.* 278:194-205 (2003); and Knappik, et al., *J. Mol. Biol.* 296:57-86 (2000), all of which are incorporated herein by reference in their entireties. In these experiments, the MorphoSys Fab-phage display library HuCAL® GOLD, which comprises humanized synthetic antibody variable regions was screened against recombinant human soluble LINGO-1-Fc protein by standard ELISA AND IHC screening methods. Fab-phages that specifically bound to LINGO-1 were purified and characterized. Li13 and Li33 are described in more detail in International Published Application WO 2007/008547, which is incorporated herein by reference in its entirety.

Antibody Li81 is derived from Li13 and Li33. It includes the Li13 light chain and an affinity matured heavy chain. Li81 is described in more detail in International Published Application WO 2008/086006, which is incorporated herein by reference in its entirety. Li81 M96L and Li81 M96F are described in WO 2010/005570, which is incorporated herein by reference in its entirety.

Li62 is derived from Li33. It includes the Li33 heavy chain and a light chain that was identified in a library screen. Li113 was identified by isolated targeted phage display. It includes the Li62 light chain as well as the Li62 VH CDR1 and CDR2 sequences, but has alterations in the VH CDR3 sequence. Li62 and Li113 are described in International Application No. PCT/US2009/003999 (published as WO 2010/005570), which is incorporated herein by reference in its entirety.

The VH sequences of Li13, Li33, Li62, Li81, and Li113 are shown in Table 1 below.

TABLE 1

LINGO-1 Antibody VH Sequences

| Antibody | VH SEQUENCE | VH CDR 1 | VH CDR2 | VH CDR3 |
|---|---|---|---|---|
| Li13 | EVQLLESGGGLVQPGGSLRLSCAASGF TFSHYEMYWVRQAPGKGLEWVSRIVS SGGFTKYADSVKGRFTISRDNSKNTLY LQMNSLRAEDTAVYYCATEGDNDAFD IWGQGTTVTVSS (SEQ ID NO: 1) | HYEMY (SEQ ID NO: 2) | RIVSSGG FTKYAD SVKG (SEQ ID NO: 3) | EGDND AFDI (SEQ ID NO: 4) |
| Li33 | EVQLLESGGGLVQPGGSLRLSCAASGF TFSIYPMFWVRQAPGKGLEWVSWIGPS GGITKYADSVKGRFTISRDNSKNTLYL QMNSLRAEDTATYYCAREGHNDWYF DLWGRGTLVTVSS (SEQ ID NO: 97) | IYPMF (SEQ ID NO: 5) | WIGPSG GITKYA DSVKG (SEQ ID NO: 6) | EGHND WYFDL (SEQ ID NO: 7) |
| Li62 | EVQLLESGGGLVQPGGSLRLSCAASGF TFSIYPMFWVRQAPGKGLEWVSWIGPS GGITKYADSVKGRFTISRDNSKNTLYL QMNSLRAEDTATYYCAREGHNDWYF DLWGRGTLVTVSS (SEQ ID NO: 8) | IYPMF (SEQ ID NO: 9) | WIGPSG GITKYA DSVKG (SEQ ID NO: 10) | EGHND WYFDL (SEQ ID NO: 11) |
| Li81 | EVQLLESGGGLVQPGGSLRLSCAASGF TFSAYEMKWVRQAPGKGLEWVSVIGP SGGFTFYADSVKGRFTISRDNSKNTLY LQMNSLRAEDTAVYYCATEGDNDAFD IWGQGTTVTVSS (SEQ ID NO: 12) | AYEMK (SEQ ID NO: 13) | VIGPSGG FTFYADS VKG (SEQ ID NO: 14) | EGDND AFDI (SEQ ID NO: 15) |
| Li113 | EVQLLESGGGLVQPGGSLRLSCAASGF TFSIYPMFWVRQAPGKGLEWVSWIGPS GGITKYADSVKGRFTISRDNSKNTLYL QMNSLRAEDTATYYCAREGTYDWYL DLWGRGTLVTVSS (SEQ ID NO: 16) | IYPMF (SEQ ID NO: 17) | WIGPSG GITKYA DSVKG (SEQ ID NO: 18) | EGTYD WYLDL (SEQ ID NO: 19) |

The VL sequences of Li13, Li33, Li62, Li81, Li113, Li81 M96L, and Li81 M96F are shown in the Table 2 below.

TABLE 2

LINGO-1 Antibody VL Sequences

| Antibody | VL SEQUENCE | VL CDR1 | VL CDR2 | VL CDR3 |
|---|---|---|---|---|
| Li13 | DIQMTQSPATLSLSPGERATLSCRAS QSVSSYLAWYQQKPGQAPRLLIYDA SNRATGIPARFSGSGSGTDFTLTISSLE PEDFAVYYCQQRSNWPMYTFGQGT KLEIK (SEQ ID NO: 20) | RASQS VSSYL A (SEQ ID NO: 21) | DASNR AT (SEQ ID NO: 22) | QQRSN WPMYT (SEQ ID NO: 23) |
| Li33 | DIQMTQSPGTLSLSPGERATLSCRAS QSVSSYLAWYQQKPGQAPRLLIYDA SNRATGIPARFSGSGSGTEFTLTISSLQ SEDFAVYYCQQYDKWPLTFGGGTK VEIK (SEQ ID NO: 24) | RASQS VSSYL A (SEQ ID NO: 25) | DASNR AT (SEQ ID NO: 26) | QQYDK WPLT (SEQ ID NO: 27) |
| Li62 | DIQMTQSPSFLSASVGDSVAITCRAS QDISRYLAWYQQRPGKAPKLLIYDA SNLQTGVPSRFSGSGSGTDFTFTITSL | RASQD ISRYL A (SEQ | DASNL QT (SEQ ID | QQYDT LHPS (SEQ ID |

TABLE 2-continued

LINGO-1 Antibody VL Sequences

| Antibody | VL SEQUENCE | VL CDR1 | VL CDR2 | VL CDR3 |
|---|---|---|---|---|
| | QPEDFGTYYCQQYDTLHPSFGPGTTV DIK (SEQ ID NO: 28) | ID NO: 29) | NO: 30) | NO: 31) |
| Li81 | DIQMTQSPATLSLSPGERATLSCRAS QSVSSYLAWYQQKPGQAPRLLIYDA SNRATGIPARFSGSGSGTDFTLTISSLE PEDFAVYYCQQRSNWPMYTFGQGT KLEIK (SEQ ID NO: 32) | RASQS VSSYL A (SEQ ID NO: 33) | DASNR AT (SEQ ID NO: 34) | QQRSN WPMYT (SEQ ID NO: 35) |
| Li113 | DIQMTQSPSFLSASVGDSVAITCRAS QDISRYLAWYQQRPGKAPKLLIYDA SNLQTGVPSRFSGSGSGTDFTFTITSL QPEDFGTYYCQQYDTLHPSFGPGTTV DIK (SEQ ID NO: 36) | RASQD ISRYL A (SEQ ID NO: 37) | DASNL QT (SEQ ID NO: 38) | QQYDT LHPS (SEQ ID NO: 39) |
| Li81 M96L | DIQMTQSPATLSLSPGERATLSCRAS QSVSSYLAWYQQKPGQAPRLLIYDA SNRATGIPARFSGSGSGTDFTLTISSLE PEDFAVYYCQQRSNWPLYTFGQGTK LEIK (SEQ ID NO: 93) | RASQS VSSYL A (SEQ ID NO: 98) | DASNR AT (SEQ ID NO: 100) | QQRSN WPLYT (SEQ ID NO: 94) |
| Li81 M96F | DIQMTQSPATLSLSPGERATLSCRAS QSVSSYLAWYQQKPGQAPRLLIYDA SNRATGIPARFSGSGSGTDFTLTISSLE PEDFAVYYCQQRSNWPFYTFGQGTK LEIK (SEQ ID NO: 95) | RASQS VSSYL A (SEQ ID NO: 99) | DASNR AT (SEQ ID NO: 101) | QQRSN WPFYT (SEQ ID NO: 96) |

In another example, the antibody can be an antibody that binds to Fn14. Fn14, a TWEAK receptor, is a growth factor-regulated immediate-early response gene that decreases cellular adhesion to the extracellular matrix and reduces serum-stimulated growth and migration. Meighan-Mantha et al., *J. Biol. Chem.* 274:33166-33176 (1999). In some embodiments, the anti-Fn14 antibody is selected from the group consisting of P4A8, P3G5, and P2D3 and chimeric or humanized versions thereof. Anti-Fn14 antibodies P4A8, P3G5, and P2D3 were raised in Fn14-deficient mice by administration of CHO cells expressing human surface Fn14 and boosted with Fn14-myc-His protein. These antibodies are described in more detail in International Application Number PCT/US2009/043382, filed on May 8, 2009, which is incorporated herein by reference in its entirety.

The VH sequences of P4A8, P3G5, and P2D3 antibodies are shown in Table 3 below.

TABLE 3

Fn14 Antibody VH Sequences

| Antibody | VH SEQUENCE | VH CDR1 | VH CDR2 | VH CDR3 |
|---|---|---|---|---|
| P4A8 | QVQLQQSGPEVVRPGVSVKISCKGS GYTFTDYGMHWVKQSHAKSLEWI GVISTYNGYTNYNQKFKGKATMTV DKSSSTAYMELARLTSEDSAIYYCA RAYYGNLYYAMDYWGQGTSVTVS S (SEQ ID NO: 40) | DYGMH (SEQ ID NO: 41) | VISTY NGYTN YNQKF KG (SEQ ID NO: 42) | AYYG NLYYA MDY (SEQ ID NO: 43) |
| P3G5 | QVQLQQSGPEVVRPGVSVKISCKGS GYTFTDYGIHWVKQSHAKSLEWIG VISTYNGYTNYNQKFKGKATMTVD KSSSTAYMELARLTSEDSAIYYCAR AYYGNLYYAMDYWGQGTSVTVSS (SEQ ID NO: 44) | DYGIH (SEQ ID NO: 45) | VISTY NGYTN YNQKF KG (SEQ ID NO: 46) | AYYG NLYYA MDY (SEQ ID NO: 47) |
| P2D3 | QVSLKESGPGILQPSQTLSLTCSFSG FSLSTSGMGVSWIRQPSGKGLEWLA HIYWDDDKRYNPSLKSRLTISKDTS RNQVFLKITSVDTADTATYYCARRG PDYYGYYPMDYWGQGTSVTVSS (SEQ ID NO: 48) | TSGMG VS (SEQ ID NO: 49) | HIYWD DDKRY NPSLK S (SEQ ID NO: 50) | RGPDY YGYYP MDY (SEQ ID NO: 51) |
| huP4A8 version 1 | QVQLVQSGAEVKKPGASVKVSCKG SGYTFTDYGMHWVRQAPGQGLEW MGVISTYNGYTNYNQKFKGRVTMT VDKSTSTAYMELRSLRSDDTAVYY CARAYYGNLYYAMDYWGQGTLVT VSS (SEQ ID NO: 52) | GYTFTD YGMH (SEQ ID NO: 53) | VISTY NGYTN YNQKF KG (SEQ ID NO: 54) | AYYG NLYYA MDY (SEQ ID NO: 55) |

TABLE 3-continued

Fn14 Antibody VH Sequences

| Antibody | VH SEQUENCE | VH CDR1 | VH CDR2 | VH CDR3 |
|---|---|---|---|---|
| huP4A8 version 2 | QVQLVQSGAEVKKPGASVKVSCKG SGYTFTDYGMHWVRQAPGQGLEWI GVISTYNGYTNYNQKFKGRATMTV DKSTSTAYMELRSLRSDDTAVYYC ARAYYGNLYYAMDYWGQGTLVTV SS (SEQ ID NO: 56) | GYTFTD YGMH (SEQ ID NO: 57) | VISTY NGYTN YNQKF KG (SEQ ID NO: 58) | AYYG NLYYA MDY (SEQ ID NO: 59) |

The VL sequences of P4A8, P3G5, and P2D3 antibodies are shown in Table 4 below.

TABLE 4

Fn14 Antibody VL Sequences

| Antibody | VL SEQUENCE | VL CDR1 | VL CDR2 | VL CDR3 |
|---|---|---|---|---|
| P4A8 | DIVLTQSPASLAVSLGQRATISCRAS KSVSTSSYSYMHWYQQKPGQPPKL LIKYASNLESGVPARFSGSGSGTDFI LNIHPVEEEDAATYYCQHSRELPFT FGSGTKLEIK (SEQ ID NO: 60) | RASKSV STSSYS YMH (SEQ ID NO: 61) | ASNLE S (SEQ ID NO: 62) | QHSREL PFT (SEQ ID NO: 63) |
| P3G5 | DIVLTQSPASLAVSLGQRATISCRAN KSVSTSSYSYMHWYQQKPGQPPKL LIKYASNLESGVPARFSGSGSGTDFI LNIHPVEEEDAATYYCQHSRELPFT FGSGTKLEIK (SEQ ID NO: 64) | RANKS VSTSSY SYMH (SEQ ID NO: 65) | ASNLE S (SEQ ID NO: 66) | QHSREL PFT (SEQ ID NO: 67) |
| P2D3 | DIVLTQSPASLAVSLGQRATISCRAS KSVSTSSYSYMHWYQQKPGQPPKL LIKYTSNLESGVPARFSGSGSGTDFI LNIHPVEEEDAATYYCQHSRELPWT FGGGTKLEIK (SEQ ID NO: 68) | RASKSV STSSYS YMH (SEQ ID NO: 69) | TSNLE S (SEQ ID NO: 70) | QHSREL PWT (SEQ ID NO: 71) |
| Humanized P4A8 version 1 | DIVLTQSPASLAVSLGQRATISCRAS KSVSTSSYSYMHWYQQKPGQPPKL LIKYASNLESGVPARFSGSGSGTDFS LNIHPMEEDDTAMYFCQHSRELPFT FGGGTKLEIK (SEQ ID NO: 72) | RASKSV STSSYS YMH (SEQ ID NO: 73) | YASNL ES (SEQ ID NO: 74) | QHSREL PFT (SEQ ID NO: 75) |
| Humanized P4A8 version 2 | DIVLTQSPASLAVSLGQRATISCRAS KSVSTSSYSYMHWYQQKPGQPPKL LIKYASNLESGVPARFSGSGSGTDFI LNIHPMEEDDTAMYFCQHSRELPFT FGGGTKLEIK (SEQ ID NO: 76) | RATISC RASKSV STSSYS YMH (SEQ ID NO: 77) | YASNL ES (SEQ ID NO: 78) | QHSREL PFT (SEQ ID NO: 79) |
| Humanized P4A8 version 3 | DIVLTQSPASLAVSLGQRATISCRAS KSVSTSSYSYMHWYQQKPGQPPKL LIKYASNLESGVPARFSGSGSGTDFI LNIHPMEEDDTATYYCQHSRELPFT FGGGTKLEIK (SEQ ID NO: 80) | RASKSV STSSYS YMH (SEQ ID NO: 81) | YASNL ES (SEQ ID NO: 82) | QHSREL PFT (SEQ ID NO: 83) |

Heavy and light chain sequences of humanized P4A8 antibodies are shown in Table 5 below.

TABLE 5

Chain Sequences of Chimeric and Humanized P4A8 Antibodies

| Chain Description | Sequence |
|---|---|
| Chimeric P4A8 heavy | QVQLQQSGPEVVRPGVSVKISCKGSGYTFTDYGMHWVKQSHA KSLEWIGVISTYNGYTNYNQKFKGKATMTVDKSSSTAYMELA RLTSEDSAIYYCARAYYGNLYYAMDYWGQGTSVTVSSASTKG PSVFPLAPSSKSTSGGTAALGCLVKDYFPEPVTVSWNSGALTSG VHTFPAVLQSSGLYSLSSVVTVPSSSLGTQTYICNVNHKPSNTK |

TABLE 5-continued

Chain Sequences of Chimeric and Humanized P4A8 Antibodies

| Chain Description | Sequence |
|---|---|
| | VDKKVEPKSCDKTHTCPPCPAPELLGGPSVFLFPPKPKDTLMIS<br>RTPEVTCVVVDVSHEDPEVKFNWYVDGVEVHNAKTKPREEQY<br>NSTYRVVSVLTVLHQDWLNGKEYKCKVSNKALPAPIEKTISKA<br>KGQPREPQVYTLPPSRDELTKNQVSLTCLVKGFYPSDIAVEWES<br>NGQPENNYKTTPPVLDSDGSFFLYSKLTVDKSRWQQGNVFSCS<br>VMHEALHNHYTQKSLSLSPG (SEQ ID NO: 84) |
| Chimeric<br>P4A8 light | DIVLTQSPASLAVSLGQRATISCRASKSVSTSSYSYMHWYQQKP<br>GQPPKLLIKYASNLESGVPARFSGSGSGTDFILNIHPVEEEDAAT<br>YYCQHSRELPFTFGSGTKLEIKRTVAAPSVFIFPPSDEQLKSGTA<br>SVVCLLNNFYPREAKVQWKVDNALQSGNSQESVTEQDSKDST<br>YSLSSTLTLSKADYEKHKVYACEVTHQGLSSPVTKSFNRGEC<br>(SEQ ID NO: 85) |
| Humanized<br>P4A8-IgG1<br>H1 heavy | QVQLVQSGAEVKKPGASVKVSCKGSGYTFTDYGMHWVRQAP<br>GQGLEWMGVISTYNGYTNYNQKFKGRVTMTVDKSTSTAYME<br>LRSLRSDDTAVYYCARAYYGNLYYAMDYWGQGTLVTVSSAS<br>TKGPSVFPLAPSSKSTSGGTAALGCLVKDYFPEPVTVSWNSGAL<br>TSGVHTFPAVLQSSGLYSLSSVVTVPSSSLGTQTYICNVNHKPS<br>NTKVDKKVEPKSCDKTHTCPPCPAPELLGGPSVFLFPPKPKDTL<br>MISRTPEVTCVVVDVSHEDPEVKFNWYVDGVEVHNAKTKPRE<br>EQYNSTYRVVSVLTVLHQDWLNGKEYKCKVSNKALPAPIEKTI<br>SKAKGQPREPQVYTLPPSRDELTKNQVSLTCLVKGFYPSDIAVE<br>WESNGQPENNYKTTPPVLDSDGSFFLYSKLTVDKSRWQQGNVF<br>SCSVMHEALHNHYTQKSLSLSPG (SEQ ID NO: 86) |
| Humanized<br>P4A8-IgG1<br>H2 heavy | QVQLVQSGAEVKKPGASVKVSCKGSGYTFTDYGMHWVRQAP<br>GQGLEWIGVISTYNGYTNYNQKFKGRATMTVDKSTSTAYMEL<br>RSLRSDDTAVYYCARAYYGNLYYAMDYWGQGTLVTVSSAST<br>KGPSVFPLAPSSKSTSGGTAALGCLVKDYFPEPVTVSWNSGALT<br>SGVHTFPAVLQSSGLYSLSSVVTVPSSSLGTQTYICNVNHKPSN<br>TKVDKKVEPKSCDKTHTCPPCPAPELLGGPSVFLEPPKPKDTLM<br>ISRTPEVTCVVVDVSHEDPEVKFNWYVDGVEVHNAKTKPREEQ<br>YNSTYRVVSVLTVLHQDWLNGKEYKCKVSNKALPAPIEKTISK<br>AKGQPREPQVYTLPPSRDELTKNQVSLTCLVKGFYPSDIAVEWE<br>SNGQPENNYKTTPPVLDSDGSFFLYSKLTVDKSRWQQGNVFSC<br>SVMHEALHNHYTQKSLSLSPG (SEQ ID NO: 87) |
| Humanized<br>P4A8 L1<br>kappa light | DIVLTQSPASLAVSLGQRATISCRASKSVSTSSYSYMHWYQQKP<br>GQPPKLLIKYASNLESGVPARFSGSGSGTDFSLNIHPMEEDDTA<br>MYFCQHSRELPFTFGGGTKLEIKRTVAAPSVFIFPPSDEQLKSGT<br>ASVVCLLNNFYPREAKVQWKVDNALQSGNSQESVTEQDSKDS<br>TYSLSSTLTLSKADYEKHKVYACEVTHQGLSSPVTKSFNRGEC<br>(SEQ ID NO: 88) |
| Humanized<br>P4A8 L2<br>kappa light | DIVLTQSPASLAVSLGQRATISCRASKSVSTSSYSYMHWYQQKP<br>GQPPKLLIKYASNLESGVPARFSGSGSGTDFILNIHPMEEDDTA<br>MYFCQHSRELPFTFGGGTKLEIKRTVAAPSVFIFPPSDEQLKSGT<br>ASVVCLLNNFYPREAKVQWKVDNALQSGNSQESVTEQDSKDS<br>TYSLSSTLTLSKADYEKHKVYACEVTHQGLSSPVTKSFNRGEC<br>(SEQ ID NO: 89) |
| Humanized<br>P4A8 L3<br>kappa light | DIVLTQSPASLAVSLGQRATISCRASKSVSTSSYSYMHWYQQKP<br>GQPPKLLIKYASNLESGVPARFSGSGSGTDFILNIHPMEEDDTAT<br>YYCQHSRELPFTEGGGTKLEIKRTVAAPSVFIFPPSDEQLKSGTA<br>SVVCLLNNFYPREAKVQWKVDNALQSGNSQESVTEQDSKDST<br>YSLSSTLTLSKADYEKHKVYACEVTHQGLSSPVTKSFNRGEC<br>(SEQ ID NO: 90) |
| Humanized<br>P4A8-IgG4<br>H1 heavy<br>agly<br>S228P<br>T299A | QVQLVQSGAEVKKPGASVKVSCKGSGYTFTDYGMHWVRQAP<br>GQGLEWMGVISTYNGYTNYNQKFKGRVTMTVDKSTSTAYME<br>LRSLRSDDTAVYYCARAYYGNLYYAMDYWGQGTLVTVSSAS<br>TKGPSVFPLAPCSRSTSESTAALGCLVKDYFPEPVTVSWNSGAL<br>TSGVHTFPAVLQSSGLYSLSSVVTVPSSSLGTKTYTCNVDHKPS<br>NTKVDKRVESKYGPPCPPCPAPEFLGGPSVFLFPPKPKDTLMISR<br>TPEVTCVVVDVSQEDPEVQFNWYVDGVEVHNAKTKPREEQFN<br>SAYRVVSVLTVLHQDWLNGKEYKCKVSNKGLPSSIEKTISKAK<br>GQPREPQVYTLPPSQEEMTKNQVSLTCLVKGFYPSDIAVEWES<br>NGQPENNYKTTPPVLDSDGSFFLYSRLTVDKSRWQEGNVFSCS<br>VMHEALHNHYTQKSLSLSLG (SEQ ID NO: 91) |
| Humanized<br>P4A8-IgG1<br>H1 heavy<br>agly | QVQLVQSGAEVKKPGASVKVSCKGSGYTFTDYGMHWVRQAP<br>GQGLEWMGVISTYNGYTNYNQKFKGRVTMTVDKSTSTAYME<br>LRSLRSDDTAVYYCARAYYGNLYYAMDYWGQGTLVTVSSAS<br>TKGPSVFPLAPSSKSTSGGTAALGCLVKDYFPEPVTVSWNSGAL |

TABLE 5-continued

Chain Sequences of Chimeric and Humanized P4A8 Antibodies

| Chain Description | Sequence |
|---|---|
| T299A | TSGVHTFPAVLQSSGLYSLSSVVTVPSSSLGTQTYICNVNHKPS NTKVDKKVEPKSCDKTHTCPPCPAPELLGGPSVFLFPPKPKDTL MISRTPEVTCVVVDVSHEDPEVKFNWYVDGVEVHNAKTKPRE EQYNSAYRVVSVLTVLHQDWLNGKEYKCKVSNKALPAPIEKTI SKAKGQPREPQVYTLPPSRDELTKNQVSLTCLVKGFYPSDIAVE WESNGQPENNYKTTPPVLDSDGSFFLYSKLTVDKSRWQQGNVF SCSVMHEALHNHYTQKSLSLSPG (SEQ ID NO:92) |

The cell culture can comprise, for example, bacterial cells, yeast cells or mammalian cells. Cell types that can be used according to the present methods include any mammalian cells that are capable of growing in culture, for example, CHO (Chinese Hamster Ovary) (including CHO-K1, CHO DG44, and CHO DUXB11), VERO, HeLa, (human cervical carcinoma), CVI (monkey kidney line), (including COS and COS-7), BHK (baby hamster kidney), MDCK, C127, PC12, HEK-293 (including HEK-293T and HEK-293E), PER C6, NSO, WI38, R1610 (Chinese hamster fibroblast) BALBC/ 3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney) cells. In some particular embodiments, the cells are CHO cells or a derivative thereof.

In some embodiments, protein trisulfide bond formation is prevented, inhibited or curtailed via monitoring and manipulating the quantity and/or rate of nutrient feed, amino acid, or other nutrient supplements provided to a cell culture during a bioreactor culture run.

Optimal cell culture media compositions vary according to the type of cell culture being propagated. In some embodiments, the nutrient media is a commercially available media. In some embodiments, the nutrient media contains e.g., inorganic salts, carbohydrates (e.g., sugars such as glucose, galactose, maltose or fructose), amino acids, vitamins (e.g., B group vitamins (e.g., B12), vitamin A vitamin E, riboflavin, thiamine and biotin), fatty acids and lipids (e.g., cholesterol and steroids), proteins and peptides (e.g., albumin, transferrin, fibronectin and fetuin), serum (e.g., compositions comprising albumins, growth factors and growth inhibitors, such as, fetal bovine serum, newborn calf serum and horse serum), trace elements (e.g., zinc, copper, selenium and tricarboxylic acid intermediates), hydrolysates (hydrolyzed proteins derived from plant or animal sources), and combinations thereof. Examples of nutrient medias include, but are not limited to, basal media (e.g., MEM, DMEM, GMEM), complex media (RPMI 1640, Iscoves DMEM, Leibovitz L-15, Leibovitz L-15, TC 100), serum free media (e.g., CHO, Ham F10 and derivatives, Ham F12, DMEM/F12). Common buffers found in nutrient media include PBS, Hanks BSS, Earles salts, DPBS, HBSS, and EBSS. Media for culturing mammalian cells are well known in the art and are available from, e.g., Sigma-Aldrich Corporation (St. Louis, Mo.), HyClone (Logan, Utah), Invitrogen Corporation (Carlsbad, Calif.), Cambrex Corporation (E. Rutherford, N.J.), JRH Biosciences (Lenexa, Kans.), Irvine Scientific (Santa Ana, Calif.), and others. Other components found in nutrient media can include ascorbate, citrate, cysteine/cystine, glutamine, folic acid, glutathione, linoleic acid, linolenic acid, lipoic acid, oleic acid, palmitic acid, pyridoxal/pyridoxine, riboflavin, selenium, thiamine, and transferrin. In some embodiments the nutrient media is serum-free media, a protein-free media, or a chemically defined media. One of skill in the art will recognize that there are modifications to nutrient media which would fall within the scope of this invention.

In some embodiments, protein trisulfide bond formation is prevented, inhibited or curtailed via monitoring and/or manipulating the concentration of cysteine and/or cystine present in a cell culture media at or below a threshold level. For example, in order to decrease or maintain low cysteine and/or cystine levels, methionine can replace cysteine and/or cystine in a nutrient feed. In some embodiments, the total amount of feed can be lowered in order to reduce cysteine and/or cystine levels. The threshold level can be, for example about 150 µM, about 125 µM, about 100 µM, about 90 µM, about 80 µM, about 70 µM, about 60 µM, about 50 µM, about 40 µM, about 30 µM, or about 20 µM.

In other embodiments, protein trisulfide bond formation is prevented, inhibited or curtailed via monitoring and/or manipulating the concentration of hydrogen sulfide ($H_2S$), sodium sulfide, and/or sodium hydrogen sulfide at or below a threshold level. In some embodiments a reactant, scavenging molecule, or "sponge" can be introduced into the cell culture medium. A "sponge" as used herein, is a molecule, compound, or material that can reduce, eliminate, or inhibit the ability of sulfur or sulfur-containing compounds to form trisulfide bonds. For example, sodium sulfite can be introduced to react with and eliminate $H_2S$. The threshold level can be, for example, about 10 mM, about 9 mM, about 8 mM, about 7 mM, about 6 mM, about 5 mM, about 4 mM, about 3 mM, about 2 mM, about 1 mM, about 0.9 mM, about 0.8 mM, about 0.7 mM, about 0.6 mM, about 0.5 mM, about 0.4 mM, about 0.3 mM, about 0.2 mM, or about 0.1 mM.

In some embodiments, protein trisulfide bond formation is prevented, inhibited, or curtailed by harvesting the conditioned cell culture media from a cell culture during a particular phase of cell growth. Typical cell culture growth curves include inoculation of nutrient media with the starter cells followed by lag phase growth. The lag phase is followed by log phase growth of the culture, ultimately resulting in a plateau phase. As used herein, the term "bioreactor run" can include one or more of the lag phase, log phase, or plateau phase growth periods during a cell culture cycle. Thus, in some embodiments, the protein samples are obtained from cell culture during maximum growth phase in order to minimize formation or accumulation trisulfide bonds. In some embodiments, the cell culture is harvested when the cell culture is at approximately maximum cell density. In another embodiment, protein samples are obtained from cell culture at a time when protein production, e.g. recombinant protein production, is maximal. For example, in some embodiments, harvest occurs on day 13 of a bioreactor run. In some embodiments, the cell culture is harvested prior to the peak induction of trisulfide bond formation.

In some embodiments, protein trisulfide bond formation is prevented, inhibited or curtailed via temporarily or constantly growing the cell culture at a preferred temperature. In some embodiments, the temperature is maintained at a temperature of above 35° C. In other words, the temperature can be maintained at a steady temperature throughout the culture, or the temperature can be shifted. For example, the cell culture can be maintained at about 35° C. throughout the culturing process. In addition, the cell culture can be grown at 35° C. but shifted to a lower temperature, e.g., a temperature of about 32° C. The temperature shift can occur, for example, 1, 2, 3, 4, or 5 days before harvesting the culture. For example, if harvest occurs on day 13 of a bioreactor process, the temperature shift can occur, for example, at day 9 of the bioreactor process. In order to compensate for slower growth, and associated excess feed at lower temperatures, a decrease in temperature can be performed in combination with a reduction in feed.

Protein samples can be obtained from the cell cultures using methods known to those of skill in the art. For example, methods such as freeze-thaw cycling, sonication, mechanical disruption, or use of cell lysing agents can be used to disrupt cells to obtain protein samples. Where proteins are secreted by cells in the cell culture, a protein sample can easily be recovered from the supernatant. Protein samples can also be obtained using methods such as spheroplast preparation and lysis, cell disruption using glass beads, and cell disruption using liquid nitrogen, for example.

Protein samples can also be further processed or purified before the cysteine column wash. For example, samples can be subjected to ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, protein refolding steps and/or high performance liquid chromatography (HPLC) either before or after the cysteine column wash.

VI. Compositions Comprising Proteins with Reduced Trisulfides and Uses Thereof Proteins that have been treated according to the methods described herein to prevent and/or eliminate trisulfide bonds can be prepared for subsequent use in diagnostic assays, immunoassays and/or pharmaceutical compositions.

In some embodiments, the protein, e.g. antibody, treated with the methods described herein has increased storage stability compared to an untreated control. In another embodiment, the protein, e.g. antibody, treated with the methods described herein has a decreased tendency to aggregate compared to an untreated control. In still other embodiments, treatment of a protein, e.g. antibody, with the methods described herein results in decreased oxidation, e.g. methionine oxidation, as compared to an untreated control.

Therefore, one embodiment provides a method for reducing protein oxidation, e.g. methionine oxidation, in a composition of proteins, e.g. antibodies, comprising reducing the level of trisulfides in the composition of proteins. Another embodiment provides a method for reducing protein aggregation in a composition of proteins, e.g. antibodies, comprising reducing the level of trisulfides in the composition of proteins. Another embodiment provides a method of increasing protein stability in a composition of proteins, e.g. antibodies, comprising reducing the level of trisulfides in the composition of proteins.

In some embodiments, methods described herein can be used to increase or enhance long-term protein and antibody storage stability. Therefore, one embodiment provides a method for improving long-term antibody storage stability by converting trisulfide bonds to disulfide bonds in an antibody wherein the method comprises: (a) allowing antibodies in a solution comprising at least one antibody with at least one trisulfide bond to contact and associate with a solid support; (b) exposing said antibodies to a solution comprising a reducing agent; (c) replacing the solution comprising the reducing agent with a solution lacking the reducing agent, and (d) preparing said antibodies in a composition for long-term storage, wherein steps (a) and (b) are performed simultaneously or in any sequential order, followed subsequently by step (c) then step (d). In one embodiment, improving long-term antibody storage stability reduces cleavage or loss of covalent bonding of antibody light chains from intact antibody molecules. In another embodiment, improving long-term antibody storage stability reduces the formation of antibody aggregates.

In some embodiments, the method of improving long-term antibody storage stability results in an improvement in long-term storage stability in an amount selected from the group consisting of: (a) at least about 5% improvement; (b) improvement of 5% or more; (c) at least about 10% improvement; (d) improvement of 10% or more; (e) at least about 15% improvement; (f) improvement of 15% or more; (g) at least about 20% improvement; (h) improvement of 20% or more; (i) at least about 25% improvement; (j) improvement of 25% or more; (k) at least about 30% improvement; (l) improvement of 30% or more; (m) at least about 40% improvement; (n) improvement of 40% or more; (o) at least about 50% improvement; (p) improvement of 50% or more; (q) at least about 60% improvement; (r) improvement of 60% or more; (s) at least about 80% improvement; and (t) improvement of 80% or more. The amount of improvement can be determined by comparing the antibody specific binding activity, percentage of intact antibody molecules, or percentage of antibody aggregates in an antibody composition prepared according to the methods described versus an antibody composition not prepared according to the methods described. The improvement can be determined at any time during or after long-term storage.

In some embodiments, the long-term storage comprises storage for a period selected from the group consisting of: (a) 1 month or longer; (b) 2 months or longer; (c) 3 months or longer; (d) 4 months or longer; (a) 5 months or longer; (e) 6 months or longer; (f) 8 months or longer; (g) 10 months or longer; (h) 12 months or longer; (i) 18 months or longer; (j) 24 months or longer; (k) 30 months or longer; (l) 36 months or longer; (m) 48 months or longer; and (n) 72 months or longer. In some embodiments, the antibodies are stored in a substantially hydrated or a substantially non-hydrated form.

In some embodiments, the long term storage comprises storage for a period of 1 month or longer at a temperature selected from the group consisting of: (a) −70° C. or below; (b) about −70° C.; (c) −70° C. or above; (d) −20° C. or below; (e) about −20° C.; (f) −20° C. or above; (g) 0° C. or below; (h) about 0° C.; (i) 0° C. or above; (j) 4° C. or below; (k) about 4° C.; (l) 4° C. or above; and (m) 20° C. or below.

In some embodiments, the protein treated with the methods described herein is formulated into a "pharmaceutically acceptable" form. "Pharmaceutically acceptable" refers to a bioproduct that is, within the scope of sound medical judgment, suitable for contact with the tissues of human beings and animals without excessive toxicity or other complications commensurate with a reasonable benefit/risk ratio.

Antibodies treated according to the methods described herein can be formulated into pharmaceutical compositions for administration to mammals, including humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in the methods of the present invention can be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

A specific dosage and treatment regimen for any particular patient will depend upon a variety of factors, including the particular antibody used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinctic principles well known in the art.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), *DNA Cloning*, D. N. Glover ed., Volumes I and II (1985); *Oligonucleotide Synthesis*, M. J. Gait ed., (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical—Immunology* (8th ed.), Appleton & Lange, Norwalk, Conn. (1994) and Mishell and Shiigi (eds), *Selected Methods in Cellular Immunology*, W.H. Freeman and Co., New York (1980).

Standard reference works setting forth general principles of immunology include *Current Protocols in Immunology*, John Wiley & Sons, New York; Klein, J., Immunology: *The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunology* $4^{th}$ ed. Ed. Richard A. Goldsby, Thomas J. Kindt and Barbara A. Osborne, H. Freemand & Co. (2000); Roitt, I., Brostoff, J. and Male D., Immunology 6th ed. London: Mosby (2001); Abbas A., Abul, A. and Lichtman, A., *Cellular and Molecular Immunology* Ed. 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, Genes VIII, Prentice Hall (2003); Harlow and Lane, *Antibodies: A Laboratory Manual*, Cold Spring Harbor Press (1988); Dieffenbach and Dveksler, *PCR Primer* Cold Spring Harbor Press (2003).

All of the references cited above, as well as all references cited herein, are incorporated herein by reference in their entireties.

EXAMPLES

Example 1

Recombinant Antibodies Contain Trisulfide Bonds

An IgG1 monoclonal antibody (IgG1 mAb-A) expressed in Chinese Hamster Ovary (CHO) cell clarified conditioned medium (CCM) was found to contain a trisulfide modification via multiple analytical techniques. Mass spectrum analysis showed a peak width broadening for the intact, non-reduced mAb. The average mass was increased, and both the mass increase and the peak broadening effect were eliminated by reducing conditions.

In these experiments, preparations of IgG1 mAb were first analyzed for monomeric, high and low molecular weight species by size exclusion high pressure liquid chromatography (SEC-HPLC) under isocratic conditions. The analysis was performed using a Tosoh Biosciences G3000SWXL analytical column with a TSKgel guard column (#08543), a Waters 600S controller and a 717plus autosampler controlled by Empower software. Subsequent peptide mapping analysis was performed by high pressure liquid chromatography and mass spectrometry (LC-MS). Monoclonal antibodies (approximately 100 µg) were treated with 4-vinylpyridine at ambient temperature for 30 minutes in the presence of approximately 6 M guanidine hydrochloride. The protein was then recovered by ethanol precipitation. Approximately 20 µg of the 4-vinylpyridine-treated mAb was digested with endo-Lys-C (Wako, #125-02543) in the presence of 2 M urea at ambient temperature for 16 hours. An aliquot (approximately 4 µg) was adjusted to 5 M urea and separated on a T3 HSS column in a gradient of acetonitrile and trichloroacetic acid using a UPLC-LCT Premier system (Waters). Data generated by the liquid chromatography/mass spectrometry (LC-MS) analysis were processed using MassLynx 4.1 software. The percentage of trisulfide-linked H-L peptides was calculated from peak areas on the UV trace or on the extracted-ion-chromatogram of all three charged states, 1+ to 3+, with known peptides used as internal standards. The percent H-L trisulfide was calculated as (peak area of trisulfide)/(peak area of disulfide+peak area of trisulfide). The limit of detection for the assay was <0.1%. The limit of quantification is <1%. These experiments confirmed the presence of trisulfide bonds, and revealed that the predominant site of modification was the bond between the heavy and light chains (H-L bond). Modification of hinge region disulfides occurred at a lower frequency. In contrast, no trisulfide modification of intrachain disulfide bonds was detected.

In addition, it was observed that the IgG1 mAb-A preparation containing H-L trisulfide displayed increased sensitivity to extreme heat treatment compared to a similar preparation, termed "mAb-A-LT", in which trisulfides were undetectable. In these experiments, analysis of IgG1 mAb was performed by denaturing, non-reducing capillary electrophoresis in the presence of sodium dodecyl sulfate using an IgG Purity/Heterogeneity Assay Kit (# A10663) and ProteomeLab PA-800 instrument (Beckman Coulter). Samples (200 µg) were prepared by heating to 70° C. for 3 minutes in the presence of iodoacetamide, 1 mM SDS and a 10 kDa standard essentially as per manufacturer's instructions (Protocol A10424-AC) and separated for 35 min in a bare fused silica capillary with detection at 220 nm. The results, shown in FIGS. 1A and 1B show an increased level of fragmentation following sample preparation for non-reducing electrophoresis. The electrophoretic migration pattern of the single most abundant fragment was consistent with the loss of one light chain (L) from the intact mAb with the simultaneous generation of a species consisting of two heavy chains and one light chain (HHL fragment). This phenomenon was then used to rapidly screen for conditions that influence trisulfide content in IgG1 mAbs. In this screen, non-reducing electrophoresis was used as a rapid assay for detection of trisulfide bonds.

Example 2

Fermentation Conditions Affect Generation of Trisulfides

In order to determine if fermentation conditions affect trisulfide bond levels, a series of studies was performed in bioreactors. An experiment was performed to test the impact of fermentation time in a 200 liter bioreactor using the anti-LINGO-1 antibody Li81. The time course revealed a bell shaped curve. At early time points, trisulfide levels were high. Trisulfide levels dropped as cultures achieved maximum cell density and maximum antibody production, and the levels increased again at later time points. Based on these studies, day 13 was selected as ideal for production.

Similar studies were performed in bioreactors of varying sizes: small bioreactors (e.g., 3-6 liters), 200 liter bioreactors, and 2000 liter bioreactors. The data suggest that it is possible to achieve lower trisulfide bond levels via production of proteins in large volume cell cultures, for example, as cultured in large bioreactors.

Example 3

Treatment with Hydrogen Sulfide Increases Trisulfide Bonds

In order to determine if hydrogen sulfide concentrations in cell culture could affect trisulfide bond levels, mAb-A containing 2% trisulfide was exposed to increasing concentrations of hydrogen sulfide for increasing amounts of time. In these experiments, Mab (7.5 mg/mL) in 50 mM Tris pH 7.8 was treated with 2.5, 0.5 or 0.125 mM $H_2S$ diluted from a 125 mM $H_2S$ water solution (Ricca Chemical Company). Samples were incubated for 3 hours RT, 24 hours RT, or 90 min at 37° C. and immediately desalted on P6DG spin columns equilibrated in 10 mM sodium citrate pH 6.5, 50 mM NaCl to remove excess $H_2S$. Samples were analyzed by peptide mapping. The results, shown in FIG. 2, demonstrate that both increases in either the concentration of hydrogen sulfide or the time of exposure to hydrogen sulfide correlated with increased trisulfide bonds.

Example 4

Cysteine Concentrations Affect Trisulfide Bonds

In order to determine if concentrations of cysteine affect trisulfide bond formation, trisulfide bond levels in cell cultures fed additional cysteine were evaluated. On day 14, cultures were either fed a complete feed+supplemental amino acids+supplemental Cys; complete feed+supplemental Met+Cys; or complete feed+supplemental Met only. The results, shown in FIG. 3, demonstrate that increased trisulfide bond levels in protein samples correlates with increased concentrations of cysteine in a cell culture, at least when supplementation is performed late in a cell culture run (e.g., at or after day 14).

Example 5

Characterization of Trisulfide Modification in Antibodies

Monoclonal antibodies (mAbs) are an important class of biopharmaceuticals for treatment of disease (Nieri et al., *Curr. Med. Chem.* 16 (2009) 753-779 and Walsh, *Nat. Biotechnol.* 24 (2006) 769-776). All share similar structural characteristics, high specificity, and long half-life. Successful development of biopharmaceuticals relies on continuous improvements in methods used to assess product heterogeneity. Common sources of heterogeneity are post-translational modifications, resulting from glycosylation, oxidation, deamidation, disulfide linkage scrambling, proteolytic cleavage, misfolding, etc. (Liu et al., *J. Pharm. Sci.* 97 (2008) 2426-2447). Some modifications such as oxidation, deamidation, and glycation occur during protein production, processing, and storage and can be detrimental (Jenkins et al., *Mol. Biotechnol.* 39 (2008) 113-118), while others—glycosylation, phosphorylation, disulfide linkage formation—are required for correct protein structure and function (Walsh, *Posttranslational Modification of Proteins: Expanding Nature's Inventory*, Roberts and Co. Publishers, 2005). Therefore, post-translational modifications are closely monitored to ensure the consistency in product quality (Jenkins et al., *Mol. Biotechnol.* 39 (2008) 113-118; Barnes and Lim, *Mass Spectr. Rev.* 26 (2007) 370-388; and Zhang et al., *Mass Spectr. Rev.* 28 (2009) 147-176).

Antibodies are multi-domain proteins composed of two copies of light and two copies of heavy chains with multiple interchain and intrachain disulfide bonds. Incorrect pairing of disulfide bonds may affect the folding that can lead to a change in protein function, such as antigen recognition, binding affinity, structure, and stability (Glockshuber et al., *Biochemistry* 31 (1992) 1270-1279). Commonly seen modifications in disulfide structure include disulfide bond scrambling (Glocker et al., *J. Am. Soc. Mass Spectr.* 6 (1995) 638-643), glutathionylation (Gallogly and Micyal, *Curr. Opin. Pharmacol.* 7 (2007) 381-391), cysteinylation (Banks et al., *J. Pharm. Sci.* 97 (2008) 775-790), and oxidation. Trisulfide linkages in proteins, resulting from insertion of a sulfur atom into a disulfide bond, have been rarely documented. The presence of a trisulfide in a protein was first reported for the minor disulfide loop of *E. coli*-derived recombinant human growth hormone (hGH) (Jespersen et al., *Eur. J. Biochem.* 219 (1994) 365-373; and Andersson et al., *Int. J. Pept. Protein Res.* 47 (1996) 311-321); later it was also seen in the major disulfide loop in a methionyl hGH (Canova-Davis et al., *Anal. Chem.* 68 (1996) 4044-4051). Trisulfides have also been detected in a recombinant, truncated interleukin-6 expressed in *E. coli* (Breton et al., *J. Chromatogr. A* 709 (1995) 135-146.), and in Cu,Zn-superoxide dismutase isolated from human erythrocytes (Okado-Matsumoto et al., *Free Radic. Biol. Med.* 41 (2006) 1837-1846). The trisulfide modification in hGH had no effect on function in vitro or on the pharmacokinetics of the compound (Thomsen et al., *Pharmacol. Toxicol.* 74 (1994) 351-358), but it did affect the hydrophobicity of the protein. Methods including buffer exchange, pH control, and mild reduction have been developed for hGH to reduce trisulfide levels or to convert the trisulfide back to a disulfide (U.S. Pat. No. 7,232,894). Recently, trisulfides were reported in the Cys linkages between the heavy chains of a recombinant human IgG2 mAb (Pristatsky et al., *Anal. Chem.* 81 (2009) 6148-6155). We report here the discovery of trisulfide linkages between the light and heavy chains in preparations of recombinant and natural IgG 1, 2, 3, and 4 isotypes. The amount of trisulfide in mAbs varies and occurs predominately in the linkage between the light and heavy chains. A mass spectrometric method for their determination and quantification, the impact of fermentation conditions on trisulfide formation, and the effect of trisulfide modification on antibody activity and stability is also discussed.

Materials and Methods

Monoclonal antibodies [mAb1 (aglycosyl form), mAb2 (wild type and aglycosyl forms), mAb3, mAb4, mAb5, mAb6, and mAb7] were produced in CHO cells and purified by protein A affinity chromatography at Biogen Idec (Cambridge, Mass.). Natural human myeloma IgGs were obtained from Sigma-Aldrich (St. Louis, Mo.). Product numbers were I 5154 for IgG1, I 5404 for IgG2, I 5654 for IgG3, and I 4639 for IgG4. Commercial mAb pharmaceuticals (referred to as Drug 1, Drug 2, and Drug 3) were obtained through appropriate agencies.

Intact Mass Analysis. About 22.5 μg of the native protein was analyzed on an LCT electrospray time-of-flight mass spectrometer (Waters, Milford, Mass.). Prior to analysis the protein was desalted using a narrowbore Vydac C4 cartridge (5 μm particle size, 2.1 mm I.D.) connected to an Acquity UPLC system (Waters, Milford, Mass.). Mobile phase A was 0.03% trifluoroacetic acid in water, and mobile phase B was 0.024% trifluoroacetic acid in acetonitrile. The proteins were desalted using 100% A for 5 min, then eluted with 80% B in 1 min at flow rate of 0.1 mL/min. Molecular masses were obtained by deconvolution using the MaxEnt 1 program. Average peak widths in the raw mass spectra were determined from charge states 49 to 51 by measuring the full width at half maximum (FWHM).

Alkylation of Proteins. About 1.0 μL of a 1:10 dilution of 4-vinylpyridine (in 8 M guanidine hydrochloride) was added to 12.5 μL of a solution containing ~90 μg of the protein, and 8 M guanidine hydrochloride was added to the mixture to give a final volume of 50 μL. The solution was kept at 20° C. in the dark for 30 min. The alkylated protein was recovered by precipitation with 40 volumes of cooled ethanol. The mixture was stored at −20° C. for 1 h and then centrifuged at 14000 g for 12 min at 4° C. The supernatant was discarded and the precipitate (~22.5 μg/vial) was washed once with cooled ethanol.

Non-reduced Tryptic and Endoprotease Lys-C Peptide Mapping. For tryptic digestion, about 22.5 μg of the 4-vinylpyridine-treated protein was digested with 5% (w/w) of endo-Lys-C (Wako Chemical, Richmond, Va.) in 50 μL of 2 M urea, 0.2 M Tris.HCl, 2 mM $CaCl_2$, pH 6.5, for 5 h at room temperature, after which 10% (w/w) of trypsin (Promega, Madison, Wis.) was added and the solution was kept at room temperature for additional 15 h. Prior to analysis of the digests by LC-MS, 50 μL of 8 M urea was added to each digest, and the digest was split equally into two vials: the sample in one vial was reduced with of 30 mM TCEP in 150 mM Tris, pH 6.0, 1 mM EDTA, at 37° C. for 1 h; the other portion was analyzed directly without the reduction. Both the reduced and non-reduced digests were analyzed on a Waters UPLC-LCT Premier XE system (Waters, Milford, Mass.). Mobile phase A was 0.03% trifluoroacetic acid in water, and mobile phase B was 0.024% trifluoroacetic acid in acetonitrile. An aliquot of 50 pmole of the digests was separated on a 2.1×150 mm T3 HSS column with a gradient of 0% to 40% B over 60 min. The flow rate was 70 μL/min.

For focused Lys-C peptide mapping, about 22.5 μg of the 4-vinylpyridine-treated protein was digested in 50 μL of 2 M urea, 2 mM $CaCl_2$, 0.2 M Tris-HCl (pH 6.5), with 10% (w/w) of Lys-C (Wako) for 16 h at room temperature. Prior to analysis of the digests by LC-MS, 50 μL of 8 M urea was added to each digest. An aliquot of the digest of 25 pmol native protein (3.8 μg) was analyzed on the same LC-MS system, except that the gradient was from 10% to 19.5% B in 10 min. The percentages of the trisulfide-linked peptides were calculated from peak areas on either the UV trace or extracted ion chromatogram (EIC).

Spiking experiments. Samples of both mAb2-agly C (which contains 7.8% trisulfide at the LC5-HC5 linkage) and mAb2-agly D (which has no detectable trisulfide) were diluted to 1.0 mg/mL with PBS. The concentration of the protein was calculated from its UV absorbance at 280 nm using a calculated extinction coefficient [$A_{280}$ (1 mg/mL)= 1.44 mL/mg cm]. To determine the detection limit of the trisulfide at the LC5-HC5 linkage, different amounts (0.56%-50%) of mAb2-agly C were spiked into mAb2-agly D, using low-volume microsyringes. An aliquot containing 25 pmole (3.8 µg) of the digest was injected for Lys-C peptide mapping analysis with the lowest concentration of trisulfide spike being run first, followed by increasingly higher amounts of spike. The samples were analyzed in duplicate in each case. Between sample runs, the column was cleaned by injecting water and running the gradient. The amount of the trisulfide was estimated from peak areas in extracted ion chromatograms (EIC) for the disulfide-linked and the corresponding trisulfide-linked peptide clusters containing the LC5-HC5 linkage.

Incubation with $H_2S$. The protein (mAb1, 7.5 mg/mL) in 50 mM Tris buffer (pH 7.8) was treated with 0.5-, 2.0- or 2.5-mM $H_2S$ diluted from a 125-mM $H_2S$ water solution (Ricca Chemical Co., Arlington, Tex.). Samples were incubated for 3 h or 24 h at room temperature, or 90 min at 37° C. After incubation, samples were immediately desalted on Bio-gel P6DG spin columns (Bio-Rad, Carlsbad, Calif.) equilibrated in 10-mM sodium citrate 50 mM NaCl, pH 6.5, in order to remove excess $H_2S$. Samples were analyzed by peptide mapping.

Analysis of mAb 1 and mAb2 Functions by Direct Binding ELISA. Costar 96-well easy wash plates were coated overnight with 5 µg/mL human antigen that binds to mAb1 (50 µL/well), in 50 mM sodium carbonate (pH 9.5) at 4° C. Plates were washed 3 times with 350 µL of PBS using a plate washer and blocked with 1% BSA, 0.1% ovalbumin, and 0.1% non-fat dry milk in Hank's balanced salt buffer containing 25 mM HEPES (pH 7.0) for 1 hour at room temperature. Plates were then washed again, and incubated for 1 h with a 3-fold dilution series set up for each test compound (50 µL/well, 8 dilutions) starting at 10 µg/mL and all in 0.1% BSA, 0.1% ovalbumin, and 0.1% non-fat dry milk in Hank's balanced salt buffer containing 25 mM HEPES (pH 7.0), and again washed. Bound mAb1 was detected using AP-anti-human Fab. Plates were incubated for 1 h at room temperature, washed, and treated with 10 mg/mL 4-nitrophenylphosphate alkaline phosphate substrate in 100 mM glycine, pH 10.5, 1 mM $MgCl_2$, 1 mM $ZnCl_2$. Plates were read at 405 nm on a Molecular Devices plate reader. $EC_{50}$ values for binding were calculated from the titration curve using prism software. The function of mAb2 was assessed as for mAb1 except that 96 well microplates were coated overnight at 4° C. with 1 µg/mL (in 15 mM $Na_2CO_3$, 35 mM $NaHCO_3$, pH 9.6) of a human antigen that binds to mAb2. Plates were blocked for 1 h at room temperature with PBS containing 2% BSA. Antibodies were diluted to the indicated concentrations and incubated for 2 h at room temperature. Binding was determined using a horseradish peroxidase-conjugated goat anti-human polyclonal antibody (Jackson ImmunoResearch, West Grove, Pa.) followed by measurement of horse radish peroxidase activity using the substrate tetramethylbenzidine.

Assessing the Stability of Trisulfides in Rat Serum in vitro and in vivo. For in vitro studies, 500 µg of mAb 1-B (20% trisulfide in the light-heavy chain linkage) was incubated in PBS or in 1 mL of normal rat serum at 37° C. for 16 or 96 h, after which time the protein was purified on IgSelect affinity resin (GE Healthcare, Piscataway, N.J.). The samples were incubated with 100 µL of the resin for 2 h at room temperature with mild agitation. The resin was then washed six times with 0.5 mL of PBS and six times with 0.5 mL of 25 mM sodium phosphate, 100 mM NaCl, pH 5.5, after which the bound antibody was eluted with 25 mM sodium phosphate, pH 2.8, 100-mM NaCl. The eluate was neutralized by the addition of ¹⁄₂₀ volume of 0.5 M sodium phosphate, pH 8.6. For in vivo studies, three 200-g Sprague Dawley rats were injected intraperitoneally with 100 mg/kg mAB1-B. The blood was drawn after 24 and 72 h, and allowed to clot to form serum. Portions of the serum (750 µL for the 24-h point, and 1050 µL for the 72-h point) were subjected to IgSelect purification using 150 µL of IgSelect (protocol described above). The purified mAb1 was analyzed by non-reduced SDS-PAGE and Lys-C peptide mapping to determine the trisulfide level. The reisolated mAb1 samples from the in vitro and in vivo studies were intact and >95% pure by SDS-PAGE. Based on column recoveries, levels of mAb1 in the serum after 24 and 72 h were 850 and 700 µg/mL of mAb1, respectively, which matched the theoretical predictions generated from rat pharmacokinetic studies of mAb1 samples lacking trisulfide.

Results

Intact Mass Analysis. The presence of trisulfides in monoclonal antibody 1 (mAb1) was anticipated from intact mass measurements where an increase of up to 20 Da was observed in some non-reduced samples, but not in reduced ones. The increase in mass was accompanied by a broader than expected peak width in the raw mass spectrum indicating product heterogeneity. The magnitude of the increase in mass and peak broadening directly correlated with the level of trisulfide, which was confirmed by peptide mapping. The mass spectrum of mAb1-B (an aglycosyl IgG1 antibody), which has 20% trisulfide at the LC5-HC5 linkage was overlaid on the mass spectrum of mAb1-A, which as 0.5% trisulfide at the LC5-HC5 linkage, at charge +50. Peak broadening resulted in a shift in the observed mass of the protein from 144,440 Da to 144,459 Da.

Peptide Mapping of non-reduced proteins and Tandem Mass spectrometry. Fully characterized peptide maps of mAb 1 were developed for identification and quantification of the trisulfide modification. Tryptic peptide mapping of reduced mAb1 (reduced map) confirmed the amino acid sequences, but did not reveal any modification that could account for the mass increase observed by intact mass measurement of native mAb1-B. Peptide maps of non-reduced protein were used to study the peptide linkages that form the disulfide structure of the protein. As shown schematically in FIG. 4A, IgG1 antibodies contain 12 intrachain and 4 interchain disulfides. Tryptic peptide mapping of non-reduced mAb1-B revealed all the predicted disulfide-linked peptide clusters as major components in the peptide map. Three extra peaks, eluting at 16, 19, and 54 min in the tryptic map of the non-reduced protein that were not present in the peptide map of the reduced protein were also detected. The molecular masses of the components in these peaks are 788.217, 1292.457, and 5486.767 Da, respectively. Extracted ion chromatograms (EIC) of the peptides showed eluting at 16 and 19 min, respectively. The mass of 788.217-Da component is 32 Da higher than the calculated mass (756.242 Da) for the disulfide-linked peptide cluster PepLT20/PepHT17 [i.e., the tryptic peptide #20 of the light chain (PepLT20) and tryptic peptide #17 of the heavy chain (PepHT17) are linked through Cys residues]. Similarly, the mass of the 1292.457-Da component is 32 Da higher than the mass calculated for the disulfide-linked peptide cluster PepLT19-20/PepHT17 (1260.486 Da), which arises by partial digestion of the protein (i.e., the peptide bond between peptides PepLT19 and PepLT20 has not been cleaved). The peptide clusters that elute at 16 and 19 min both contain Cys residue 5 of the light chain (LC5) and Cys residue 5 of the heavy chain (HC5) which form the interchain disulfide that links the heavy chain and light chain (FIG. 4).

Tandem mass spectrometry was performed on these peptides to confirm the type and location of the modification. The CID mass spectra obtained from the doubly charged ions of the disulfide-linked and the presumed trisulfide-linked PepLT19-20/PepHT17 peptide clusters were analyzed. Fragment ions lacking a Cys residue showed the same masses in both spectra. However, all the fragment ions containing Cys showed 32-Da differences in the corresponding CID spectrum. For example, m/z of the y1 ion is 571.25 for PepLT19-20/PepHT17 disulfide cluster, but 603.08 for the corresponding trisulfide cluster. Furthermore, some of the disulfide and trisulfide bonds were cleaved during the CID experiment. In the CID spectrum of the trisulfide-linked peptide cluster, PepLT19-20+2S (876.33 Da) and PepHT17+2S (516.17 Da) were clearly observed while these ions were absent in the CID spectrum of the corresponding disulfide-linked peptide cluster.

The peak eluting at 54 min in the peptide map of the non-reduced protein was subjected to the same analysis. The 5486.767-Da component is 32 Da higher than the mass calculated for the disulfide-linked hinge peptides of the heavy chain (PepHT18-PepHT18, 5454.783 Da), in which HC6 and HC7 on one heavy chain are linked to the same residues on the other heavy chain. Both pairs of Cys residues must be involved in a trisulfide linkage because there were two overlapping peaks in the EIC for the trisulfide-linked cluster of the heavy chain (data not shown). However, the exact linkage could not be determined by CID MS/MS because of the low abundance of these species.

The EIC data for the modified and unmodified LC5-HC5 and HC6/7-HC6/7 peptide clusters were used to quantify trisulfide levels in the mAb1-B sample. Trisulifide bonds in mAb 1-B accounted for 20% of the LC5-HC5 linkage and 4% of the HC6/7-HC6/7 linkages.

Trisulfides in Other Antibodies. Natural and recombinant antibody preparations representing all IgG subclasses were examined in order to better understand the frequency of occurrence of trisulfide linkages in antibodies. Tables 12 and 13 show all subclasses of IgG antibodies contain trisulfides.

Table 12 summarizes results generated with 7 non-clinical recombinant monoclonal antibodies. Trisulfide levels at the LC5-HC5 linkage in the mAb1 preparations ranged from 0.2-39.3%. Trisulfide levels at the LC5-HC5 linkage of the mAb2 preparations (wild type and aglycosyl IgG1) varied from <0.1% to 21%. Trisulfide levels in the HC6/7-HC6/7 linkages were considerably lower than in the LC5-HC5 linkage and demonstrated that the LC5-HC5 connection was the most sensitive site for trisulfide modification. No trisulfides were detected in intrachain disulfide linkages. In IgG2, IgG3, and IgG4 mAbs, the heavy and light chains are joined via a LC5-HC3 disulfide bond in place of the LC5-HC5 linkage found in IgG1 mAbs. Trisulfide levels in the LC5-HC3 linkage of two IgG4 mAbs, mAb5 and mAb6, were 11% and 5%, respectively. Trisulfide levels in the HC6/7-HC6/7 linkages were 4% for mAb5 and <1% for mAb6 (Table 12 and FIG. 4D) and no intrachain trisulfides were detected. Trisulfide levels at the LC5-HC3 linkage of IgG 2 mAb3 ranged from 0.4 to 6% (Table 12 and FIG. 4B), and there was no detectable trisulfide in the hinge and intrachain disulfide linkages. Trisulfide levels at the LC5-HC3 linkage of IgG3 mAb4 was 5% (Table 12 and FIG. 4C). Monoclonal antibody 7 (mAb7), a chimeric human/murine IgG2a antibody, contained 19-28% trisulfides at LC5-HC3 and 0-1% trisulfides in each of the three Cys linkages between the heavy chains (Table 12).

TABLE 12

Trisulfide levels in recombinant antibodies detected using the detailed peptide mapping method

| Sample | Number of Preparations | Trisulfide (%) Between the light and heavy chains | Trisulfide (%) Between the heavy chains | Cys linkages |
|---|---|---|---|---|
| mAb1 (human IgG1) | 7 | 0.2-39.3 | 0-6.8 | LC5-HC5 HC6/7-HC6/7 |
| mAb2 (human IgG1) | 3 | <0.1-15.8 | 0-4.7 | |
| mAb3 (human IgG2) | 11 | 0.4-6.3 | Not observed | LC5-HC3 |
| mAb4 (human IgG3) | 1 | 11.0 | Not observed | LC5-HC3 |
| mAb5 (human IgG4) | 1 | 10.8 | 4.0 | LC5-HC3 HC6/7-HC6/7 |
| mAb6 (human IgG4) | 1 | 5.2 | Not observed | |
| mAb7 (murine IgG2a) | 4 | 19.0-28.1 | 0-3.0 | LC5-HC3 HC6/7/8-HC6/7/8 |
| mAb1 (human IgG1) agly | 90 | 0.2-39.3 | 0-6.8 | LC5-HC5 HC6/7-HC6/7 |
| mAb2 (human IgG1) wt + agly | 135 | <0.1-20.6 | 0-4.7 | |
| mAb3 (human IgG1) | 12 | 2.9-13.0 | Not observed | |
| mAb4 (human IgG2) | 11 | 0.4-6 | Not observed | LC5-HC3 |
| mAb5 (human IgG3) | 1 | 11.0 | Not observed | LC5-HC3 |
| mAb6 (human IgG4) | 1 | 10.8 | 4.0 | LC5-HC3 HC6/7-HC6/7 |
| mAb7 (human IgG4) | 1 | 5.2 | Not observed | |
| mAb8 (murine IgG2a) | 4 | 19.0-28.1 | 0-3.0 | LC5-HC3 HC6/7/8-HC6/7/8 |

Table 13 summarizes peptide mapping results from additional studies where three commercial IgG1 therapeutic mAbs and natural preparations of IgG1, IgG2, IgG3, and IgG4 samples isolated from human myeloma plasma were characterized. The three commercial IgG1 therapeutic mAbs contained 1-4% trisulfide at the LC5-HC5 linkage. The IgG1, IgG2, IgG3, and IgG4 samples isolated from human myeloma plasma contained ~1% trisulfide at the linkage between the light and heavy chains (LC5-HC5 for IgG1 and LC5-HC3 for the rest; Table 13 and FIG. 4) and no other trisulfide linkages were detected. These results demonstrate that trisulfides can occur in any antibody, regardless of subclass, glycosylation state, or whether it is an endogenous or recombinant protein.

TABLE 13

Trisulfide levels in commercial therapeutic IgG1 antibodies and in human myeloma IgG1, IgG2, IgG3, and IgG4 antibodies.

| Sample | Notes | Trisulfide in Cys-linkage between the light and heavy chains (%) | Cys linkages |
|---|---|---|---|
| Drug 1 (IgG1) | | 4.1 | LC5-HC5 |
| Drug 2 (IgG1) | | 0.5 | |
| Drug 3 (IgG1) | Lots 1-3 | 1.4-3.1 | |
| Human IgG1 | from human myeloma plasma | 0.6 | |

TABLE 13-continued

Trisulfide levels in commercial therapeutic IgG1 antibodies and in human myeloma IgG1, IgG2, IgG3, and IgG4 antibodies.

| Sample | Notes | Trisulfide in Cys-linkage between the light and heavy chains (%) | Cys linkages |
| --- | --- | --- | --- |
| Human IgG2 | from human myeloma plasma | 1.1 | LC5-HC3 |
| Human IgG3 | from human myeloma plasma | 1.5 | |
| Human IgG4 | from human myeloma plasma | 0.9 | |

Focused Peptide Mapping for Monitoring Trisulfide Linkages in IgG1 mAbs. A focused Lys-C peptide mapping method that monitors the LC5-HC5 linkage was developed to increase sample throughput. The LC5-HC5 linkage was targeted because the level of the trisulfide linkage between the light and heavy chains was consistently higher than that between the two heavy chain for IgG1 mAbs. FIG. 5A shows the EICs (I and II) and UV trace (III) of the disulfide and trisulfide linked peptide clusters containing LC5 and HC5 in the Lys-C peptide map of the non-reduced protein. The percentage of trisulfide modified LC5-HC5 shown in FIG. 5A-III is about 20%, the same as that seen in the tryptic peptide map. The focused peptide mapping method, utilizing the simplified digestion process and a reduced separation time from 70 min to 15 min, was applied to all subsequent trisulfide analyses of IgG1 antibodies. The trisulfide detection limit for this method at the LC5-HC5 linkage, assessed by spiking experiments, is 0.1% (FIG. 5B; $R^2$=0.9989), and standard deviation of the method, based on more than twenty individual experiments of a single preparation is 0.07 (relative standard deviation is 3.8%, FIG. 5C). More than two hundred preparations of IgG1 mAb1 and mAb2 were analyzed using the focused peptide mapping method in support of studies designed to understand the impact of fermentation conditions in bioreactors on trisulfide formation (see below).

Effect of Cell Culture Conditions on Trisulfide Formation. Evaluation of trisulfide levels in mAb1 from 21 bioreactor runs revealed that cell culture conditions had a very dramatic effect on trisulfide formation. Time course studies from four 200-L bioreactors were run under near identical conditions, and the four bioreactors all showed a similar profile where trisulfide levels were minimal around day 12 or day 13 and considerably higher earlier or later (e.g. at day 9 or day 16). Bioreactor studies with mAb2 (wild type and aglycosyl forms) showed a similar trend. Trisulfide levels in mAb1 samples from 2000-L bioreactors using conditions developed at the 200 L scale showed similar consistency. To investigate other variables that might impact trisulfide formation for mAb1, a number of cell culture parameters such as cell density and feed strategies were varied in 3 to 6-L bioreactor studies. Trisulfide analysis of the samples from these runs revealed that the trisulfide content in the LC5-HC5 linkage varied considerably from <1% to 39%, and the measurements from the 200 L and 200 L sizes were less than 5%. Although evaluation of culture conditions showed no simple correlation between the levels of trisulfides and any identifiable parameter, these studies indicate that cell culture conditions significantly affect trisulfide levels in mAbs.

Effect of $H_2S$ Concentration on the Trisulfide Level. Studies with recombinant hGH made in *E. coli* indicated that the trisulfide level correlates with $H_2S$ produced during fermentation (U.S. Pat. No. 7,232,894). In an attempt to determine whether the $H_2S$ concentration affects the level of the trisulfide in antibodies, a sample of mAb1 (mAb1-A) with 0.5% trisulfide in LC5-HC5 linkage was incubated with different concentrations of $H_2S$. Similar to the observations with hGH (U.S. Pat. No. 7,232,894), trisulfide formation in mAb1 is dependent on the concentration of $H_2S$ in the buffer (Table 14). Incubation with 0.5 mM $H_2S$ at 37° C. for 90 min increased the trisulfide level from 0.5% to 5%. The highest trisulfide levels obtained in the presence of $H_2S$ were about 15%. Prolonged incubation did not increase the levels. Detailed tryptic peptide mapping analysis of these samples showed that the sulfur addition occurred only in the inter-chain Cys linkages, as was observed in the mAb1 preparations isolated from bioreactors.

TABLE 14

Effect of $H_2S$ on trisulfide levels at the LC5-HC5 linkage.

| Sample | Reagent | Experimental Conditions | Trisulfide (%) |
| --- | --- | --- | --- |
| mAb1-A | untreated | / | 0.5 |
| | $H_2S$ | 0.5 mM, 37° C., 90 min | 4.3 |
| | $H_2S$ | 2.5 mM, 37° C., 90 min | 7.7 |
| | $H_2S$ | 0.5 mM, Room Temperature, 3 h | 4.5 |
| | $H_2S$ | 2.5 mM, Room Temperature, 3 h | 15.4 |
| | $H_2S$ | 0.5 mM, Room Temperature, 24 h | 4.6 |
| | $H_2S$ | 2.5 mM, Room Temperature, 24 h | 14.7 |

Effect of Trisulfides on Antibody Binding to Antigen. The binding affinity of a mAb1 sample (mAb1-C) containing 39% trisulfide at the LC5-HC5 linkage was compared with that of mAb1-A containing about 0.5% of trisulfide at the LC5-HC5 linkage using an ELISA-based binding assay. Both of the samples produced the same sigmoidal binding curve with calculated $EC_{50}$ values of 20 pM. Furthermore, an in vitro bioassay showed that activities of both mAb1 samples were indistinguishable. The binding affinities of wild type and aglycosyl mAb2 with high and low trisulfide levels at the LC5-HC5 linkage were also compared. As also seen for mAb1, all mAb2 samples displayed essentially the same sigmoidal binding curve with $EC_{50}$ values of about 35 pM. The similarity of the binding curves suggests that the amount of trisulfide in the proteins did not affect the binding properties of mAb1 and mAb2.

In vitro and in vivo Stability of Trisulfides. The stability of trisulfide in mAbs was assessed in a defined buffer system, in rat serum in vitro and in vivo in rats following systemic administration. In the defined buffer system experiment, mAb1-B (containing 20% trisulfide at the LC5-HC5 linkage) and mAb1-D (containing 3% trisulfide at the LC5-HC5 linkage) were incubated at 5° C. and at 25° C. in citrate buffer at pH 6.5 for periods of one and three months. Peptide mapping analysis revealed that the trisulfide linkages were stable and that there was no change in the protein quality under these conditions. To assess the stability of the trisulfide in serum in vitro and in vivo, mAb1-B containing 20% trisulfide was incubated in rat serum at 37° C. for 16 h and 96 h; the same material was also injected into rats and isolated from the serum 24 and 72 h post injection. No change in the level of the trisulfide was detected in the samples incubated in rat serum in vitro compared with the untreated control (Table 15; FIG. 6). In contrast, no trisulfide was detected in the sample that had circulated in rat for 24 h and for 72 h following intraperitoneal injection. Since the recovery of the protein from the injected serum was essentially quantitative (see methods section), the data suggest that complete conversion of the trisulfide to disulfide occurs in vivo during the first 24 h of circulation. Furthermore, the levels of disulfides, observed in peptide map, were the same as those in the map of a mAb1 containing little trisulfide.

TABLE 15

Stability of trisulfides in rat serum in vitro and in vivo.

| Description of Samples of mAb1-B | Trisulfide at LC5-HC5 (%) |
|---|---|
| Control | 19.8 |
| Control, purified by IgSelect | 19.8 |
| purified by IgSelect after incubated at 37° C. in rat serum for 16 h | 20.0 |
| purified by IgSelect after incubated at 37° C. in rat serum for 96 h | 20.6 |
| IgSelect purified after circulation in rat for 24 h | <0.1 |
| IgSelect purified after circulation in rat for 72 h | <0.1 |

Discussion

We have demonstrated that trisulfides are a common post-translational modification in antibodies and can occur in all IgG frameworks, independent of their glycosylation state. The modification can occur in recombinant and natural antibodies as well as in non-clinical preparations and commercial therapeutics. Trisulfide levels in the samples varied from below the detection limit to >40%, but the presence of high levels of trisulfide had no observable effect on the function or stability of the antibody. Although there is very little published literature on trisulfides in proteins, our findings suggest that it is a very common modification. The scarcity of published data presumably arises because trisulfide detection requires the use of methods such as those described here that are directly targeted at their analysis.

Peptide mapping of non-reduced protein samples utilizing a LC-MS system is a sensitive and reliable method for identifying and quantifying trisulfides. In all IgG antibodies that were evaluated, trisulfides occurred in the heavy-light and heavy-heavy interchain linkages that connect the four subunits and not in any of the intrachain disulfides. The highest levels were consistently observed in the heavy-light chain linkage. To increase the throughput and to simplify the peptide mapping analysis, a focused Lys-C peptide mapping method for human IgG1 was developed. This protocol shortened analysis time significantly. The percentages of the trisulfide in the light and heavy chain linkage can be easily quantified from chromatograms using either UV traces or EICs. Quantification from the EIC is preferred when the level of trisulfide is below 3%. The detection limit of the method estimated from EICs is 0.1%, with a RSD of 3.8% based on more than twenty independent experiments. Because the peptide sequences containing LC5 and HC5 are the same in all human IgG1 antibodies, the Lys-C peptide mapping method developed for mAb1 is applicable to all human IgG1 antibodies. Similar peptide mapping strategies were successfully developed for quantification of trisulfide linkages in IgG2, IgG3, and IgG4 antibodies. Previously, Pristatsky and coworkers (Pristatsky et al., Anal. Chem. 81 (2009) 6148-6155) identified trisulfide modification of the hinge of a human IgG2 mAb as part of the characterization of the hinge disulfide structure. To facilitate characterization, the mAb had been fractionated on an ion exchange column. In the IgG2 mAb that we characterized—without fractionation—the primary site of modification was in the LC5-HC3 linkage and non-detectable levels were observed in the hinge region. Because of the low level of trisulfide in LC5-LC3 linkage in our preparation, levels in the hinge may have been below the limit of detection.

The effect of cell culture conditions on the trisulfide levels was surprising. In the nearly 100 mAb1 preparations that were purified and characterized, the level of trisulfide at the LC5-HC5 linkage ranged from <1% to 40%. Changes in culture conditions that seemed relatively minor and did not significantly affect growth and culture productivity resulted in large differences in trisulfide levels. In particular, culture duration and feeding strategy were important variables and product with reproducible trisulfide levels can be obtained by tightly controlling cell culture conditions.

We have shown that trisulfides can be chemically incorporated into antibodies by simple treatment with $H_2S$, confirming the original finding with hGH (U.S. Pat. No. 7,232, 894). Production of $H_2S$ by mammalian cells and tissues through the enzymatic breakdown of cysteine and homocysteine is well documented (Chiku et al., J. Biol. Chem. 284 (2009) 11601-11612; Kamoun, Amino Acids 26 (2004) 243-254; Singh et al., J. Biol. Chem. 284 (2009) 22457-22466; Stipanuk and Beck, Biochem. J. 206 (1982) 267-277; and Zhao and Wang, Am. J. Physiol. Heart Circ. Physiol. 283 (2002) H474-480) and could account for trisulfide formation during cell fermentation. The specificity of the chemical reaction is driven by solvent exposure of the interchain disulfides and by lack of exposure of intrachain disulfides, which are buried in the hydrophobic interior of antibodies. The low levels of $H_2S$ in human tissue (Goodwin et al., J. Anal. Toxicol. 13 (1989) 105-109; and Zhao et al., Embo J. 20 (2001) 6008-6016) could account of the trisulfide we observed in the endogenous myeloma human IgG1, IgG2, IgG3, and IgG4 antibodies, and suggests that people may be routinely exposed to proteins containing trisulfide linkages.

The trisulfide linkage was stable to prolonged storage at 4° C. and at room temperature and in rat serum in vitro, but was rapidly converted to a disulfide within 24 h after systemic administration to rats. The rapid conversion of the trisulfide to a disulfide in rats is consistent with other reported reduction-oxidation related changes that occur in vivo, e.g. the rearrangement of human IgG2 antibody hinge disulfides (Liu et al., J. Biol. Chem. 283 (2008) 29266-29272) and Fab-arm exchange of human IgG4 (Labrijn et al., Nat. Biotechnol. 27 (2009) 767-771). All of these pathways require that an interchain linkage be reduced and then reformed. In the absence of a reductant, the trisulfide linkage is very stable but reversal of the trisulfide to a disulfide can occur both in vitro and in vivo by a mild reduction-oxidation process.

In summary, we have found that insertion of a sulfur atom into an interchain disulfide bond to form a trisulfide is a common post-translational modification that has gone largely undetected because targeted methods are needed for their detection. The methods that were developed for identification and quantification of trisulfides should be applicable to any antibody and can be easily adapted for the characterization of other types of proteins. In the future, the identification and quantification of trisulfides will undoubtedly become an important test in the characterization of biopharmaceuticals.

Example 6

Full Peptide Mapping

To further analyze the effect of the on-column trisulfide conversion procedure non-reducing peptide mapping experiments were performed. Specifically, non-reducing peptide mapping was performed for three mAb-A Protein A eluate samples corresponding to (1) untreated mAb-A-LT (1.3% trisulfide), (2) mAb-A (17% trisulfide) untreated, or (3) mAb-A (17% trisulfide) subjected to a 1 mM cysteine column-wash treatment. The three samples (approximately 100 μg) were denatured and alkylated for an hour at 25° C. in 115 μL of 8 M guanidine, 0.1 mM NEM in 50 mM sodium phosphate buffer, pH 6.5. The samples were then diluted by mixing with 246 μL of 50 mM sodium phosphate buffer, pH 6.5 before an addition of 10 μg lysyl endopeptidase (Lys-C, Wako Chemicals). The digestion was performed at 25° C. for 18 hours. An aliquot of 90 μL of the protein digest (equivalent to 25 μg of protein) was separated on a YMC ODS-A column (2×250 mm, 5 μm, 120 Å) in a gradient of water, ACN with TFA, using an Agilent 1000 HPLC equipped with an ESI mass spectrometer (LCQ Deca XP, Thermo). The peptide map data were explored for the presence of trisulfide-modified, disulfide scrambled or free-cysteine containing peptides. The percentage of trisulfide modification was calculated as (peak area of trisulfide peptide)/(peak area of disulfide peptide+peak area of trisulfide peptide).

The level of H-L trisulfide in mAb-A was greatly decreased following the on-column 1 mM cysteine wash, from an initial level of 17% to a post-treatment level of 1.5%, which was similar to the level detected in untreated mAb-A-LT (1.3%). Moreover, the disulfide bonded peptide map for each sample was similar, with no detectable differences in the level of disulfide scrambling or free mAb sulfhydryl groups.

Example 7

Conversion of Trisulfides does not Affect Protein Structure or Folding

To assess the impact of trisulfide-to-disulfide conversion on protein conformation, hydrogen/deuterium exchange mass spectrometry (H/DX-MS) was performed to measure deuterium incorporation into IgG1 mAb-A. This technique has been used to explore structural changes and conformational dynamics of IgG1 molecules. Houde et al. *Anal. Chem.* 81: 2644 (2009). The H/DX was performed as described in Houde et al. with a labeling time course of 10 sec, 1, 10, 60 and 240 min. Deuterated samples were quenched at pH 2.6 by the addition of an equal volume of H$_2$O containing 200 mM sodium phosphate, 1 M TCEP and 4 M guanidine HCl, pH 2.3 with chilling to 0° C. Quenched samples were digested, desalted and separated online using a Waters UPLC based on a nanoACQUITY platform (Milford, Mass.) Wales et al., *Anal. Chem* 80 (2008) 6815). Approximately 20 pmoles of exchanged/quenched IgG1 was injected into the immobilized pepsin column. Digestion time was 2 min with a flow rate of 0.1 mL/min in 0.05% formic acid (FA) at 15° C. Peptic peptides were trapped on an ACQUITY UPLC BEH C18 1.7 μm peptide trap at 0° C. and desalted with water, 0.05% FA. Trapped peptides were eluted onto an ACQUITY UPLC BEH C18, 1.7 μm, 1×100 mm column for separation at 40 μL/min and separated in a linear ACN gradient (5-50%, 8 min) with 0.05% FA. Eluate was directed into a Waters Synapt HD MS with electrospray ionization and lock-mass correction (using Glu-fibrinogen peptide). Mass spectra were acquired from m/z 255 to 1800. Pepsin fragments were identified by a combination of exact mass and MS/MS, aided by Waters IdentityE software. Silva et al. *Mol. Cell. Proteomics* 5: 144 (2006). Peptide deuterium levels were determined as described (Weis et al. *J. Am Soc. Mass Spectrom.* 17: 1700 (2006)) using an HX-Express program. No adjustment was made for deuterium back-exchange and results are reported as relative deuterium level. Walsh, *Posttranslational modification of proteins: Expanding nature's inventory*, Ed. Roberts and Company Publishers, Greenwood Village, Colo. 1 (2006). Approximately 93% IgG1 amino acid sequence identity was confirmed by tandem MS. In total, the deuterium incorporation of 222 peptic peptides was monitored. The error associated with each deuterium incorporation point was ±0.2 Da, and differences >0.5 Da were considered significant.

This technique monitors the exchange of amide hydrogens present in the polypeptide backbone with hydrogen or deuterium in solution which is indicative of solvent exposure and hydrogen bonding, properties that vary dramatically with protein structure. Coupled with enzymatic digestion, the technique provides structural information localized to small regions of the protein (for example, short peptides spanning 3-10 residues) and thereby reveals detailed information on protein conformation in solution. Preparations of mAb-A containing low or high levels of H-L trisulfide, or treated with 1 mM cysteine while bound to protein A, were selected for analysis with the rationale that any alterations in protein conformation would be revealed by differences in amide hydrogen exchange. When a total of 140 different peptic peptides, representing 94% sequence coverage, were analyzed within each IgG1 mAb-A preparation, no differences in deuterium exchange were detected. Notably this included the three peptic peptides encompassing the L and H chain Cys residues that participate in the H-L and H-H inter-chain trisulfide or disulfide bonds. This indicated that high levels of H-L trisulfide, and on-column conversion of trisulfide to disulfide by cysteine, had no detectable effect on mAb-A structure and folding.

Consistent with this, mAb-A preparations containing low or high levels of H-L trisulfide, or treated with 1 mM cysteine, displayed similar folding characteristics when analyzed by differential scanning calorimetry. The DSC was performed using a MicroCal capillary VP-DSC system (Northampton, Mass., USA) with Origin VPViewer2000 v2.0.64 software. Sample concentration was 0.5 mg/mL in 50 mM sodium phosphate, 100 mM NaCl, pH 6.0. Thermograms were generated by scanning temperature from 25° C. to 100° C. at a rate of 2° C./min. Data were processed using Origin 7SR2 software, and no differences in transition temperature profiles detected.

Example 8

Prevention of Trisulfides by Inhibition of Cysteine Degradation

As shown above, hydrogen sulfide is present in the medium as a result of cysteine degradation. It is hypothesized that the hydrogen sulfide which forms from the feed medium is sufficient to induce trisulfide bond formation. To test this hypothesis, a small scale study was performed in flasks. Purified antibody with a known trisulfide content of 2% was spiked into basal medium with and without the presence of cells. As an additional comparison, cells were grown without the external addition of antibody but with the addition of the antibody storage buffer. On the third and fourth days of incubation, a 3% by volume addition of feed medium was delivered. The antibody was harvested on the fifth day, followed by purification, concentration, and analysis by peptide mapping for trisulfide content.

The amount of trisulfide bond formation is shown in in FIG. 7, comparing the purified antibody used for spike experiments (1.8% trisulfide content) to the subsequently harvested material. Antibody produced by cells contained approximately 4% trisulfide content which is nearly identical to the trisulfide content when antibody was exogenously added to the cells, despite the titer produced by cells representing only about 5% of the total antibody at the end of the 5 day culture. The cell-free condition contained spiked antibody with over 11% trisulfide content by day 5, which is over a six-fold increase from the starting content. It is clear from these data that incubation in medium without cells is sufficient to induce increases in trisulfide content, and the presence of cells actually diminishes the effect of incubation in medium.

Example 9

Reduction in Hydrogen Sulfide Release by Inhibitors of Cysteine Degradation

In order to test the effect of cysteine degradation inhibitors on release of hydrogen sulfide in cell-culture medium, various inhibitors were added to the medium at the concentration of 17.7 mM, which represents a 1:1 ratio to the concentration of cysteine in the medium. Released hydrogen sulfide concentration was measured after 24 hours of incubation. Briefly, 50 ml of medium was incubated overnight in a closed 100 ml bottle. The headspace was therefore equal to the liquid volume of the container. A Jerome 631-X hydrogen sulfide detector was connected to a short piece of silicon tubing to minimize holdup volume in the instrument. The end of the tubing was inserted into the headspace of the medium-containing bottle, and the Jerome 631-X detector sampled the headspace immediately after opening the bottle. FIG. 8 shows that pyruvate, methyl pyruvate, ethyl pyruvate, DL-glyceraldehyde, and glyoxylic acid all functionally stopped release of hydrogen sulfide.

Example 10

Effect of Pyruvate on Release of Hydrogen Sulfide

The effect of pyruvate on release of hydrogen sulfide from cysteine degradation was further tested. The experiments were performed as described above in Example 9. Concentration of released hydrogen sulfide was measured after incubation from solutions containing 17.7 mM cysteine, plus 200 g/L glucose or subgroups of amino acids, in the absence or presence of of pyruvate. FIG. 9 shows that release of hydrogen sulfide was significantly decreased when pyruvate was present in solution.

Example 11

Effect of Pyruvate on Release of Hydrogen Sulfide in Various Media

The effect of pyruvate on release of hydrogen sulfide from cysteine degradation was also tested in various cell-culture media, including feed liquid, IMDM and DMEM. All cysteine concentrations were normalized to that in the feed liquid. 17.7 mM pyruvate was added to the medium, which represents a 1:1 ratio of cysteine to pyruvate in the medium. The experiments were performed as described above for Example 9. FIG. 10 shows that pyruvate significantly reduced cysteine degradation (from about 60% to over 80% reduction) in all the media tested. Thus, pyruvate can reduce cysteine degradation and $H_2S$ release in a variety of compositions and decrease the number of trisulfide bonds.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All documents, articles, publications, patents, and patent applications mentioned in this specification are herein incorporated by reference to the same extent as if each individual publication or patent application was specifically and individually indicated to be incorporated by reference.

What is claimed is:

1. A method for reducing the formation of trisulfide bonds in proteins during large-scale production comprising culturing cells expressing said proteins in the presence of an effective amount of an inhibitor of cysteine degradation, whereby trisulfide linkage formation in said proteins is reduced relative to cells cultured in medium without the inhibitor of cysteine degradation, wherein the inhibitor of cysteine degradation is formaldehyde, acetaldehyde, propionaldehyde, butyraldehyde, stearic acid, arachidonic acid, docosahexaenoic acid, myristoleic acid, palmitoleic acid, elaidic acid, erucic acid, vaccenic acid, penicillamine, carotenes, alpha-tocopherol, ubiquinol, lactic acid, formic acid, oxalic acid, or uric acid, and wherein said cells are mammalian cells.

2. The method of claim 1, wherein said mammalian cells are selected from the group consisting of CHO (Chinese Hamster Ovary) (including CHO-K1, CHO DG44, and CHO DUXB11), VERO, HeLa, (human cervical carcinoma), CV1 (monkey kidney line), (including COS and COS-7), BHK (baby hamster kidney), MDCK, C127, PC 12, HEK-293 (including HEK-293T and HEK-293E), PER C6, NSO, W138, R1610 (Chinese hamsterfibroblast) BALBC/3T3 (mouse fibroblast), HAK (hamster kidney line), SP2/0 (mouse myeloma), P3x63-Ag3.653 (mouse myeloma), BFA-IcIBPT(bovine endothelial cells), RAJI (human lymphocyte) and 293 (human kidney) cells.

3. The method of claim 1, wherein the ratio of the inhibitor to cysteine is about 5:1 to 1:10.

4. The method of claim 1, wherein said inhibitor is added at a concentration of between about 50 µM and about 500 mM.

5. The method of claim 4, wherein said inhibitor is added at a concentration of between about 100 µM and about 100 mM.

6. The method of claim 5, wherein said inhibitor is added at a concentration of between about 1 mM and 100 mM.

7. The method of claim 6, wherein said inhibitor is added at a concentration of between about 5 mM and about 50 mM.

8. The method of claim 1, wherein said inhibitor is added at the beginning of the culture period.

9. The method of claim 1, wherein said inhibitor is added during a feed in a fed-batch culture.

10. The method of claim 1, wherein said cells are cultured in a bioreactor.

11. The method of claim 1, wherein said cells are grown in suspension.

12. The method of claim 1, wherein said protein is an antibody or Fc-fusion protein.

13. The method of claim 1, wherein said cells are in IMDM or DMEM.

* * * * *

UNITED STATES PATENT AND TRADEMARK OFFICE
CERTIFICATE OF CORRECTION

PATENT NO. : 10,590,454 B2
APPLICATION NO. : 15/785268
DATED : March 17, 2020
INVENTOR(S) : Rashmi Rohit Kshirsagar et al.

It is certified that error appears in the above-identified patent and that said Letters Patent is hereby corrected as shown below:

In the Claims

In Claim 2, Column 105, Lines 20-22, the text:
"(baby hamster kidney), MDCK, C127, PC 12, HEK-293 (including HEK-293T and HEK-293E), PER C6, NSO, W138, R1610 (Chinese hamsterfibroblast) BALBC/3T3"

Should read:
--(baby hamster kidney), MDCK, C127, PC12, HEK-293 (including HEK-293T and HEK-293E), PER C6, NSO, W138, R1610 (Chinese hamster fibroblast) BALBC/3T3--

Signed and Sealed this
Fifth Day of May, 2020

Andrei Iancu
*Director of the United States Patent and Trademark Office*

SEQUENCE LISTING

```
<160> NUMBER OF SEQ ID NOS: 101

<210> SEQ ID NO 1
<211> LENGTH: 118
<212> TYPE: PRT
<213> ORGANISM: Homo sapiens

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Glu Met Tyr Trp Val Arg Gln Ala Pro Gly Lys Gly Leu Glu Trp Val
        35                  40                  45

Ser Arg Ile Val Ser Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Thr Glu Gly Asp Asn Asp Ala Phe Asp Ile Trp Gly Gln Gly Thr
            100                 105                 110

Thr Val Thr Val Ser Ser
            115

<210> SEQ ID NO 2
<211> LENGTH: 5
<212> TYPE: PRT
<213> ORGANISM: Homo sapiens

<400> SEQUENCE: 2

His Tyr Glu Met Tyr
1               5

<210> SEQ ID NO 3
<211> LENGTH: 17
<212> TYPE: PRT
<213> ORGANISM: Homo sapiens

<400> SEQUENCE: 3

Arg Ile Val Ser Ser Gly Gly Phe Thr Lys Tyr Ala Asp Ser Val Lys
1               5                   10                  15

Gly

<210> SEQ ID NO 4
<211> LENGTH: 9
<212> TYPE: PRT
<213> ORGANISM: Homo sapiens

<400> SEQUENCE: 4

Glu Gly Asp Asn Asp Ala Phe Asp Ile
1               5

<210> SEQ ID NO 5
<211> LENGTH: 5
<212> TYPE: PRT
<213> ORGANISM: Homo sapiens

<400> SEQUENCE: 5

Ile Tyr Pro Met Phe
1               5

<210> SEQ ID NO 6
<211> LENGTH: 17
<212> TYPE: PRT
<213> ORGANISM: Homo sapiens

<400> SEQUENCE: 6

Trp Ile Gly Pro Ser Gly Gly Ile Thr Lys Tyr Ala Asp Ser Val Lys
1               5                   10                  15

Gly

<210> SEQ ID NO 7
<211> LENGTH: 10
<212> TYPE: PRT
<213> ORGANISM: Homo sapiens

<400> SEQUENCE: 7

Glu Gly His Asn Asp Trp Tyr Phe Asp Leu
1               5                   10
```

<210> SEQ ID NO 8
<211> LENGTH: 119
<212> TYPE: PRT
<213> ORGANISM: Homo sapiens

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Pro Met Phe Trp Val Arg Gln Ala Pro Gly Lys Gly Leu Glu Trp Val
        35                  40                  45

Ser Trp Ile Gly Pro Ser Gly Gly Ile Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Glu Gly His Asn Asp Trp Tyr Phe Asp Leu Trp Gly Arg Gly
            100                 105                 110

Thr Leu Val Thr Val Ser Ser
        115

<210> SEQ ID NO 9
<211> LENGTH: 5
<212> TYPE: PRT
<213> ORGANISM: Homo sapiens

<400> SEQUENCE: 9

Ile Tyr Pro Met Phe
1               5

<210> SEQ ID NO 10
<211> LENGTH: 17
<212> TYPE: PRT
<213> ORGANISM: Homo sapiens

<400> SEQUENCE: 10

Trp Ile Gly Pro Ser Gly Gly Ile Thr Lys Tyr Ala Asp Ser Val Lys
1               5                   10                  15

Gly

<210> SEQ ID NO 11
<211> LENGTH: 10
<212> TYPE: PRT
<213> ORGANISM: Homo sapiens

<400> SEQUENCE: 11

Glu Gly His Asn Asp Trp Tyr Phe Asp Leu
1               5                   10

<210> SEQ ID NO 12
<211> LENGTH: 118
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

```
            20                  25                  30
Glu Met Lys Trp Val Arg Gln Ala Pro Gly Lys Gly Leu Glu Trp Val
         35                  40                  45

Ser Val Ile Gly Pro Ser Gly Gly Phe Thr Phe Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Glu Gly Asp Asn Asp Ala Phe Asp Ile Trp Gly Gln Gly Thr
            100                 105                 110

Thr Val Thr Val Ser Ser
            115
```

<210> SEQ ID NO 13
<211> LENGTH: 5
<212> TYPE: PRT
<213> ORGANISM: Homo sapiens

<400> SEQUENCE: 13

```
Ala Tyr Glu Met Lys
 1               5
```

<210> SEQ ID NO 14
<211> LENGTH: 17
<212> TYPE: PRT
<213> ORGANISM: Homo sapiens

<400> SEQUENCE: 14

```
Val Ile Gly Pro Ser Gly Gly Phe Thr Phe Tyr Ala Asp Ser Val Lys
 1               5                  10                  15

Gly
```

<210> SEQ ID NO 15
<211> LENGTH: 9
<212> TYPE: PRT
<213> ORGANISM: Homo sapiens

<400> SEQUENCE: 15

```
Glu Gly Asp Asn Asp Ala Phe Asp Ile
 1               5
```

<210> SEQ ID NO 16
<211> LENGTH: 119
<212> TYPE: PRT
<213> ORGANISM: Homo sapiens

<400> SEQUENCE: 16

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
             20                  25                  30

Pro Met Phe Trp Val Arg Gln Ala Pro Gly Lys Gly Leu Glu Trp Val
         35                  40                  45

Ser Trp Ile Gly Pro Ser Gly Gly Ile Thr Lys Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
```

```
                85                  90                  95
Ala Arg Glu Gly Thr Tyr Asp Trp Tyr Leu Asp Leu Trp Gly Arg Gly
            100                 105                 110

Thr Leu Val Thr Val Ser Ser
            115

<210> SEQ ID NO 17
<211> LENGTH: 5
<212> TYPE: PRT
<213> ORGANISM: Homo sapiens

<400> SEQUENCE: 17

Ile Tyr Pro Met Phe
1               5

<210> SEQ ID NO 18
<211> LENGTH: 17
<212> TYPE: PRT
<213> ORGANISM: Homo sapiens

<400> SEQUENCE: 18

Trp Ile Gly Pro Ser Gly Gly Ile Thr Lys Tyr Ala Asp Ser Val Lys
1               5                   10                  15

Gly

<210> SEQ ID NO 19
<211> LENGTH: 10
<212> TYPE: PRT
<213> ORGANISM: Homo sapiens

<400> SEQUENCE: 19

Glu Gly Thr Tyr Asp Trp Tyr Leu Asp Leu
1               5                   10

<210> SEQ ID NO 20
<211> LENGTH: 108
<212> TYPE: PRT
<213> ORGANISM: Homo sapiens

<400> SEQUENCE: 20

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Met
                85                  90                  95

Tyr Thr Phe Gly Gln Gly Thr Lys Leu Glu Ile Lys
            100                 105

<210> SEQ ID NO 21
<211> LENGTH: 11
<212> TYPE: PRT
<213> ORGANISM: Homo sapiens

<400> SEQUENCE: 21
```

```
Arg Ala Ser Gln Ser Val Ser Ser Tyr Leu Ala
1               5                   10
```

<210> SEQ ID NO 22
<211> LENGTH: 7
<212> TYPE: PRT
<213> ORGANISM: Homo sapiens

<400> SEQUENCE: 22

```
Asp Ala Ser Asn Arg Ala Thr
1               5
```

<210> SEQ ID NO 23
<211> LENGTH: 10
<212> TYPE: PRT
<213> ORGANISM: Homo sapiens

<400> SEQUENCE: 23

```
Gln Gln Arg Ser Asn Trp Pro Met Tyr Thr
1               5                   10
```

<210> SEQ ID NO 24
<211> LENGTH: 107
<212> TYPE: PRT
<213> ORGANISM: Homo sapiens

<400> SEQUENCE: 24

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Lys Trp Pro Leu
                85                  90                  95

Thr Phe Gly Gly Gly Thr Lys Val Glu Ile Lys
            100                 105
```

<210> SEQ ID NO 25
<211> LENGTH: 11
<212> TYPE: PRT
<213> ORGANISM: Homo sapiens

<400> SEQUENCE: 25

```
Arg Ala Ser Gln Ser Val Ser Ser Tyr Leu Ala
1               5                   10
```

<210> SEQ ID NO 26
<211> LENGTH: 7
<212> TYPE: PRT
<213> ORGANISM: Homo sapiens

<400> SEQUENCE: 26

```
Asp Ala Ser Asn Arg Ala Thr
1               5
```

<210> SEQ ID NO 27

```
<211> LENGTH: 9
<212> TYPE: PRT
<213> ORGANISM: Homo sapiens

<400> SEQUENCE: 27

Gln Gln Tyr Asp Lys Trp Pro Leu Thr
1               5

<210> SEQ ID NO 28
<211> LENGTH: 107
<212> TYPE: PRT
<213> ORGANISM: Homo sapiens

<400> SEQUENCE: 28

Asp Ile Gln Met Thr Gln Ser Pro Ser Phe Leu Ser Ala Ser Val Gly
1               5                   10                  15

Asp Ser Val Ala Ile Thr Cys Arg Ala Ser Gln Asp Ile Ser Arg Tyr
            20                  25                  30

Leu Ala Trp Tyr Gln Gln Arg Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Thr Ser Leu Gln Pro
65                  70                  75                  80

Glu Asp Phe Gly Thr Tyr Tyr Cys Gln Gln Tyr Asp Thr Leu His Pro
                85                  90                  95

Ser Phe Gly Pro Gly Thr Thr Val Asp Ile Lys
            100                 105

<210> SEQ ID NO 29
<211> LENGTH: 11
<212> TYPE: PRT
<213> ORGANISM: Homo sapiens

<400> SEQUENCE: 29

Arg Ala Ser Gln Asp Ile Ser Arg Tyr Leu Ala
1               5                   10

<210> SEQ ID NO 30
<211> LENGTH: 7
<212> TYPE: PRT
<213> ORGANISM: Homo sapiens

<400> SEQUENCE: 30

Asp Ala Ser Asn Leu Gln Thr
1               5

<210> SEQ ID NO 31
<211> LENGTH: 9
<212> TYPE: PRT
<213> ORGANISM: Homo sapiens

<400> SEQUENCE: 31

Gln Gln Tyr Asp Thr Leu His Pro Ser
1               5

<210> SEQ ID NO 32
<211> LENGTH: 108
<212> TYPE: PRT
<213> ORGANISM: Homo sapiens

<400> SEQUENCE: 32
```

-continued

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Met
                85                  90                  95

Tyr Thr Phe Gly Gln Gly Thr Lys Leu Glu Ile Lys
            100                 105

<210> SEQ ID NO 33
<211> LENGTH: 11
<212> TYPE: PRT
<213> ORGANISM: Homo sapiens

<400> SEQUENCE: 33

Arg Ala Ser Gln Ser Val Ser Ser Tyr Leu Ala
1               5                   10

<210> SEQ ID NO 34
<211> LENGTH: 7
<212> TYPE: PRT
<213> ORGANISM: Homo sapiens

<400> SEQUENCE: 34

Asp Ala Ser Asn Arg Ala Thr
1               5

<210> SEQ ID NO 35
<211> LENGTH: 10
<212> TYPE: PRT
<213> ORGANISM: Homo sapiens

<400> SEQUENCE: 35

Gln Gln Arg Ser Asn Trp Pro Met Tyr Thr
1               5                   10

<210> SEQ ID NO 36
<211> LENGTH: 107
<212> TYPE: PRT
<213> ORGANISM: Homo sapiens

<400> SEQUENCE: 36

Asp Ile Gln Met Thr Gln Ser Pro Ser Phe Leu Ser Ala Ser Val Gly
1               5                   10                  15

Asp Ser Val Ala Ile Thr Cys Arg Ala Ser Gln Asp Ile Ser Arg Tyr
            20                  25                  30

Leu Ala Trp Tyr Gln Gln Arg Pro Gly Lys Ala Pro Lys Leu Leu Ile
        35                  40                  45

Tyr Asp Ala Ser Asn Leu Gln Thr Gly Val Pro Ser Arg Phe Ser Gly
    50                  55                  60

Ser Gly Ser Gly Thr Asp Phe Thr Phe Thr Ile Thr Ser Leu Gln Pro
65                  70                  75                  80

Glu Asp Phe Gly Thr Tyr Tyr Cys Gln Gln Tyr Asp Thr Leu His Pro
                85                  90                  95

```
Ser Phe Gly Pro Gly Thr Thr Val Asp Ile Lys
            100                 105
```

<210> SEQ ID NO 37
<211> LENGTH: 11
<212> TYPE: PRT
<213> ORGANISM: Homo sapiens
<400> SEQUENCE: 37

```
Arg Ala Ser Gln Asp Ile Ser Arg Tyr Leu Ala
1               5                   10
```

<210> SEQ ID NO 38
<211> LENGTH: 7
<212> TYPE: PRT
<213> ORGANISM: Homo sapiens
<400> SEQUENCE: 38

```
Asp Ala Ser Asn Leu Gln Thr
1               5
```

<210> SEQ ID NO 39
<211> LENGTH: 9
<212> TYPE: PRT
<213> ORGANISM: Homo sapiens
<400> SEQUENCE: 39

```
Gln Gln Tyr Asp Thr Leu His Pro Ser
1               5
```

<210> SEQ ID NO 40
<211> LENGTH: 121
<212> TYPE: PRT
<213> ORGANISM: Homo sapiens
<400> SEQUENCE: 40

```
Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
                20                  25                  30

Gly Met His Trp Val Lys Gln Ser His Ala Lys Ser Leu Glu Trp Ile
            35                  40                  45

Gly Val Ile Ser Thr Tyr Asn Gly Tyr Thr Asn Tyr Asn Gln Lys Phe
        50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Ala Tyr Tyr Gly Asn Leu Tyr Tyr Ala Met Asp Tyr Trp Gly
            100                 105                 110

Gln Gly Thr Ser Val Thr Val Ser Ser
        115                 120
```

<210> SEQ ID NO 41
<211> LENGTH: 5
<212> TYPE: PRT
<213> ORGANISM: Homo sapiens
<400> SEQUENCE: 41

```
Asp Tyr Gly Met His
1               5
```

```
<210> SEQ ID NO 42
<211> LENGTH: 17
<212> TYPE: PRT
<213> ORGANISM: Homo sapiens

<400> SEQUENCE: 42

Val Ile Ser Thr Tyr Asn Gly Tyr Thr Asn Tyr Asn Gln Lys Phe Lys
1               5                   10                  15
Gly

<210> SEQ ID NO 43
<211> LENGTH: 12
<212> TYPE: PRT
<213> ORGANISM: Homo sapiens

<400> SEQUENCE: 43

Ala Tyr Tyr Gly Asn Leu Tyr Tyr Ala Met Asp Tyr
1               5                   10

<210> SEQ ID NO 44
<211> LENGTH: 121
<212> TYPE: PRT
<213> ORGANISM: Homo sapiens

<400> SEQUENCE: 44

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Gly Ile His Trp Val Lys Gln Ser His Ala Lys Ser Leu Glu Trp Ile
        35                  40                  45

Gly Val Ile Ser Thr Tyr Asn Gly Tyr Thr Asn Tyr Asn Gln Lys Phe
    50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Ala Tyr Tyr Gly Asn Leu Tyr Tyr Ala Met Asp Tyr Trp Gly
            100                 105                 110

Gln Gly Thr Ser Val Thr Val Ser Ser
        115                 120

<210> SEQ ID NO 45
<211> LENGTH: 5
<212> TYPE: PRT
<213> ORGANISM: Homo sapiens

<400> SEQUENCE: 45

Asp Tyr Gly Ile His
1               5

<210> SEQ ID NO 46
<211> LENGTH: 17
<212> TYPE: PRT
<213> ORGANISM: Homo sapiens

<400> SEQUENCE: 46

Val Ile Ser Thr Tyr Asn Gly Tyr Thr Asn Tyr Asn Gln Lys Phe Lys
1               5                   10                  15
```

```
<210> SEQ ID NO 47
<211> LENGTH: 12
<212> TYPE: PRT
<213> ORGANISM: Homo sapiens

<400> SEQUENCE: 47

Ala Tyr Tyr Gly Asn Leu Tyr Tyr Ala Met Asp Tyr
1               5                   10

<210> SEQ ID NO 48
<211> LENGTH: 123
<212> TYPE: PRT
<213> ORGANISM: Homo sapiens

<400> SEQUENCE: 48

Gln Val Ser Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Gly Pro Asp Tyr Tyr Gly Tyr Tyr Pro Met Asp Tyr
            100                 105                 110

Trp Gly Gln Gly Thr Ser Val Thr Val Ser Ser
            115                 120

<210> SEQ ID NO 49
<211> LENGTH: 7
<212> TYPE: PRT
<213> ORGANISM: Homo sapiens

<400> SEQUENCE: 49

Thr Ser Gly Met Gly Val Ser
1               5

<210> SEQ ID NO 50
<211> LENGTH: 16
<212> TYPE: PRT
<213> ORGANISM: Homo sapiens

<400> SEQUENCE: 50

His Ile Tyr Trp Asp Asp Lys Arg Tyr Asn Pro Ser Leu Lys Ser
1               5                   10                  15

<210> SEQ ID NO 51
<211> LENGTH: 13
<212> TYPE: PRT
<213> ORGANISM: Homo sapiens

<400> SEQUENCE: 51

Arg Gly Pro Asp Tyr Tyr Gly Tyr Tyr Pro Met Asp Tyr
1               5                   10
```

<210> SEQ ID NO 52
<211> LENGTH: 121
<212> TYPE: PRT
<213> ORGANISM: Homo sapiens

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Gly Met His Trp Val Arg Gln Ala Pro Gly Gln Gly Leu Glu Trp Met
        35                  40                  45

Gly Val Ile Ser Thr Tyr Asn Gly Tyr Thr Asn Tyr Asn Gln Lys Phe
    50                  55                  60

Lys Gly Arg Val Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Tyr Tyr Gly Asn Leu Tyr Tyr Ala Met Asp Tyr Trp Gly
            100                 105                 110

Gln Gly Thr Leu Val Thr Val Ser Ser
        115                 120

<210> SEQ ID NO 53
<211> LENGTH: 10
<212> TYPE: PRT
<213> ORGANISM: Homo sapiens

<400> SEQUENCE: 53

Gly Tyr Thr Phe Thr Asp Tyr Gly Met His
1               5                   10

<210> SEQ ID NO 54
<211> LENGTH: 17
<212> TYPE: PRT
<213> ORGANISM: Homo sapiens

<400> SEQUENCE: 54

Val Ile Ser Thr Tyr Asn Gly Tyr Thr Asn Tyr Asn Gln Lys Phe Lys
1               5                   10                  15

Gly

<210> SEQ ID NO 55
<211> LENGTH: 12
<212> TYPE: PRT
<213> ORGANISM: Homo sapiens

<400> SEQUENCE: 55

Ala Tyr Tyr Gly Asn Leu Tyr Tyr Ala Met Asp Tyr
1               5                   10

<210> SEQ ID NO 56
<211> LENGTH: 121
<212> TYPE: PRT
<213> ORGANISM: Homo sapiens

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

```
Gly Met His Trp Val Arg Gln Ala Pro Gly Gln Gly Leu Glu Trp Ile
            35                  40                  45

Gly Val Ile Ser Thr Tyr Asn Gly Tyr Thr Asn Tyr Asn Gln Lys Phe
 50                  55                  60

Lys Gly Arg Ala Thr Met Thr Val Asp Lys Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Ala Tyr Tyr Gly Asn Leu Tyr Tyr Ala Met Asp Tyr Trp Gly
                100                 105                 110

Gln Gly Thr Leu Val Thr Val Ser Ser
            115                 120
```

<210> SEQ ID NO 57
<211> LENGTH: 10
<212> TYPE: PRT
<213> ORGANISM: Homo sapiens

<400> SEQUENCE: 57

```
Gly Tyr Thr Phe Thr Asp Tyr Gly Met His
 1               5                  10
```

<210> SEQ ID NO 58
<211> LENGTH: 17
<212> TYPE: PRT
<213> ORGANISM: Homo sapiens

<400> SEQUENCE: 58

```
Val Ile Ser Thr Tyr Asn Gly Tyr Thr Asn Tyr Asn Gln Lys Phe Lys
 1               5                  10                  15

Gly
```

<210> SEQ ID NO 59
<211> LENGTH: 12
<212> TYPE: PRT
<213> ORGANISM: Homo sapiens

<400> SEQUENCE: 59

```
Ala Tyr Tyr Gly Asn Leu Tyr Tyr Ala Met Asp Tyr
 1               5                  10
```

<210> SEQ ID NO 60
<211> LENGTH: 111
<212> TYPE: PRT
<213> ORGANISM: Homo sapiens

<400> SEQUENCE: 60

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
                 20                  25                  30

Ser Tyr Ser Tyr Met His Trp Tyr Gln Gln Lys Pro Gly Gln Pro Pro
             35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Ile Leu Asn Ile His
 65                  70                  75                  80

Pro Val Glu Glu Glu Asp Ala Ala Thr Tyr Tyr Cys Gln His Ser Arg
                 85                  90                  95
```

-continued

```
Glu Leu Pro Phe Thr Phe Gly Ser Gly Thr Lys Leu Glu Ile Lys
            100                 105                 110

<210> SEQ ID NO 61
<211> LENGTH: 15
<212> TYPE: PRT
<213> ORGANISM: Homo sapiens

<400> SEQUENCE: 61

Arg Ala Ser Lys Ser Val Ser Thr Ser Ser Tyr Ser Tyr Met His
1               5                   10                  15

<210> SEQ ID NO 62
<211> LENGTH: 6
<212> TYPE: PRT
<213> ORGANISM: Homo sapiens

<400> SEQUENCE: 62

Ala Ser Asn Leu Glu Ser
1               5

<210> SEQ ID NO 63
<211> LENGTH: 9
<212> TYPE: PRT
<213> ORGANISM: Homo sapiens

<400> SEQUENCE: 63

Gln His Ser Arg Glu Leu Pro Phe Thr
1               5

<210> SEQ ID NO 64
<211> LENGTH: 111
<212> TYPE: PRT
<213> ORGANISM: Homo sapiens

<400> SEQUENCE: 64

Asp Ile Val Leu Thr Gln Ser Pro Ala Ser Leu Ala Val Ser Leu Gly
1               5                   10                  15

Gln Arg Ala Thr Ile Ser Cys Arg Ala Asn Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Ile Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys
            100                 105                 110

<210> SEQ ID NO 65
<211> LENGTH: 15
<212> TYPE: PRT
<213> ORGANISM: Homo sapiens

<400> SEQUENCE: 65

Arg Ala Asn Lys Ser Val Ser Thr Ser Ser Tyr Ser Tyr Met His
1               5                   10                  15

<210> SEQ ID NO 66
```

<211> LENGTH: 6
<212> TYPE: PRT
<213> ORGANISM: Homo sapiens

<400> SEQUENCE: 66

Ala Ser Asn Leu Glu Ser
1               5

<210> SEQ ID NO 67
<211> LENGTH: 9
<212> TYPE: PRT
<213> ORGANISM: Homo sapiens

<400> SEQUENCE: 67

Gln His Ser Arg Glu Leu Pro Phe Thr
1               5

<210> SEQ ID NO 68
<211> LENGTH: 111
<212> TYPE: PRT
<213> ORGANISM: Homo sapiens

<400> SEQUENCE: 68

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Ser Tyr Ser Tyr Met His Trp Tyr Gln Gln Lys Pro Gly Gln Pro Pro
            35                  40                  45

Lys Leu Leu Ile Lys Tyr Thr Ser Asn Leu Glu Ser Gly Val Pro Ala
    50                  55                  60

Arg Phe Ser Gly Ser Gly Ser Gly Thr Asp Phe Ile Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys
            100                 105                 110

<210> SEQ ID NO 69
<211> LENGTH: 15
<212> TYPE: PRT
<213> ORGANISM: Homo sapiens

<400> SEQUENCE: 69

Arg Ala Ser Lys Ser Val Ser Thr Ser Ser Tyr Ser Tyr Met His
1               5                   10                  15

<210> SEQ ID NO 70
<211> LENGTH: 6
<212> TYPE: PRT
<213> ORGANISM: Homo sapiens

<400> SEQUENCE: 70

Thr Ser Asn Leu Glu Ser
1               5

<210> SEQ ID NO 71
<211> LENGTH: 9
<212> TYPE: PRT
<213> ORGANISM: Homo sapiens

<400> SEQUENCE: 71

Gln His Ser Arg Glu Leu Pro Trp Thr
1               5

<210> SEQ ID NO 72
<211> LENGTH: 111
<212> TYPE: PRT
<213> ORGANISM: Homo sapiens

<400> SEQUENCE: 72

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln His Ser Arg
                85                  90                  95

Glu Leu Pro Phe Thr Phe Gly Gly Gly Thr Lys Leu Glu Ile Lys
            100                 105                 110

<210> SEQ ID NO 73
<211> LENGTH: 15
<212> TYPE: PRT
<213> ORGANISM: Homo sapiens

<400> SEQUENCE: 73

Arg Ala Ser Lys Ser Val Ser Thr Ser Ser Tyr Ser Tyr Met His
1               5                   10                  15

<210> SEQ ID NO 74
<211> LENGTH: 7
<212> TYPE: PRT
<213> ORGANISM: Homo sapiens

<400> SEQUENCE: 74

Tyr Ala Ser Asn Leu Glu Ser
1               5

<210> SEQ ID NO 75
<211> LENGTH: 9
<212> TYPE: PRT
<213> ORGANISM: Homo sapiens

<400> SEQUENCE: 75

Gln His Ser Arg Glu Leu Pro Phe Thr
1               5

<210> SEQ ID NO 76
<211> LENGTH: 111
<212> TYPE: PRT
<213> ORGANISM: Homo sapiens

<400> SEQUENCE: 76

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

-continued

```
Ser Tyr Ser Tyr Met His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
 50                      55                  60

Arg Phe Ser Gly Ser Gly Ser Gly Thr Asp Phe Ile Leu Asn Ile His
 65                  70                  75                  80

Pro Met Glu Glu Asp Asp Thr Ala Met Tyr Phe Cys Gln His Ser Arg
                 85                  90                  95

Glu Leu Pro Phe Thr Phe Gly Gly Gly Thr Lys Leu Glu Ile Lys
                100                 105                 110
```

<210> SEQ ID NO 77
<211> LENGTH: 21
<212> TYPE: PRT
<213> ORGANISM: Homo sapiens

<400> SEQUENCE: 77

```
Arg Ala Thr Ile Ser Cys Arg Ala Ser Lys Ser Val Ser Thr Ser Ser
 1               5                  10                  15

Tyr Ser Tyr Met His
                20
```

<210> SEQ ID NO 78
<211> LENGTH: 7
<212> TYPE: PRT
<213> ORGANISM: Homo sapiens

<400> SEQUENCE: 78

```
Tyr Ala Ser Asn Leu Glu Ser
 1               5
```

<210> SEQ ID NO 79
<211> LENGTH: 9
<212> TYPE: PRT
<213> ORGANISM: Homo sapiens

<400> SEQUENCE: 79

```
Gln His Ser Arg Glu Leu Pro Phe Thr
 1               5
```

<210> SEQ ID NO 80
<211> LENGTH: 111
<212> TYPE: PRT
<213> ORGANISM: Homo sapiens

<400> SEQUENCE: 80

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
                20                  25                  30

Ser Tyr Ser Tyr Met His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
 50                      55                  60

Arg Phe Ser Gly Ser Gly Ser Gly Thr Asp Phe Ile Leu Asn Ile His
 65                  70                  75                  80

Pro Met Glu Glu Asp Asp Thr Ala Thr Tyr Tyr Cys Gln His Ser Arg
                 85                  90                  95

Glu Leu Pro Phe Thr Phe Gly Gly Gly Thr Lys Leu Glu Ile Lys
                100                 105                 110
```

<210> SEQ ID NO 81
<211> LENGTH: 15
<212> TYPE: PRT
<213> ORGANISM: Homo sapiens

<400> SEQUENCE: 81

Arg Ala Ser Lys Ser Val Ser Thr Ser Ser Tyr Ser Tyr Met His
1               5                   10                  15

<210> SEQ ID NO 82
<211> LENGTH: 7
<212> TYPE: PRT
<213> ORGANISM: Homo sapiens

<400> SEQUENCE: 82

Tyr Ala Ser Asn Leu Glu Ser
1               5

<210> SEQ ID NO 83
<211> LENGTH: 9
<212> TYPE: PRT
<213> ORGANISM: Homo sapiens

<400> SEQUENCE: 83

Gln His Ser Arg Glu Leu Pro Phe Thr
1               5

<210> SEQ ID NO 84
<211> LENGTH: 450
<212> TYPE: PRT
<213> ORGANISM: Artificial Sequence
<220> FEATURE:
<223> OTHER INFORMATION: Chimeric P4A8 heavy

<400> SEQUENCE: 84

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
                20                  25                  30

Gly Met His Trp Val Lys Gln Ser His Ala Lys Ser Leu Glu Trp Ile
            35                  40                  45

Gly Val Ile Ser Thr Tyr Asn Gly Tyr Thr Asn Tyr Asn Gln Lys Phe
        50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Ala Tyr Tyr Gly Asn Leu Tyr Tyr Ala Met Asp Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly
    450

<210> SEQ ID NO 85
<211> LENGTH: 218
<212> TYPE: PRT
<213> ORGANISM: Artificial Sequence
<220> FEATURE:
<223> OTHER INFORMATION: Chimeric P4A8 light

<400> SEQUENCE: 85

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Ile Leu Asn Ile His
65                  70                  75                  80

Pro Val Glu Glu Glu Asp Ala Ala Thr Tyr Tyr Cys Gln His Ser Arg
                85                  90                  95
```

Glu Leu Pro Phe Thr Phe Gly Ser Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 86
<211> LENGTH: 450
<212> TYPE: PRT
<213> ORGANISM: Homo sapiens

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Gly Met His Trp Val Arg Gln Ala Pro Gly Gln Gly Leu Glu Trp Met
        35                  40                  45

Gly Val Ile Ser Thr Tyr Asn Gly Tyr Thr Asn Tyr Asn Gln Lys Phe
    50                  55                  60

Lys Gly Arg Val Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Tyr Tyr Gly Asn Leu Tyr Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met

```
                        245                 250                 255
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 87
<211> LENGTH: 450
<212> TYPE: PRT
<213> ORGANISM: Homo sapiens

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Gly Met His Trp Val Arg Gln Ala Pro Gly Gln Gly Leu Glu Trp Ile
        35                  40                  45

Gly Val Ile Ser Thr Tyr Asn Gly Tyr Thr Asn Tyr Asn Gln Lys Phe
    50                  55                  60

Lys Gly Arg Ala Thr Met Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Tyr Tyr Gly Asn Leu Tyr Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Thr Val
        180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly
    450

<210> SEQ ID NO 88
<211> LENGTH: 218
<212> TYPE: PRT
<213> ORGANISM: Homo sapiens

<400> SEQUENCE: 88

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Ser Leu Asn Ile His
65                  70                  75                  80
```

```
Pro Met Glu Glu Asp Asp Thr Ala Met Tyr Phe Cys Gln His Ser Arg
                85                  90                  95

Glu Leu Pro Phe Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 89
<211> LENGTH: 218
<212> TYPE: PRT
<213> ORGANISM: Homo sapiens

<400> SEQUENCE: 89

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Ile Leu Asn Ile His
65                  70                  75                  80

Pro Met Glu Glu Asp Asp Thr Ala Met Tyr Phe Cys Gln His Ser Arg
                85                  90                  95

Glu Leu Pro Phe Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 90
<211> LENGTH: 218
<212> TYPE: PRT
<213> ORGANISM: Homo sapiens

<400> SEQUENCE: 90

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
             20                  25                  30

Ser Tyr Ser Tyr Met His Trp Tyr Gln Gln Lys Pro Gly Gln Pro Pro
         35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Ile Leu Asn Ile His
 65                  70                  75                  80

Pro Met Glu Glu Asp Asp Thr Ala Thr Tyr Tyr Cys Gln His Ser Arg
                 85                  90                  95

Glu Leu Pro Phe Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 91
<211> LENGTH: 447
<212> TYPE: PRT
<213> ORGANISM: Homo sapiens

<400> SEQUENCE: 91

Gln Val Gln Leu Val Gln Ser Gly Ala Glu Val Lys Lys Pro Gly Ala
 1               5                  10                  15

Ser Val Lys Val Ser Cys Lys Gly Ser Gly Tyr Thr Phe Thr Asp Tyr
             20                  25                  30

Gly Met His Trp Val Arg Gln Ala Pro Gly Gln Gly Leu Glu Trp Met
         35                  40                  45

Gly Val Ile Ser Thr Tyr Asn Gly Tyr Thr Asn Tyr Asn Gln Lys Phe
 50                  55                  60

Lys Gly Arg Val Thr Met Thr Val Asp Lys Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ala Tyr Tyr Gly Asn Leu Tyr Tyr Ala Met Asp Tyr Trp Gly
            100                 105                 110

Gln Gly Thr Leu Val Thr Val Ser Ser Ala Ser Thr Lys Gly Pro Ser
```

```
                  115                 120                 125
Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Ala Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 92
<211> LENGTH: 450
<212> TYPE: PRT
<213> ORGANISM: Homo sapiens

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
                20                  25                  30

Gly Met His Trp Val Arg Gln Ala Pro Gly Gln Gly Leu Glu Trp Met
            35                  40                  45
```

```
Gly Val Ile Ser Thr Tyr Asn Gly Tyr Thr Asn Tyr Asn Gln Lys Phe
 50                  55                  60

Lys Gly Arg Val Thr Met Thr Val Asp Lys Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ala Tyr Tyr Gly Asn Leu Tyr Tyr Ala Met Asp Tyr Trp Gly
            100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Ala Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
450
```

-continued

```
<210> SEQ ID NO 93
<211> LENGTH: 108
<212> TYPE: PRT
<213> ORGANISM: Homo sapiens

<400> SEQUENCE: 93

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Tyr Thr Phe Gly Gln Gly Thr Lys Leu Glu Ile Lys
            100                 105

<210> SEQ ID NO 94
<211> LENGTH: 10
<212> TYPE: PRT
<213> ORGANISM: Homo sapiens

<400> SEQUENCE: 94

Gln Gln Arg Ser Asn Trp Pro Leu Tyr Thr
1               5                   10

<210> SEQ ID NO 95
<211> LENGTH: 108
<212> TYPE: PRT
<213> ORGANISM: Homo sapiens

<400> SEQUENCE: 95

Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Phe
                85                  90                  95

Tyr Thr Phe Gly Gln Gly Thr Lys Leu Glu Ile Lys
            100                 105

<210> SEQ ID NO 96
<211> LENGTH: 10
<212> TYPE: PRT
<213> ORGANISM: Homo sapiens

<400> SEQUENCE: 96

Gln Gln Arg Ser Asn Trp Pro Phe Tyr Thr
1               5                   10
```

<210> SEQ ID NO 97
<211> LENGTH: 119
<212> TYPE: PRT
<213> ORGANISM: Homo sapiens

<400> SEQUENCE: 97

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ile Tyr
            20                  25                  30
Pro Met Phe Trp Val Arg Gln Ala Pro Gly Lys Gly Leu Glu Trp Val
        35                  40                  45
Ser Trp Ile Gly Pro Ser Gly Gly Ile Thr Lys Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Thr Tyr Tyr Cys
                85                  90                  95
Ala Arg Glu Gly His Asn Asp Trp Tyr Phe Asp Leu Trp Gly Arg Gly
            100                 105                 110
Thr Leu Val Thr Val Ser Ser
        115

<210> SEQ ID NO 98
<211> LENGTH: 11
<212> TYPE: PRT
<213> ORGANISM: Homo sapiens

<400> SEQUENCE: 98

Arg Ala Ser Gln Ser Val Ser Ser Tyr Leu Ala
1               5                   10

<210> SEQ ID NO 99
<211> LENGTH: 11
<212> TYPE: PRT
<213> ORGANISM: Homo sapiens

<400> SEQUENCE: 99

Arg Ala Ser Gln Ser Val Ser Ser Tyr Leu Ala
1               5                   10

<210> SEQ ID NO 100
<211> LENGTH: 7
<212> TYPE: PRT
<213> ORGANISM: Homo sapiens

<400> SEQUENCE: 100

Asp Ala Ser Asn Arg Ala Thr
1               5

<210> SEQ ID NO 101
<211> LENGTH: 7
<212> TYPE: PRT
<213> ORGANISM: Homo sapiens

<400> SEQUENCE: 101

Asp Ala Ser Asn Arg Ala Thr
1               5